US012642920B2

(12) United States Patent
Hebrank et al.

(10) Patent No.: US 12,642,920 B2
(45) Date of Patent: Jun. 2, 2026

(54) DELIVERY OF SMALL DROPLETS TO THE RESPIRATORY SYSTEM VIA ELECTRONIC BREATH ACTUATED DROPLET DELIVERY DEVICE

(71) Applicant: Pneuma Respiratory, Inc., Boone, NC (US)

(72) Inventors: John H. Hebrank, Boone, NC (US); Charles Eric Hunter, Boone, NC (US); Matthew Culpepper, Boone, NC (US); Judson Sidney Clements, Boone, NC (US)

(73) Assignee: PNEUMA RESPIRATORY, INC., Boone, NC (US)

( * ) Notice: Subject to any disclaimer, the term of this patent is extended or adjusted under 35 U.S.C. 154(b) by 1091 days.

(21) Appl. No.: 17/619,960

(22) PCT Filed: Jun. 29, 2020

(86) PCT No.: PCT/US2020/040132
§ 371 (c)(1),
(2) Date: Dec. 16, 2021

(87) PCT Pub. No.: WO2020/264501
PCT Pub. Date: Dec. 30, 2020

(65) Prior Publication Data
US 2022/0296823 A1     Sep. 22, 2022

Related U.S. Application Data

(60) Provisional application No. 63/001,225, filed on Mar. 27, 2020, provisional application No. 62/883,028, (Continued)

(51) Int. Cl.
| A61M 11/00 | (2006.01) |
| A61M 11/02 | (2006.01) |
| B05B 17/00 | (2006.01) |

(52) U.S. Cl.
CPC ......... *A61M 11/002* (2014.02); *A61M 11/005* (2013.01); *A61M 11/02* (2013.01); *A61M 2205/0238* (2013.01); *B05B 17/0646* (2013.01)

(58) Field of Classification Search
CPC .... A61M 11/002; A61M 11/005; A61M 11/02
See application file for complete search history.

(56) References Cited

U.S. PATENT DOCUMENTS

| 3,934,585 A | 1/1976 | Maurice |
| 3,970,250 A | 7/1976 | Drews |

(Continued)

FOREIGN PATENT DOCUMENTS

| AU | 2012258488 | 1/2013 |
| CA | 2364248 | 8/2006 |

(Continued)

OTHER PUBLICATIONS

Copley, "Understanding cascade impaction and its importance for inhaler testing," Copley Scientific, Copley White Paper [serial online], Jul. 2007 [retrieved on May 7, 2017]. Retrieved from the Internet: URL: http://www.copleyscientific.com/files/ww/articles/Understanding%20Cascade%20Impaction%20White%20Paper.pdf; 6 pp.

(Continued)

*Primary Examiner* — Kendra D Carter
*Assistant Examiner* — Jaeick Jang
(74) *Attorney, Agent, or Firm* — Polsinelli PC

(57) ABSTRACT

An ejector mechanism of a droplet delivery device includes a piezoelectric actuator coupled to an acoustic horn and an aperture plate including a plurality of openings. At least the fluid entrance side of one or more of the plurality of openings is configured to provide a surface contact angle of less than 90 degrees and the piezoelectric actuator is operable to oscillate the aperture plate at a frequency to thereby
(Continued)

generate an ejected stream of droplets such that at least about 50% of the droplets have an average ejected droplet diameter of less than about 6 microns during use. A sealing mechanism is provided at an interface of the aperture plate and a detachable fluid cartridge.

21 Claims, 17 Drawing Sheets

Related U.S. Application Data filed on Aug. 5, 2019, provisional application No. 62/867,719, filed on Jun. 27, 2019.

(56) References Cited

U.S. PATENT DOCUMENTS

| | | | |
|---|---|---|---|
| 5,021,701 A | 6/1991 | Takahashi et al. | |
| 5,164,740 A | 11/1992 | Ivri | |
| 5,363,842 A | 11/1994 | Mishelevich et al. | |
| 5,435,282 A * | 7/1995 | Haber | A61M 15/0065 |
| | | | 239/338 |
| 5,487,378 A * | 1/1996 | Robertson | A61M 15/0015 |
| | | | 128/200.14 |
| 5,586,550 A | 12/1996 | Ivri et al. | |
| 5,607,410 A | 3/1997 | Branch | |
| 5,630,793 A | 5/1997 | Rowe | |
| 5,758,637 A | 6/1998 | Ivri et al. | |
| 5,826,570 A | 10/1998 | Goodman et al. | |
| 5,828,394 A | 10/1998 | Khuri-Yakub et al. | |
| 5,881,716 A | 3/1999 | Wirch et al. | |
| 5,884,620 A | 3/1999 | Gonda et al. | |
| 5,894,841 A | 4/1999 | Voges | |
| 5,906,202 A | 5/1999 | Schuster et al. | |
| 5,938,117 A * | 8/1999 | Ivri | B41J 2/025 |
| | | | 239/4 |
| 5,979,247 A | 11/1999 | Kizawa | |
| 6,011,062 A | 1/2000 | Schneider et al. | |
| 6,062,212 A | 5/2000 | Davison et al. | |
| 6,071,498 A | 6/2000 | Narodylo et al. | |
| 6,085,740 A | 7/2000 | Ivri et al. | |
| 6,196,219 B1 | 3/2001 | Hess et al. | |
| 6,235,177 B1 | 5/2001 | Borland et al. | |
| 6,443,146 B1 | 9/2002 | Voges | |
| 6,523,762 B1 | 2/2003 | Luginbuhl et al. | |
| 6,615,826 B1 | 9/2003 | Gabrio et al. | |
| 6,637,430 B1 | 10/2003 | Voges et al. | |
| 6,896,910 B2 | 5/2005 | Kim et al. | |
| 6,978,941 B2 | 12/2005 | Litherland et al. | |
| 6,981,499 B2 | 1/2006 | Anderson et al. | |
| 7,191,777 B2 | 3/2007 | Brand et al. | |
| 7,198,044 B2 | 4/2007 | Trueba | |
| 7,219,664 B2 | 5/2007 | Ruckdeschel et al. | |
| 7,628,339 B2 | 12/2009 | Ivri et al. | |
| 7,648,957 B2 | 1/2010 | Heyden et al. | |
| 7,708,011 B2 | 5/2010 | Hochrainer et al. | |
| 7,883,031 B2 | 2/2011 | Collins, Jr. et al. | |
| 7,900,625 B2 | 3/2011 | Kleinstreuer et al. | |
| 7,954,486 B2 | 6/2011 | Papania et al. | |
| 7,976,140 B2 | 7/2011 | Umeda | |
| 8,012,136 B2 | 9/2011 | Collins, Jr. et al. | |
| 8,367,734 B1 | 2/2013 | Gao et al. | |
| 8,474,452 B2 | 7/2013 | Gumaste et al. | |
| 8,545,463 B2 | 10/2013 | Collins, Jr. et al. | |
| 8,555,874 B2 | 10/2013 | Fink et al. | |
| 8,658,258 B2 | 2/2014 | Hanson | |
| 8,684,980 B2 | 4/2014 | Hunter et al. | |
| 8,733,935 B2 | 5/2014 | Ballou, Jr. et al. | |
| 8,753,308 B2 | 6/2014 | Palmer et al. | |
| 8,936,021 B2 | 1/2015 | Collins, Jr. | |
| 8,985,100 B2 | 3/2015 | Minocchieri et al. | |
| 9,087,145 B2 | 7/2015 | Ballou, Jr. et al. | |
| 9,227,029 B2 | 1/2016 | Addington et al. | |
| 9,242,054 B2 | 1/2016 | Fink et al. | |
| 9,452,274 B2 | 9/2016 | Addington et al. | |
| 9,463,486 B2 | 10/2016 | Wilkerson et al. | |
| 9,539,604 B2 | 1/2017 | Wilkerson et al. | |
| 9,956,360 B2 | 5/2018 | Germinario et al. | |
| 9,962,507 B2 | 5/2018 | Germinario et al. | |
| 10,449,314 B2 | 10/2019 | Germinario et al. | |
| 10,525,220 B2 | 1/2020 | Hunter et al. | |
| 10,568,543 B2 | 2/2020 | Yan | |
| 10,898,666 B2 | 1/2021 | Germinario et al. | |
| 2002/0002975 A1 | 1/2002 | Power | |
| 2002/0032387 A1 | 3/2002 | Geva et al. | |
| 2002/0046750 A1 | 4/2002 | Gonda et al. | |
| 2002/0071871 A1 | 6/2002 | Snyder et al. | |
| 2002/0121274 A1 | 9/2002 | Borland et al. | |
| 2003/0072717 A1 | 4/2003 | Reinhold et al. | |
| 2003/0098022 A1 | 5/2003 | Nakao et al. | |
| 2003/0101991 A1 | 6/2003 | Trueba | |
| 2003/0127538 A1 | 7/2003 | Patel et al. | |
| 2003/0140921 A1 | 7/2003 | Smith et al. | |
| 2003/0150445 A1 | 8/2003 | Power et al. | |
| 2003/0196654 A1 | 10/2003 | Stein | |
| 2003/0205229 A1 | 11/2003 | Crockford et al. | |
| 2003/0230303 A1 | 12/2003 | Nichols et al. | |
| 2004/0009231 A1 | 1/2004 | Jackson et al. | |
| 2004/0139963 A1 | 7/2004 | Ivri et al. | |
| 2004/0195403 A1 | 10/2004 | Atterybury et al. | |
| 2004/0215157 A1 | 10/2004 | Peclat et al. | |
| 2004/0256487 A1 | 12/2004 | Collins, Jr. et al. | |
| 2005/0011514 A1 | 1/2005 | Power et al. | |
| 2005/0077315 A1 | 4/2005 | Pavlu et al. | |
| 2005/0121025 A1 | 6/2005 | Gamard et al. | |
| 2005/0150489 A1 | 7/2005 | Dunfield et al. | |
| 2005/0172476 A1 * | 8/2005 | Stone | B01F 23/41 |
| | | | 29/592.1 |
| 2005/0172958 A1 | 8/2005 | Singer et al. | |
| 2005/0217666 A1 | 10/2005 | Fink et al. | |
| 2005/0224075 A1 | 10/2005 | Childers et al. | |
| 2005/0236501 A1 | 10/2005 | Zimlich, Jr. et al. | |
| 2007/0023036 A1 | 2/2007 | Grychowski et al. | |
| 2007/0044793 A1 | 3/2007 | Kleinstreuer et al. | |
| 2007/0083677 A1 | 4/2007 | Cecka et al. | |
| 2007/0119969 A1 | 5/2007 | Collins, Jr. et al. | |
| 2007/0125370 A1 | 6/2007 | Denyer et al. | |
| 2007/0157931 A1 | 7/2007 | Parker et al. | |
| 2007/0240714 A1 | 10/2007 | Dunne et al. | |
| 2007/0248645 A1 | 10/2007 | Bague et al. | |
| 2007/0267010 A1 | 11/2007 | Fink et al. | |
| 2008/0000470 A1 | 1/2008 | Minocchieri et al. | |
| 2008/0059228 A1 | 3/2008 | Bossi et al. | |
| 2008/0142010 A1 | 6/2008 | Weaver et al. | |
| 2008/0243050 A1 | 10/2008 | Power et al. | |
| 2008/0271732 A1 | 11/2008 | Weaver et al. | |
| 2008/0283057 A1 | 11/2008 | Rohrschneider et al. | |
| 2008/0295827 A1 | 12/2008 | Kobayashi | |
| 2008/0308096 A1 | 12/2008 | Borgschulte et al. | |
| 2009/0038610 A1 | 2/2009 | Bogh et al. | |
| 2009/0093772 A1 | 4/2009 | Genosar et al. | |
| 2009/0107492 A1 | 4/2009 | Ooida | |
| 2009/0114218 A1 | 5/2009 | Veatch | |
| 2009/0114742 A1 | 5/2009 | Collins, Jr. | |
| 2009/0118243 A1 | 5/2009 | Gjorstrup | |
| 2009/0134235 A1 | 5/2009 | Ivri | |
| 2009/0167812 A1 | 7/2009 | Asai et al. | |
| 2009/0192443 A1 | 7/2009 | Collins, Jr. | |
| 2009/0212133 A1 | 8/2009 | Collins, Jr. | |
| 2009/0235925 A1 | 9/2009 | Power et al. | |
| 2009/0270752 A1 | 10/2009 | Coifman | |
| 2009/0272818 A1 | 11/2009 | Valpey, III et al. | |
| 2009/0314292 A1 | 12/2009 | Overfield et al. | |
| 2009/0317496 A1 | 12/2009 | Park et al. | |
| 2010/0037894 A1 | 2/2010 | Rouse et al. | |
| 2010/0078013 A1 | 4/2010 | Power et al. | |
| 2010/0089395 A1 | 4/2010 | Power et al. | |
| 2010/0156995 A1 | 6/2010 | Kanda et al. | |
| 2010/0222752 A1 | 9/2010 | Collins, Jr. et al. | |
| 2010/0282247 A1 | 11/2010 | Kadrichu et al. | |
| 2011/0108025 A1 | 5/2011 | Fink et al. | |
| 2011/0230820 A1 | 9/2011 | Lillis et al. | |
| 2011/0253805 A1 | 10/2011 | Lee | |

(56) References Cited

U.S. PATENT DOCUMENTS

| | | | |
|---|---|---|---|
| 2012/0037154 A1 | 2/2012 | Gallem et al. | |
| 2012/0048265 A1 | 3/2012 | Smaldone | |
| 2012/0251594 A1 | 10/2012 | Longest et al. | |
| 2012/0266878 A1 | 10/2012 | Watanabe et al. | |
| 2012/0291781 A1 | 11/2012 | Kaufmann et al. | |
| 2013/0079732 A1 | 3/2013 | Burt et al. | |
| 2013/0150812 A1 | 6/2013 | Hunter et al. | |
| 2013/0172830 A1 | 7/2013 | Hunter et al. | |
| 2013/0239956 A1 | 9/2013 | Schulz et al. | |
| 2013/0267864 A1 | 10/2013 | Addington et al. | |
| 2013/0269694 A1 | 10/2013 | Patton et al. | |
| 2013/0284165 A1 | 10/2013 | Krimsky | |
| 2013/0299607 A1* | 11/2013 | Wilkerson | B05B 17/0661 |
| | | | 239/328 |
| 2013/0327323 A1 | 12/2013 | Rubin | |
| 2013/0330400 A1 | 12/2013 | Perkins et al. | |
| 2013/0334335 A1 | 12/2013 | Wilkerson et al. | |
| 2013/0334339 A1 | 12/2013 | Xu | |
| 2014/0037735 A1 | 2/2014 | Montgomery | |
| 2014/0116426 A1 | 5/2014 | Mullinger et al. | |
| 2014/0187969 A1 | 7/2014 | Hunter et al. | |
| 2014/0190496 A1 | 7/2014 | Wensley et al. | |
| 2014/0213925 A1 | 7/2014 | Chan et al. | |
| 2014/0283859 A1 | 9/2014 | Minskoff et al. | |
| 2014/0336618 A1 | 11/2014 | Wilkerson et al. | |
| 2015/0018694 A1 | 1/2015 | Gomo | |
| 2015/0101596 A1 | 4/2015 | Hogan | |
| 2015/0136155 A1 | 5/2015 | Verleur et al. | |
| 2015/0164375 A1 | 6/2015 | Schindhelm et al. | |
| 2015/0174348 A1 | 6/2015 | Tunnell et al. | |
| 2015/0196060 A1 | 7/2015 | Wensley et al. | |
| 2015/0273165 A1 | 10/2015 | Hadash | |
| 2015/0328151 A1 | 11/2015 | Ballou, Jr. et al. | |
| 2015/0352301 A1 | 12/2015 | Stedman et al. | |
| 2016/0001018 A1 | 1/2016 | Fink et al. | |
| 2016/0001019 A1 | 1/2016 | Fink et al. | |
| 2016/0106341 A1 | 4/2016 | Adam et al. | |
| 2016/0213866 A1 | 7/2016 | Tan | |
| 2016/0245830 A1 | 8/2016 | Mace et al. | |
| 2016/0310982 A1 | 10/2016 | Von Hollen | |
| 2016/0325055 A1 | 11/2016 | Cameron | |
| 2016/0354557 A1 | 12/2016 | McPherson Allnutt et al. | |
| 2017/0035924 A1 | 2/2017 | Yang et al. | |
| 2017/0039344 A1 | 2/2017 | Bitran et al. | |
| 2017/0106153 A1 | 4/2017 | Davidson et al. | |
| 2017/0106155 A1 | 4/2017 | Reed et al. | |
| 2017/0128677 A1 | 5/2017 | Eilat et al. | |
| 2017/0158776 A1 | 6/2017 | Feltquate et al. | |
| 2017/0203058 A1 | 7/2017 | Davidson et al. | |
| 2017/0203323 A1 | 7/2017 | Gschwind et al. | |
| 2017/0224706 A1 | 8/2017 | Surber | |
| 2017/0270260 A1 | 9/2017 | Shetty et al. | |
| 2017/0274163 A1 | 9/2017 | Oliveras et al. | |
| 2017/0304565 A1 | 10/2017 | Allosery | |
| 2017/0304566 A1 | 10/2017 | Allosery | |
| 2017/0319796 A1 | 11/2017 | Germinario et al. | |
| 2017/0319797 A1* | 11/2017 | Germinario | G16H 40/63 |
| 2017/0333646 A1 | 11/2017 | Hemy et al. | |
| 2018/0056018 A1 | 3/2018 | Canvin et al. | |
| 2018/0116871 A1 | 5/2018 | Hunter et al. | |
| 2018/0193175 A1 | 7/2018 | Bluecher et al. | |
| 2018/0317557 A1 | 11/2018 | Monsees et al. | |
| 2018/0344955 A1 | 12/2018 | Germinario et al. | |
| 2018/0369515 A1 | 12/2018 | Germinario et al. | |
| 2019/0117907 A1 | 4/2019 | Germinario et al. | |
| 2019/0125985 A1 | 5/2019 | Germinario et al. | |
| 2019/0125986 A1 | 5/2019 | Germinario et al. | |
| 2019/0125987 A1 | 5/2019 | Germinario et al. | |
| 2019/0134330 A1 | 5/2019 | Germinario et al. | |
| 2019/0166913 A1* | 6/2019 | Trzecieski | A61M 15/06 |
| 2019/0358420 A1 | 11/2019 | Hunter et al. | |
| 2020/0246556 A1* | 8/2020 | Osoegawa | A61M 15/0085 |
| 2020/0276398 A1 | 9/2020 | Hebrank et al. | |
| 2020/0289770 A1 | 9/2020 | Hebrank et al. | |
| 2020/0330267 A1* | 10/2020 | Li | A61M 35/00 |
| 2020/0353186 A1 | 11/2020 | Hebrank et al. | |
| 2021/0106772 A1 | 4/2021 | Hebrank et al. | |
| 2021/0113783 A1* | 4/2021 | Danek | A61K 31/4439 |
| 2021/0197222 A1* | 7/2021 | Bayat | A24F 40/05 |
| 2021/0219605 A1* | 7/2021 | Bayat | A24F 40/53 |
| 2021/0236745 A1 | 8/2021 | Germinario et al. | |
| 2021/0275760 A1 | 9/2021 | Hunter et al. | |
| 2022/0001122 A1 | 1/2022 | Hunter et al. | |

FOREIGN PATENT DOCUMENTS

| | | |
|---|---|---|
| CA | 3079189 A1 | 4/2019 |
| CN | 1788806 | 6/2006 |
| CN | 103118642 A | 5/2013 |
| CN | 104511072 | 4/2015 |
| CN | 104582647 A | 4/2015 |
| CN | 105209096 A | 12/2015 |
| CN | 204995458 | 1/2016 |
| CN | 205019058 | 2/2016 |
| CN | 106687221 B | 5/2017 |
| CN | 109475707 A | 3/2019 |
| CN | 109906120 A | 6/2019 |
| EP | 0923957 A1 | 6/1999 |
| EP | 2724741 | 4/2014 |
| EP | 3793746 A1 | 3/2021 |
| JP | H11-042219 | 2/1999 |
| JP | 2003-265994 | 9/2003 |
| JP | 2006-68508 | 3/2006 |
| KR | 10-2019-122453 | 10/2019 |
| WO | WO 96/09846 | 4/1996 |
| WO | WO 96/14163 | 5/1996 |
| WO | WO 98/48873 | 11/1998 |
| WO | WO 00/10634 | 3/2000 |
| WO | WO 00/47335 | 8/2000 |
| WO | WO 01/87378 | 11/2001 |
| WO | WO 03/020349 | 3/2003 |
| WO | WO 03/059413 | 7/2003 |
| WO | WO 2004/078025 | 9/2004 |
| WO | WO 2006/013952 | 2/2006 |
| WO | WO 2006/083014 | 8/2006 |
| WO | WO 2008/056986 | 5/2008 |
| WO | WO 2008/058941 | 5/2008 |
| WO | WO 2008/116165 | 9/2008 |
| WO | WO 2009/012371 | 1/2009 |
| WO | WO 2009/111612 | 9/2009 |
| WO | WO 2010/065452 | 6/2010 |
| WO | WO 2011/091268 | 7/2011 |
| WO | WO 2012/026963 | 3/2012 |
| WO | WO 2013/098334 | 7/2013 |
| WO | WO 2013/158352 | 10/2013 |
| WO | WO 2013/158967 | 10/2013 |
| WO | WO 2013/173321 | 11/2013 |
| WO | WO 2015/136529 | 9/2015 |
| WO | WO 2016/001924 | 1/2016 |
| WO | WO 2016/003738 | 1/2016 |
| WO | WO 2017/056103 | 4/2017 |
| WO | 2017149165 A1 | 9/2017 |
| WO | 2017192767 A1 | 11/2017 |
| WO | WO 2018/213834 | 11/2018 |
| WO | WO 2019/071008 | 4/2019 |
| WO | WO 2019/079461 | 4/2019 |
| WO | WO 2019/219865 | 11/2019 |
| WO | 2020032383 A1 | 2/2020 |
| WO | WO 2020/072478 | 4/2020 |
| WO | WO 2020/154497 | 7/2020 |
| WO | WO 2020/227717 | 11/2020 |

OTHER PUBLICATIONS

Kharitonov, "Exhaled markers of inflammatory lung diseases: ready for routine monitoring?" *Swiss Med Wkly*, 2004; 134: 175-192.

Broeders et al., "Inhalation Profiles in Asthmatics and COPD Patients: Reproducibility and Effect of Instruction," *Journal of Aerosol Medicine*, vol. 16, No. 2, 2003, 131-141.

Taube et al., "Use of a portable device to record maximum inspiratory flow in relation to dyspnea in patients with COPD," *Respiratory Medicine*, 2011, 105, 316-312.

(56)     References Cited

OTHER PUBLICATIONS

Steller, "Microcontroller Based Diagnostic Smart Inhaler," University of Cincinnati, Dec. 7, 2014, 63 pages.
Azzopardi B.J., "Sauter Mean Diameter," Thermopedia, Internet Archive Wayback Machine, Sep. 30, 2012-May 27, 2013, 4 Pages, XP002724921, [Retrieved on May 23, 2014], Retrieved from URL: https://web.archive.Org/web/20120930225842/ http://www.termopedia. com/content/1108.
Extended European Search Report for European Application No. 20832150.5, dated Jun. 21, 2023, 10 Pages.
International Preliminary Report on Patentability for International Application No. PCT/US2020/040132, dated Jan. 6, 2022, 12 Pages.
International Search Report and Written Opinion for International Application No. PCT/US2020/040132, dated Sep. 30, 2020, 14 Pages.
Office Action for Chinese Application No. 202080053526.X, dated Apr. 24, 2025, 18 pages.

* cited by examiner

DELIVERY OF SMALL DROPLETS TO THE RESPIRATORY SYSTEM VIA ELECTRONIC BREATH ACTUATED DROPLET DELIVERY DEVICE

RELATED APPLICATIONS

This application is a U.S. national phase application under 35 U.S.C. § 371 of International Application No. PCT/US2020/040132, filed on Jun. 29, 2020, entitled "DELIVERY OF SMALL DROPLETS TO THE RESPIRATORY SYSTEM VIA ELECTRONIC BREATH ACTUATED DROPLET DELIVERY DEVICE," which claims benefit under 35 U.S.C. § 119 of U.S. Provisional Patent Application No. 62/867,719, filed Jun. 27, 2019, entitled "DELIVERY OF SMALL DROPLETS TO THE PULMONARY SYSTEM VIA ELECTRONIC BREATH ACTUATED DROPLET DELIVERY DEVICE", U.S. Provisional Patent Application No. 62/883,028, filed Aug. 5, 2019, entitled "DELIVERY OF SMALL DROPLETS TO THE PULMONARY SYSTEM VIA ELECTRONIC BREATH ACTUATED DROPLET DELIVERY DEVICE", U.S. Provisional Patent Application No. 63/001,225, filed Mar. 27, 2020, entitled "DELIVERY OF SMALL DROPLETS TO THE PULMONARY SYSTEM VIA ELECTRONIC BREATH ACTUATED DROPLET DELIVERY DEVICE", the contents of which are each herein incorporated by reference in their entireties.

FIELD OF THE INVENTION

This disclosure relates to the delivery of small droplets to the respiratory via a droplet delivery device, and more specifically via an electronic droplet delivery device.

BACKGROUND OF THE INVENTION

The use of droplet generating devices for the delivery of substances to the respiratory system is an area of large interest. A major challenge is providing a device that delivers an accurate, consistent, and verifiable amount of substance, with a droplet size that is suitable for successful delivery of substance to the targeted area of the respiratory system.

Currently most inhaler type systems, such as metered dose inhalers (MDI), pressurized metered dose inhalers (p-MDI), or pneumatic and ultrasonic-driven devices, generally produce droplets with high velocities and a wide range of droplet sizes including large droplets that have high momentum and kinetic energy. Droplet plumes with large size distributions and high momentum do not reach a targeted area in the respiratory system, but rather are deposited throughout the pulmonary passageways, mouth and throat. Such non-targeted deposition may be undesirable for many reasons, including improper dosing and unwanted side effects.

Droplet plumes generated from current droplet delivery systems, as a result of their high ejection velocities and the rapid expansion of the substance carrying propellant, may also lead to localized cooling and subsequent condensation, deposition and crystallization of substance onto device surfaces. Blockage of device surfaces by deposited substance residue is also problematic.

Accordingly, there is a need for a droplet delivery device that delivers droplets of a suitable size range, avoids surface fluid deposition and blockage of apertures, and in an amount that is consistent and reproducible.

SUMMARY OF THE INVENTION

One aspect of the disclosure relates to an ejector mechanism comprising a piezoelectric actuator and an aperture plate. In certain embodiments, the aperture plate has a plurality of openings formed through its thickness and at least the fluid entrance side of one or more of said plurality of openings configured so as to provide a surface contact angle of less than 90 degree. In certain embodiments, the piezoelectric actuator is operable to oscillate the aperture plate at a frequency to thereby generate an ejected stream of droplets such that at least about 50% of the droplets have an average ejected droplet diameter of less than about 6 microns during use.

In some embodiments, at least a portion of the interior of at least one of the openings is configured so as to provide a surface contact angle of less than 90 degree. In other embodiments, the aperture plate is configured such that at least the fluid exit side of one or more of said plurality of openings is configured to provide a surface contact angle of greater than 90 degrees.

In certain aspects, the surface contact angle of less than 90 degree at the fluid entrance side of one or more of said plurality of openings is obtained by surface coating with a hydrophilic material, surface structural modification, or a combination thereof. In other embodiments, the surface contact angle of greater than 90 degrees at the fluid exit side of one or more of said plurality of openings is obtained by surface coating with a hydrophobic polymer.

In certain aspects, the aperture plate is composed of a material selected from the group consisting of poly ether ether ketone (PEEK), polyimide, polyetherimide, polyvinylidine fluoride (PVDF), ultra-high molecular weight polyethylene (UHMWPE), nickel, nickel-cobalt, nickel-palladium, palladium, platinum, metal alloys thereof, and combinations thereof.

Other aspects of the disclosure relate to an electronically actuated droplet delivery device for delivering a fluid composition as an ejected stream of droplets to the respiratory system of a subject. In some embodiments, the device comprises a housing; a mouthpiece positioned at an airflow exit of the device; a reservoir disposed within or in fluid communication with the housing for receiving a fluid composition; an ejector mechanism of the disclosure, in fluid communication with the reservoir and configured to generate the ejected stream of droplets; and at least one differential pressure sensor positioned within the housing, the at least one differential pressure sensor configured to activate the ejector mechanism upon sensing a pre-determined pressure change within the device to thereby generate the ejected stream of droplets. In certain embodiments, the ejector mechanism is configured to generate the ejected stream of droplets wherein at least about 50% of the droplets have an average ejected droplet diameter of less than about 6 microns, such that at least about 50% of the mass of the ejected stream of droplets is delivered in a respirable range to the respiratory system of the subject during use.

In yet other aspects, a method for delivering an agent as an ejected stream of droplets in a respirable range to the respiratory system of a user is provided. In certain embodiments, the method comprises (a) generating an ejected stream of droplets via a droplet delivery device of the disclosure, wherein at least portion (e.g., at least about 50%) of the ejected stream of droplets have an average ejected droplet diameter of less than about 6 μm; and (b) delivering the ejected stream of droplets to the respiratory system of the subject such that at least a portion (e.g., at least about 50%) of the mass of the ejected stream of droplets is delivered in a respirable range to the respiratory system of a subject during use.

While multiple embodiments are disclosed, still other embodiments of the present disclosure will become apparent to those skilled in the art from the following detailed description, which shows and describes illustrative embodiments of the disclosure. As will be realized, the invention is capable of modifications in various aspects, all without departing from the spirit and scope of the present disclosure. Accordingly, the detailed descriptions are to be regarded as illustrative in nature and not restrictive.

DESCRIPTION OF THE DRAWINGS

FIG. 8A illustrates an embodiment wherein the ejector mechanism comprises a piezoelectric actuator and an ultrasonic horn. FIG. 8B illustrates an embodiment wherein the ejector mechanism is generally perpendicular to the direction of air flow through the device. FIG. 8C illustrates and embodiment wherein the ejector mechanism is orientated at an angle with reference to the direction of air flow through the device.

FIG. 9A shows the mouthpiece, fluid cartridge and body housing as separate elements. FIG. 9B shows the fluid cartridge interfaced with the mouthpiece to form a combined mouthpiece/fluid cartridge, with the body housing as a separate element. FIG. 9C shows the device fully assembled, with the mouthpiece/fluid cartridge secured to the body housing.

Figures 1A, 1B, 1C, 1D:
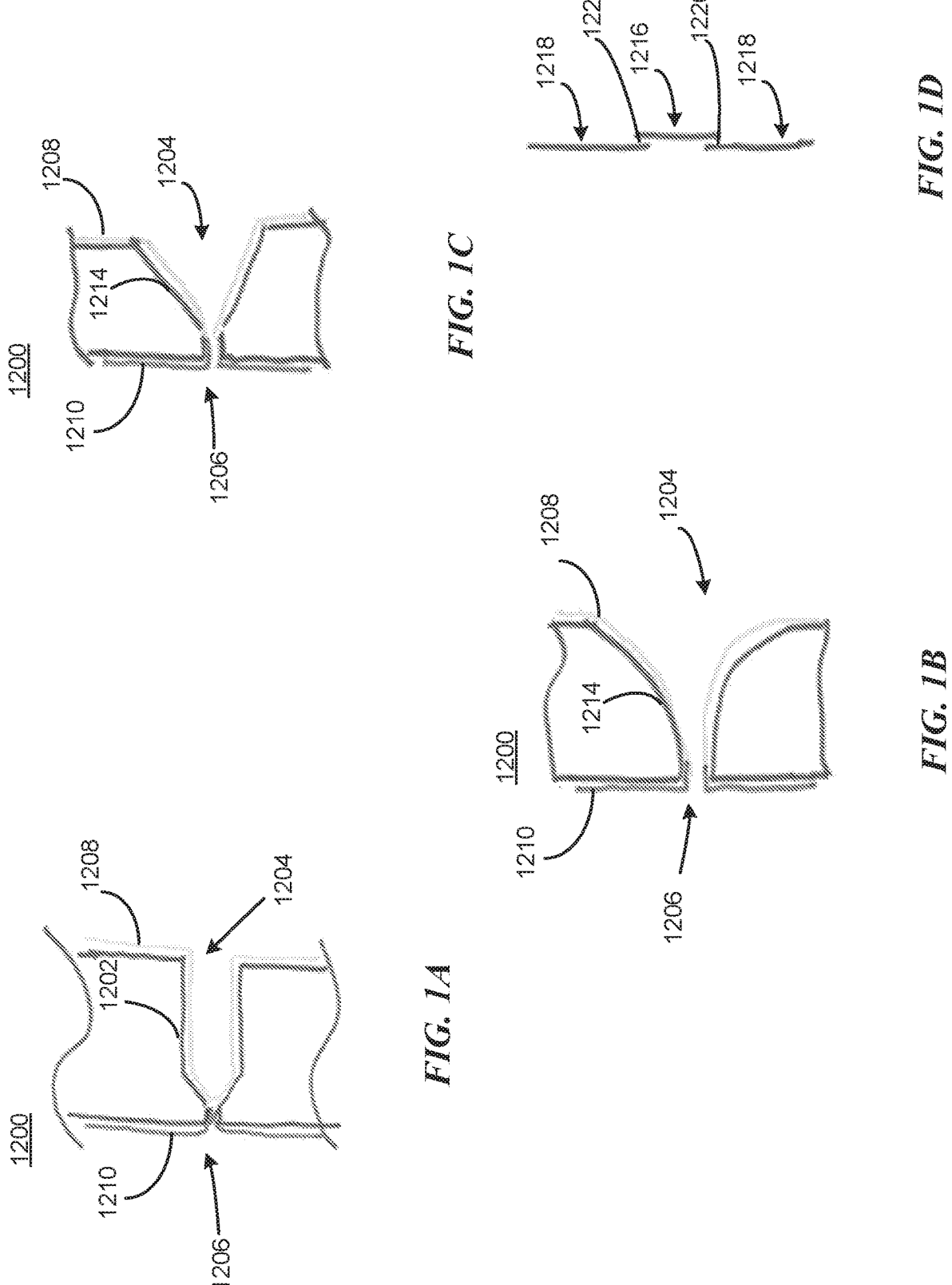
FIG. 1A-1C illustrate cross-sections of an exemplary opening configured to provide a desired surface tension, with FIG. 1A showing an embodiment with a structural well between the fluid entrance side and the fluid exit side, FIG. 1B showing a linear taper between the fluid entrance side and the fluid exit side, and FIG. 1C showing a curved taper between the fluid entrance side and the fluid exit side, in accordance with embodiments of the disclosure.
FIG. 1D illustrates a cross-section of an exemplary aperture plate and annulus ring configuration, in accordance with an embodiment of the disclosure.

The foregoing and other objects, features, and advantages of the present disclosure set forth herein will be apparent from the following description of particular embodiments of those inventive concepts, as illustrated in the accompanying drawings. Also, in the drawings the like reference characters refer to the same parts throughout the different views. The drawings depict only typical embodiments of the present disclosure and, therefore, are not to be considered limiting in scope.

DETAILED DESCRIPTION

Effective and efficient delivery of substances using respiratory droplet delivery devices to the desired areas of the respiratory system, and the synchronization of the administration of droplets with the inspiration/expiration cycle using such devices has always posed a problem. For instance, optimum deposition in alveolar airways generally requires droplets with aerodynamic diameters in the ranges of 1 to 6 μm, with droplets below about 4 μm shown to more effectively reach the alveolar region of the lungs and larger droplets above about 6 μm shown to typically deposited on the tongue or strike the throat and coat the bronchial passages. Smaller droplets, for example less than about 1 μm, penetrate more deeply into the lungs and have a tendency to be exhaled. As such, design of droplet delivery devices for respiratory use requires the ability to precisely target droplet sizes for a particular use.

In certain aspects, the disclosure relates to an ejector mechanism for use in a droplet delivery device for administering fluids to the respiratory system of a user with precise droplet size. In certain embodiments, the ejector mechanism may comprise at least one aperture plate with a plurality of openings formed through its thickness for ejecting droplets, wherein at least one surface of the aperture plate is configured to provide a desired surface contact angle. In certain embodiments, the ejector mechanism may be an electronically actuated ejector mechanism and may further comprise a piezoelectric actuator configured to vibrate the aperture plate during use to thereby generate a stream of droplets. One aspect of the disclosure relates to an ejector mechanism comprising a piezoelectric actuator and an aperture plate.

In certain embodiments, the aperture plate has a plurality of openings formed through its thickness and at least the fluid entrance side of one or more of said plurality of openings configured so as to provide a surface contact angle of less than 90 degree. In certain embodiments, the piezoelectric actuator is operable to oscillate the aperture plate at a frequency to thereby generate an ejected stream of droplets such that at least about 50% of the droplets have an average ejected droplet diameter of less than about 6 microns during use. In some embodiments, at least a portion of the interior of at least one of the openings near the fluid entrance side is configured so as to provide a surface contact angle of less than 90 degree.

In other embodiments, the aperture plate is configured such that at least the fluid exit side of one or more of said plurality of openings is configured to provide a surface contact angle of greater than 90 degrees. In some embodiments, at least a portion of the interior of at least one of the openings near the fluid exit side is configured so as to provide a surface contact angle of greater than 90 degrees.

In certain embodiments, at least the fluid entrance surface of one or more openings of the aperture plate and the fluid exit surface of one or more openings of the aperture plate are configured (e.g., treated, coated, surface modified, or a combination thereof) to provide a desired surface contact angle. In some embodiments, at least a portion of the interior of at least one of the openings near the fluid entrance side is configured so as to provide a desired surface contact angle. By way of example, the fluid entrance surface and/or interior surface of one or more openings of the aperture plate may be configured to have a surface contact angle of less than about 80 degrees, less than about 70 degrees, less than about 50 degrees, less than about 55 degrees, less than about 50 degrees, less than about 40 degrees, less than about 35 degrees, less than about 30 degrees, less than about 20 degrees, less than about 10 degrees, between about 10 degrees and about 80 degrees, between about 10 degrees and about 60 degrees, between about 20 degrees and about 55 degrees, between about 10 and about 35 degrees, between about 15 and about 35 degrees, etc.

In certain embodiments, the fluid exit surface of one or more openings of the aperture plate may be configured (e.g., treated, coated, surface modified, or a combination thereof) to provide a desired surface contact angle. In some embodiments, at least a portion of the interior of at least one of the openings near the fluid exit side is configured so as to provide a desired surface contact angle. By way of example, the fluid exit surface and/or interior surface of one or more openings of the aperture plate may be configured to have a surface contact angle of greater than greater than 90 degrees, between 90 degrees and 140 degrees, between 90 degrees and 135 degrees, between 100 degrees and 140 degrees, between 100 degrees and 135 degrees, between 90 degrees and 110 degrees, etc.

In certain aspects, the ejector mechanism of the disclosure is capable of delivering a defined volume of fluid (fixed dose) in the form of an ejected stream of droplets having a small average ejected diameter such that an adequate and repeatable high percentage of the droplets are delivered into the desired location within the airways, e.g., the alveolar airways of the subject during use. In certain embodiments, the average droplet diameters may range from about 0.7 μm to about 5 μm, about 0.7 μm to about 4.7 μm, about 0.7 μm to about 4 μm, about 0.7 μm to about 2.5 μm, about 0.7 μm to about 1.3 μm, etc.

In other aspects, the present disclosure provides a droplet delivery device for delivery of a fluid as an ejected stream of small droplets to the respiratory system of a subject, the device comprising a housing, a reservoir for receiving a volume of fluid, and an ejector mechanism including a piezoelectric actuator and an aperture plate having a desired surface contact angle on at least the fluid entrance side thereof and optionally a desired surface contact angle on a fluid exit surface thereof, wherein the ejector mechanism is configured to eject a stream of droplets having an average ejected droplet diameter of less than about 4 microns, less than about 3 microns, less than about 2 microns, less than about 1.5 microns, less than about 1 microns, etc.

As discussed herein, in certain aspects, the droplet delivery device may include an ejector mechanism having an aperture plate wherein at least one surface is configured with a desired surface contact angle to facilitate generation of droplets with the desired droplet size distribution, e.g., less than 4 μm, less than about 3 microns, less than about 2 microns, less than about 1.5 microns, less than about 1 microns, etc. In certain embodiments, the aperture plate is configured at least at the fluid entrance side, and optionally at the fluid exit surface. In certain embodiments, at least a portion of the interior surface of one or more openings may be configured with a desired surface contact angle.

In certain embodiments, one or more surfaces of the aperture plate may be modified, treated, coated, or a combination thereof to achieve the desired surface contact angle. In certain aspects, the one or more surfaces of the aperture plate may be modified, treated, coated, or a combination thereof so as to affect surface hydrophobicity. By way of examples, one or more surfaces of the aperture plate may be modified, treated, coated, or a combination thereof so as to result in at least one more hydrophilic surface on the aperture plate, at least one more hydrophobic surface on the aperture plate, or a combination thereof.

Without intending to be limited by theory, the surface contact angles described herein are believed to more effectively attract an aqueous composition into the openings of the ejector aperture plate during the vibration of the aperture plate by the piezo element, thereby increasing the mass flow of aerosol droplets out of the aperture plate.

In addition to aperture plate surface contact angle, several features of the ejector mechanism allow for precise dosing of specific droplet sizes. For instance, droplet size is set, in part, by the diameter of the openings in the aperture plate, which are formed with high accuracy. By way of example, the openings in the aperture plate at the fluid exit side of the aperture plate may range in size from 1 μm to 6 μm, from 2 μm to 5 μm, from 3 μm to 5 μm, from 3 μm to 4 μm, etc. In certain embodiments, the aperture plate may include openings having different cross-sectional shapes or diameters to thereby provide ejected droplets having different average ejected droplet diameters. Ejector rate also influences droplet size. Ejection rate, in droplets per second, is fixed by the frequency of the aperture plate vibration, e.g., 108-kHz, etc.

In certain aspects of the disclosure, desired surface contact angles may be formed by creating hydrophilic surfaces, e.g., through treating, coating, surface modifying, or a combination thereof. A surface is considered to be hydrophilic when that angle is less than about 80 degrees, about 70 degrees, about 60 degrees, about 55 degrees, about 50 degrees, etc., and may be considered to be super hydrophilic when that angle is less than about 10 to 20 degrees (droplet tends to spread out across the surface). The strength of the hydrophilic effect may be measured by the angle between the edge of a droplet of water and the surface of the aperture plate.

By way of example, the aperture plate can formed of a metal, e.g., stainless steel, nickel, cobalt, titanium, iridium, platinum, or palladium or alloys thereof, and configured to achieve the desired contact angles as described herein. Alternatively, the aperture plate can be formed of suitable polymeric material, and be configured to achieve the desired surface contact angles, as described herein. By way of example, the aperture plate may be composed of a material selected from the group consisting of poly ether ether ketone (PEEK), polyimide, polyetherimide, polyvinylidine fluoride (PVDF), ultra-high molecular weight polyethylene (UHMWPE), nickel, nickel-cobalt, nickel-palladium, palladium, platinum, metal alloys thereof, and combinations thereof. Further, in certain aspects, the aperture plate may comprise a domed shape.

By way of example, the desired surface contact angle may be created on a surface of an aperture plate by increasing the surface energy through creation of a polar surface. Exemplary methods to increase surface energy comprise forming an oxide surface on a metallic ejector aperture plate which is polar. In accordance with aspects of the disclosure, exemplary methods for creating a hydrophilic surface contact angle on an aperture plate including dip coating methods, etching methods, and chemical deposition methods. Dip coating methods comprise dipping the aperture plate into a solution comprising a desired coating and a solvent, which solution will form a hydrophilic coating on the surface when the solvent evaporates. Chemical deposition methods include known deposition methods, e.g., plasma etch, plasma coating, plasma deposition, CVD, electroless plating, electroplating, etc., wherein the chemical deposition uses a plasma or vapor to open the bonds on the surface of the aperture plate so that oxygen or hydroxyl molecules attach to the surface rendering it polar. Etching methods include non-chemical etching methods using surface roughening.

In certain embodiments, any deposited hydrophilic layer is significantly thinner than the opening size such that it does not impact the size of the generated droplets. In certain embodiments, the surface treatment may extend into at least a portion of one or more openings of the aperture plate so as to form a hydrophilic surface within at least a portion of one or more openings.

In certain embodiments, the desired surface contact angle may be obtained through surface roughening achieved, e.g., via non-chemical etching. Without intending to be limited by theory, as an approximation, the Wenzel Contact Angle equation, "Apparent Contact Angles on Rough Surfaces. The Wenzel Contact Angle Revisited", Wolansky and Marmur, Colloids and Surfaces A, 156 (1999) pp. 381-388, may be used to estimate surface contact angle. The Wenzel equation yields contact angles for liquid drops on rough surfaces. It assumes no hysteresis in the contact angle, and this is an approximation.

In certain embodiments, the aperture plate may optionally be surface sputtered with a thin layer (e.g., about 30 to about 150 nm, about 60 nm to about 100 nm, about 30 nm, about 60 nm, about 80 nm, about 100 nm, etc. thick sputtering) of a precious metal, such as gold (Au), palladium (Pd), platinum (Pt), silver (Ag) and precious metal alloys. In certain embodiments, the surface may be sputtered with a thin layer of palladium. The precious metal layer may then be etched at varying etch powers, e.g., low, medium or high etching power to provide a desired surface contact angle. To provide the desired contact angle, the etch may be performed once, twice, three times, four times, etc.

In other embodiments, the aperture plate may be coated on at least the fluid entrance side of the aperture plate with a hydrophilic polymer to achieve the desired surface contact angle. In yet other embodiments, the aperture plate may be coated on at least a portion of the interior surface of one or more openings, within the entire interior surface of one or more openings, on both the fluid entrance side and the fluid ejection surface of the aperture plate, and combinations thereof. Any known hydrophilic polymer suitable for use in medical applications may be used.

Any suitable hydrophilic coating to achieve the desired surface contact angle on the fluid entrance side of the ejector aperture plate may be used. Exemplary hydrophilic coating materials include, but are not limited to siloxane based coatings, isocyante based coatings, ethylene oxide based coatings, polyisocyanate based coatings, hydrocyclosiloxane based coatings, hydroxyalkylmethacrylate based coatings, hydroxyallkylacrylate based coatings, glycidylmethacrylate based coatings, propylene oxide based coatings, N-vinyl-2-pyrrolidone based coatings, latex based coatings, polyvinylchloride based coatings, polyurethane based coatings, etc.

By way of non-limiting example, a suitable hydrophilic coating may comprise a single layer hydrophilic surface formed by a process of cleaning the intended surface with a low pressure plasma and then dipping the surface into a solution of organophosphorous acids which self-assemble into a polar monolayer (e.g., see Aculon U.S. Pat. No. 8,658,258A, which is incorporated herein by reference). These layers are typically less than 10 nm thick, which is significantly less than a micron-sized hole. Contact angles as low as 10 degrees can be achieved using such coatings.

In other embodiments, the aperture plate may optionally be coated on the fluid exit side with a hydrophobic coating. Any known hydrophobic polymer suitable for use in medical applications may be used, e.g., polytetrafluoroethylene (Teflon), siloxane based coatings, paraffin, polyisobutylene, etc. The surface of the hydrophobic coating may be chemically or structurally modified or treated to further enhance or control the surface contact angle, as desired.

In certain embodiments, the aperture plate may be coated with a siloxane based coating to provide an initial hydrophobic coating, which siloxane based coating is thereafter masked or shielded in a suitable manner on the fluid exit side. Following masking, the masked aperture plate may thereafter be exposed to an oxidizing treatment to render the siloxane coating hydrophilic on the exposed (unmasked) portions thereof, i.e., the fluid entrance sides. In this manner, in certain embodiments of the disclosure, the same siloxane based coating may provide both hydrophilic and hydrophobic coatings to surfaces of the aperture plate. By way of example, such siloxane coatings may be selected from siloxanes known for use in medical applications, such as 2,4,6,8-Tetramethylcyclotetrasiloxane, or 1,1,3,3-Tetramethyldisiloxane.

The aperture plate may be metallic or polymer with openings about the diameter of the desired droplets (as discussed further herein). By way of non-limiting example, the aperture plate may be formed from silicon, silicon carbide, nickel palladium, or a high stiffness polymer such as polyether ether ketone (PEEK), poly-amide, Kapton or Ultra High Molecular Weight Polyethylene (UHMPWE). When using a polymer aperture plate, the openings may be produced by rolling, stamping, laser ablation, bulk etching or other known micro-machining processes. When using silicon and SiC for the aperture plate, the openings may be formed using typical semiconductor processes. Without being limited, these silicon materials can be formed by bulk micro-machining processes, such as wet etching. In addition, the aperture plate opening area may be formed to have a dome-like shape to increase the stiffness of the aperture plate and to creating uniform ejection accelerations.

The aperture plate may have an array of opening ranging from, e.g., 100 to 10,000 openings, 500 to 10,000 openings, etc. The openings may generally have a fluid exit side diameter similar to that of the desired droplets, e.g., of 0.5 μm to 100 μm diameter, 1 μm to 20 μm, 1 μm to 10 μm, 1 μm to 5 μm, 1 μm to 4 μm, etc., as described further herein. The fluid entrance side diameter may range from between about 30 μm to 300 μm, about 75 μm to about 200 μm, about 100 μm to about 200 μm, etc. Aperture plates may be formed to have a thickness of between about 100 μm to about 925 μm, between about 100 μm and about 300 μm.

As described above, the aperture plate may include various treatments, coatings surface modifications, or combinations thereof, on one or more surfaces thereof. For example, in certain embodiments, the aperture plate may include various combinations of: a hydrophilic coating on one or more surfaces, an optional hydrophobic coating on one or more surfaces, native surfaces, surface etchings, etc. In one embodiment, the aperture plate may be non-chemically etched on the fluid entrance side of the aperture plate (fluid reservoir facing side), with etching, a hydrophobic coating, or no treatment on the fluid exit side. In another embodiment, the aperture plate may include a hydrophilic coating on at least the fluid entrance side of the aperture plate (fluid reservoir facing side), a hydrophilic coating within at least a portion of the interior of one or more openings, or combinations thereof. In other embodiments, the aperture plate may include a hydrophobic coating on the droplet exit side of the aperture plate—alone or in combination with one or more hydrophilic coatings. A gas or liquid process may be used to form the hydrophobic and hydrophilic surfaces. For example, hydrophilic and hydrophobic surfaces can be formed using liquid coating, sputtering, CVD, plasma deposition, ion implantation, etc.

FIG. 1A shows a cross-section of an exemplary surface treated opening 1200 of an aperture plate in accordance with an embodiment of the disclosure. As shown, the opening 1200 is configured to have a structural well 1202 extending through the aperture plate thickness from the fluid entrance side 1204 to the fluid exit side 1206. As shown, the opening 1200 may be surface treated on the fluid entrance side 1204 to be hydrophilic 1208 (contact angle between about 2 and about 80 degrees, between about 2 and about 60 degrees, between about 2 and about 40 degrees, between about 5 and about 40 degrees, between about 5 and about 20 degrees, between about 5 and about 10 degrees, etc.). In certain embodiments, the fluid exit side 1206 may optionally be treated to be hydrophobic 1210 (contact angle between about 80 and about 160 degrees, between about 80 and about 130 degrees, etc.). In the illustrated embodiment, the hydrophilic 1208 surfaces and hydrophobic 1210 are also formed on at least some of the interior surfaces within the structural well 1202. Without intending to be limited, such hydrophobic treatments may act to minimize "weeping" of fluid from the aperture plate openings during use.

FIG. 1B and FIG. 1C illustrate similar surface treated openings 1200, except the opening 1200 is configured to taper 1214 from the fluid entrance side 1204 to the fluid exit side 1206 (rather than having a structural well). FIG. 1B illustrates a linear taper, while FIG. 1C illustrates a curved taper. Without intending to be limited by theory, because the fluid entrance region tapers to a smaller diameter near the fluid exit side 1206, the fluid entrance side 1204 is treated to be hydrophilic 1208 (e.g., contact angle of 2 to 80 degrees) to facilitate fluid reaching the ejection openings by capillary action. In certain aspects, the liner versus curved taper is generally a result of fabrication technique and, to some degree, on the need for specific properties such as dispensing a fluid of higher or lower viscosity or the need to preserve material to maximize the stiffness of the aperture plate against flexure or a resonant point that is too low.

FIG. 1D illustrates an aperture plate 1216 (e.g., palladium-nickel) supported by a stainless steel annulus 1218. The aperture plate is welded or bonded 1220 to the stainless steel annulus, thereby allowing a thicker support material which is much less expensive than aperture plate material, e.g., palladium-nickel. Again hydrophilic and hydrophobic surface treatments may be used on both the fluid entrance side and the droplet exit side of the aperture plate and support structure.

The aperture plates, structural wells, and tapers may be produced, e.g., by semiconductor techniques, stamping, rolling or laser ablation. Rolling may be preferred because more precise forming pressures are possible and continuous production for material from rolls allows lower-cost manufacturing. Because the material stiffness of polymers (especially the UHMWPE) is lower than metals such as stainless steel or palladium-nickel, ribs on the fluid or air side of the aperture plate may also be formed at the time of rolling or prior to laser ablation. Similarly, a metallic annulus may be used to stiffen the edge of the aperture plate against flexure. In addition, the aperture plate area can be formed to have a dome-like shape to increase the stiffness of the aperture plate and creating uniform ejection accelerations.

In certain aspects, the aperture plate may be bonded to the reservoir or fluid cartridge. Further, if desired, the aperture plate may be bonded to an intermediary structural material like a stainless steel annulus to reduce costs by minimizing the ejector plate, or to increase the aperture plate stiffness or to facilitate attachment to the cartridge. With polymer materials, the aperture plate may have raised ribs at intervals to stiffen the aperture plate against flexure. Ribs can be produced by rolling or stamping in a polymer heated above its transition temperature.

In specific embodiments, the ejector mechanism is electronically breath activated by at least one differential pressure sensor located within the housing of the droplet delivery device upon sensing a pre-determined pressure change within the housing. In certain embodiments, such a pre-determined pressure change may be sensed during an inspiration cycle by a user of the device, as will be explained in further detail herein.

In accordance with certain aspects of the disclosure, effective deposition into the lungs generally requires droplets less than about 5-6 μm in diameter. Without intending to be limited by theory, to deliver fluid to the lungs a droplet delivery device must impart a momentum that is sufficiently high to permit ejection out of the device, but sufficiently low to prevent deposition on the tongue or in the back of the throat. Droplets below approximately 5-6 μm in diameter are transported almost completely by motion of the airstream and entrained air that carry them and not by their own momentum.

In some aspects, the disclosure provides devices and methods for delivering small droplets to the respiratory system of a user with minimal or no mouth or throat irritation. The breath actuated droplet delivery devices of the disclosure may be configured so as to be actuated to eject droplets into the airstream at precise times during a user's inspiration cycle to as to maximize delivery into the respiratory system, while minimizing or eliminating mouth or throat irritation. Without intending to be limited by theory, as described herein, the small droplets generated via the devices of the disclosure are transported almost completely by motion of airstream and entrained air. Using this entrained motion and tuned droplet size, the ejection of droplets may be focused so as to eject during peak flow of the inspiration cycle so as to optimize inhalation into the target site in the respiratory system (e.g., deep lungs), while minimizing inadvertent delivery to non-desired sites in the respiratory system (e.g., mouth and throat).

In one embodiment, the device may be configured to provide for ejection of droplets after a breath initiation period, e.g., 0.1-0.5 seconds. The device may be configured to sense the initiation of the inspiration cycles, allowing a short period of time, e.g., 0.1-0.5 seconds as to form a steady inspiration flow. Once the device senses a steady inspiration flow, the device may activate the ejector mechanism to initiate ejection of the small droplets for inhalation into the target site of the respiratory system. Optionally, the device may control the ejector mechanism to discontinue generation of droplets at a specified end portion of the inspiration cycle, so as to allow for complete inhalation of the droplets to the target site of the respiratory system. Such a device provides for an improved method of delivering droplets to the respiratory system of a user with minimal or no mouth or throat irritation.

In certain aspects, the present disclosure includes and provides an ejector mechanism configured to eject a stream of small droplets within the respirable range of less than about 4 μm, less than about 3 microns, less than about 2 microns, less than about 1.5 microns, less than about 1 microns, etc. The ejector mechanism is comprised of an aperture plate having a desired surface contact angle at least at the fluid entrance side thereof and optionally a desired surface contact angle on at least the fluid exit surface thereof, wherein the aperture plate is directly or indirectly coupled to a piezoelectric actuator.

In certain implementations, the aperture plate may be coupled to an actuator plate that is coupled to the piezoelectric actuator. The aperture plate generally includes a plurality of openings formed through its thickness and the piezoelectric actuator directly or indirectly (e.g. via an actuator plate) oscillates the aperture plate, having fluid in contact with one surface of the aperture plate, at a frequency and voltage to generate a directed aerosol stream of droplets through the openings of the aperture plate into the lungs, as the patient inhales. In other implementations where the aperture plate is coupled to the actuator plate, the actuator plate is oscillated by the piezoelectric oscillator at a frequency and voltage to generate a directed aerosol stream or plume of aerosol droplets.

In certain aspects, the present disclosure relates to a droplet delivery device for delivering a fluid as an ejected stream of small droplets to the respiratory system of a subject. In certain aspects, the agents may be delivered at a high dose concentration and efficacy, as compared to alternative dosing routes and standard inhalation technologies.

As discussed above, effective delivery of droplets deep into the lung airways require droplets that are less than about 5-6 microns in diameter, specifically droplets with mass mean aerodynamic diameters (MMAD) that are less than about 5 microns. However, for certain agents and uses, droplets about 1 μm or smaller for quick adsorption in the deep lung may be desirable, e.g., it may be desired to utilize droplets less than 4 μm, less than 2 μm, and less than 1 μm for the delivery of nicotine and related substances to the deep lungs.

The mass mean aerodynamic diameter is defined as the diameter at which 50% of the droplets by mass are larger and 50% are smaller. In certain aspects of the disclosure, in order to deposit in the alveolar airways, droplets in this size range must have momentum that is sufficiently high to permit ejection out of the device, but sufficiently low to overcome deposition onto the tongue (soft palate) or pharynx.

In other aspects of the disclosure, methods for generating an ejected stream of small droplets for delivery to the respiratory system of user using the droplet delivery devices of the disclosure are provided. In certain embodiments, the ejected stream of droplets is generated in a controllable and defined droplet size range. By way of example, the droplet size range includes at least about 50%, at least about 60%, at least about 70%, at least about 85%, at least about 90%, between about 50% and about 90%, between about 60% and about 90%, between about 70% and about 90%, etc., of the ejected droplets are in the respirable range of below about 4 μm, below about 3 μm, below about 2.5 μm, below about 2 μm, between about 0.7 μm and about 4 μm, between about 0.7 μm and about 3 μm, between about 0.7 μm and about 2.5 μm, between about 0.7 μm and about 2.0 μm, between about 0.7 μm and about 1.5 μm, between about 0.7 μm and about 1.0 μm, etc.

In other embodiments, the ejected stream of droplets may have one or more diameters, such that droplets having multiple diameters are generated so as to target multiple regions in the airways (mouth, tongue, throat, upper airways, lower airways, deep lung, etc.) By way of example, droplet diameters may range from about 0.7 μm to about 200 μm, about 0.7 μm to about 100 μm, about 0.7 μm to about 60 μm, about 0.7 μm to about 40 μm, about 0.7 μm to about 20 μm, about 0.7 μm to about 5 μm, about 0.7 μm to about 4.7 μm, about 0.7 μm to about 4 μm, about 0.7 μm to about 3.0 μm, about 0.7 μm to about 2.5 μm, about 0.7 μm and about 2.0 μm, about 0.7 μm and about 1.5 μm, about 0.7 μm and about 1.0 μm, about 5 μm to about 20 μm, about 5 μm to about 10 μm, and combinations thereof. In particular embodiments, at least a fraction of the droplets have diameters in the respirable range, while other droplets may have diameters in other sizes so as to target non-respirable locations larger than about 5 μm). Illustrative ejected droplet streams in this regard might have 50%-70% of droplets in the respirable range (less than about 5 μm), and 30%-50% outside of the respirable range (about 5 μm-about 10 μm, about 5 μm-about 20 μm, etc.)

In another embodiment, methods for delivering safe, suitable, and repeatable dosages of an agent to the respiratory system of a user using the droplet delivery devices of the disclosure are provided. The methods deliver an ejected stream of droplets to the desired location within the respiratory system of the user.

In certain aspects of the disclosure, a droplet delivery device for delivering an ejected stream of small droplets to the respiratory system of a user is provided. The droplet delivery device generally includes a housing and a reservoir disposed in or in fluid communication with the housing, an ejector mechanism in fluid communication with the reservoir, and at least one differential pressure sensor positioned within the device. The differential pressure sensor is configured to electronically breath activate the ejector mechanism upon sensing a pre-determined pressure change within the device, and the ejector mechanism is configured to generate a controllable plume of an ejected stream of small droplets. The ejector mechanism may include a piezoelectric actuator, which is directly or indirectly coupled to an aperture plate having a plurality of openings formed through its thickness and exhibiting a desired surface contact angle at least at the fluid entrance side thereof, and an optional a desired surface contact angle at the fluid exit surface thereof (e.g., at the fluid entrance side, at the fluid exit side, within at least a portion of one or more openings, or combinations thereof). The piezoelectric actuator is operable to directly or indirectly oscillate the aperture plate at a frequency to thereby generate an ejected stream of droplets.

In accordance with the disclosure, any suitable droplet deliver device may be used in connection with the ejector mechanisms of the disclosure. By way of example, the ejector mechanism of the disclosure may be used with the droplet delivery devices disclosed in co-owned PCT applications WO 2017/192767, WO 2019/071008; and PCT/US2020/032383, the contents of which are herein incorporated by reference in their entireties.

By way of non-limiting example, in certain embodiments, the droplet delivery device may generally include a housing and a reservoir disposed in or in fluid communication with the housing, an ejector mechanism in fluid communication with the reservoir, and at least one differential pressure sensor positioned within the housing. The differential pressure sensor is configured to electronically breath activate the ejector mechanism upon sensing a pre-determined pressure change within the housing, and the ejector mechanism is configured to generate a controllable plume of an ejected stream of droplets. The ejected stream of droplets is formed from low surface tension compositions, particularly compositions comprising agents that are insoluble or sparingly soluble in water. The ejector mechanism comprises a piezoelectric actuator which is directly or indirectly coupled to an aperture plate of the disclosure. The piezoelectric actuator is operable to directly or indirectly oscillate the aperture plate at a frequency to thereby generate an ejected stream of droplets.

In certain embodiments, the droplet delivery device may be configured in an in-line orientation in that the housing, ejector mechanism and related electronic components are orientated in a generally in-line or parallel configuration so as to form a small, hand-held device.

In certain embodiments, the droplet delivery device may include a combination reservoir/ejector mechanism module that may be replaceable or disposable either on a periodic basis, e.g., a daily, weekly, monthly, as-needed, etc. basis, as may be suitable for a prescription or over-the-counter medication.

Figures 2A, 2B:
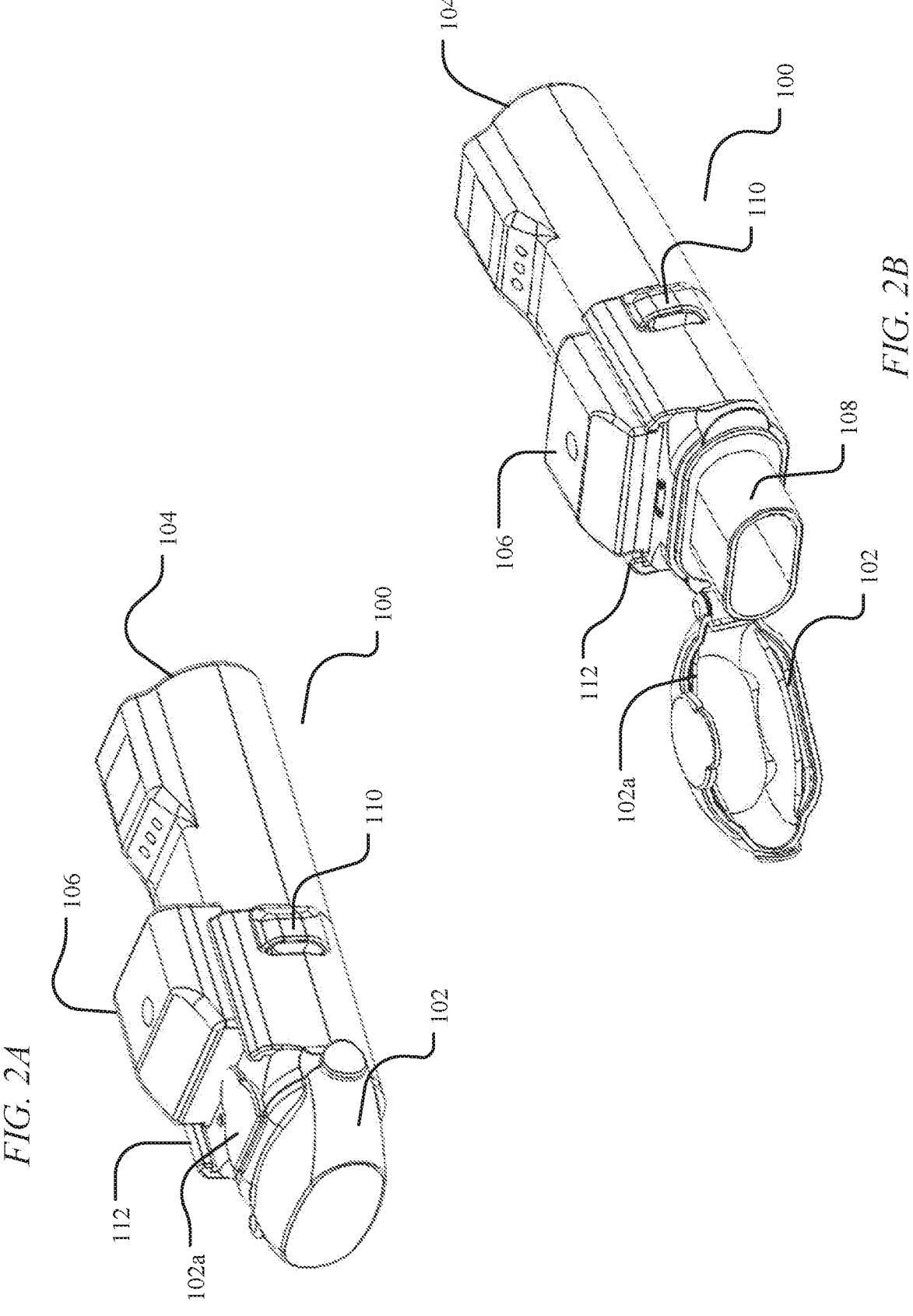
FIGS. 2A-2B illustrate perspective views of an exemplary droplet delivery device, in accordance with embodiments of the disclosure.

FIGS. 2A and 2B illustrate an exemplary droplet delivery device of the disclosure, with FIG. 2A showing the droplet delivery device 100 having a mouthpiece cover 102 in the closed position, and FIG. 2B having a mouthpiece cover 102 in the open position. As shown, the droplet delivery device is configured in an in-line orientation in that the housing, its internal components, and various device components (e.g., the mouthpiece, air inlet flow element, etc.) are orientated in a substantially in-line or parallel configuration e.g., along the airflow path) so as to form a small, hand-held device.

In the embodiment shown in FIGS. 2A and 2B, the droplet delivery device 100 includes a base unit 104 and a fluid reservoir/ejector mechanism module 106. As illustrated in this embodiment, and discussed in further detail herein, the fluid reservoir 106 slides into the front of the base unit 104 via slides 112. In certain embodiments, mouthpiece cover 102 may include a push element 102a that facilitates insertion of fluid reservoir 106. Also illustrated are one or more airflow entrances or openings 110. By way of example, there may be airflow entrances on the opposite side of the device, multiple airflow entrances on the same side of the device, or a combination thereof (not shown). The droplet delivery device 100 also includes mouthpiece 108 at the airflow exit side of the device.

Figure 3:
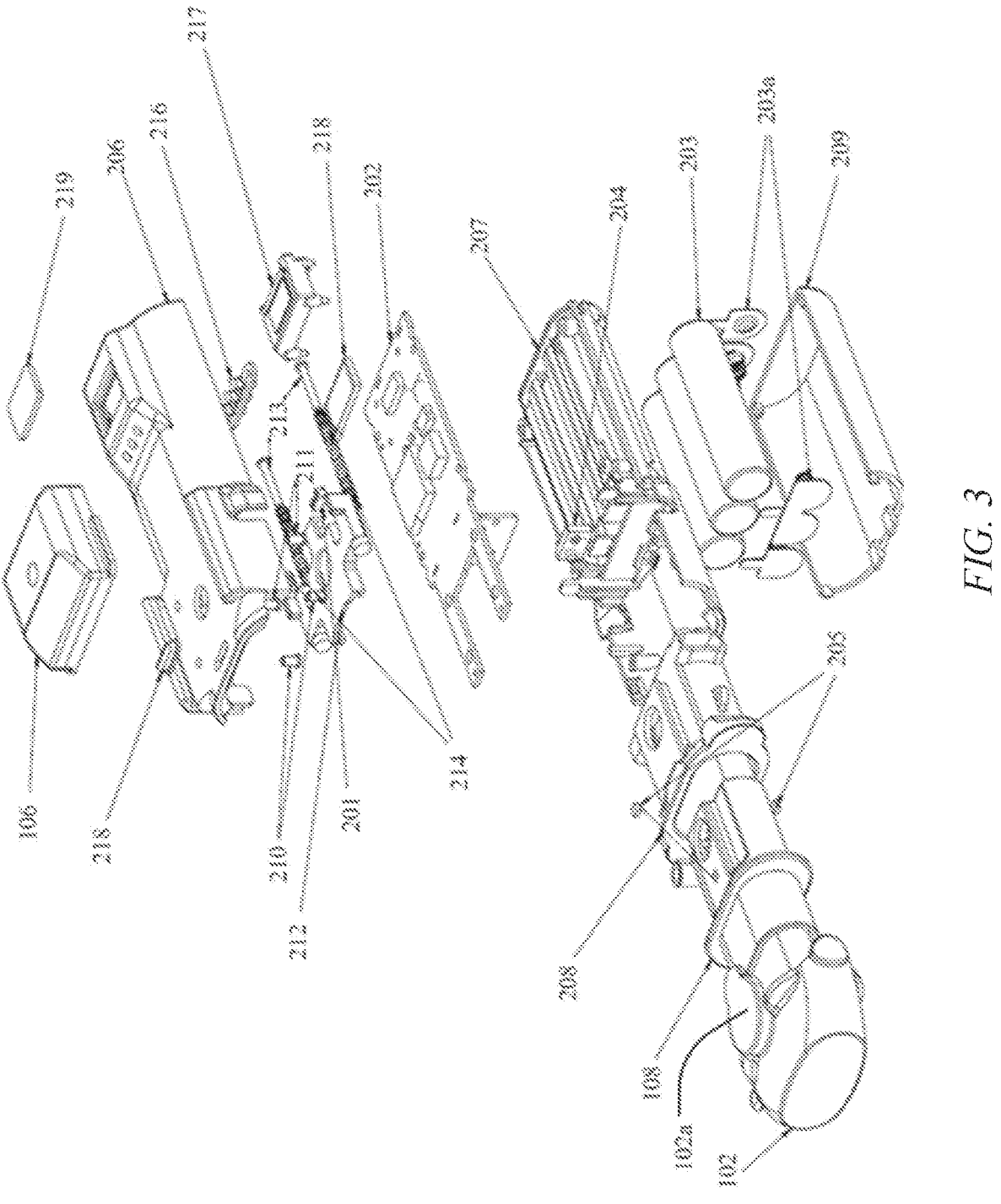
FIG. 3 is an exploded view of droplet delivery device of FIG. 2A-2B, in accordance with embodiments of the disclosure.
Figures 4A, 4B:
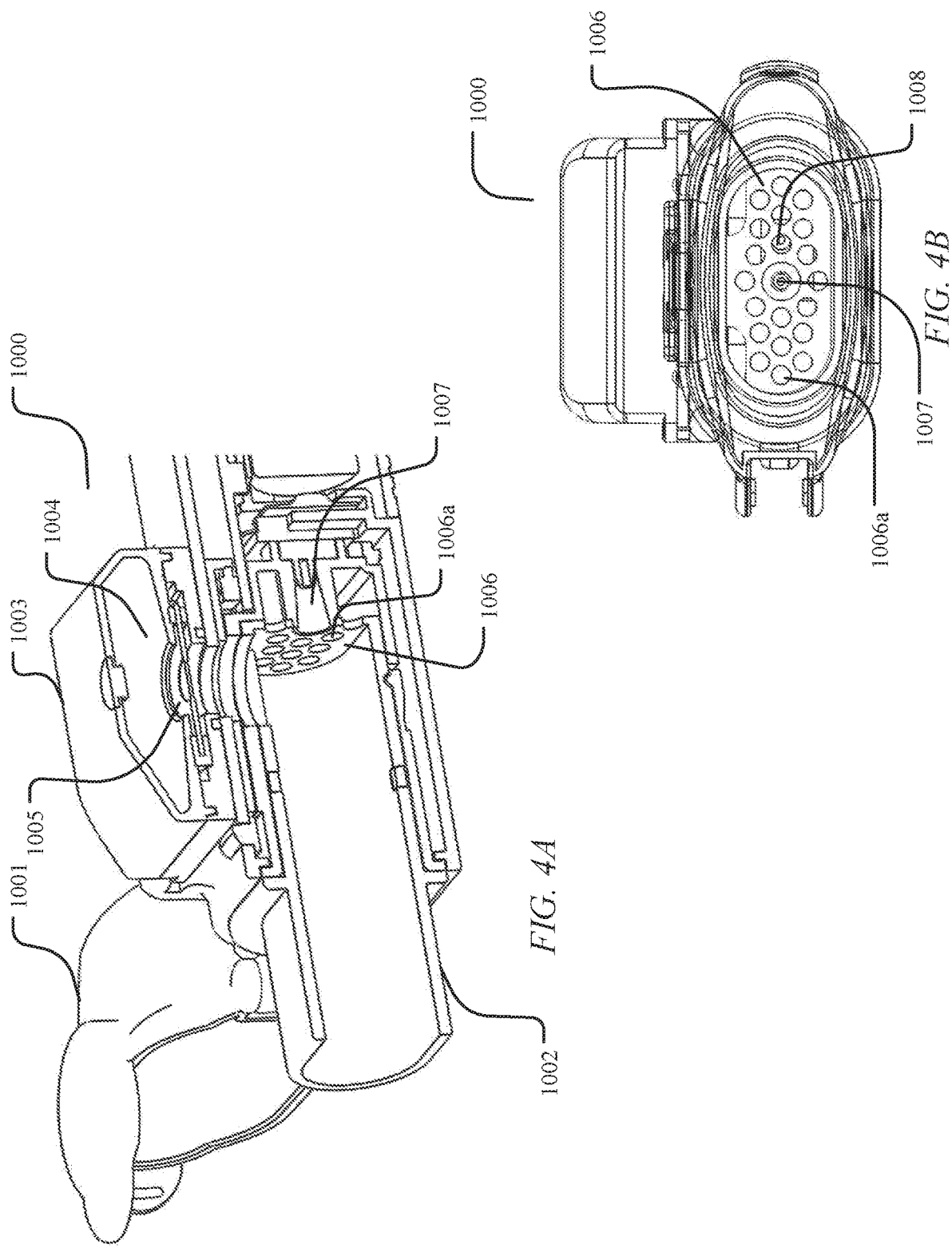
FIG. 4A is a partial cross section perspective view of an in-line droplet delivery device of FIG. 2A-2B comprising a drug delivery ampoule, mouthpiece including an air inlet flow element, and mouthpiece cover, in accordance with an embodiment of the disclosure.
FIG. 4B is a front view of an in-line droplet delivery device of FIG. 2A-2B comprising a drug delivery ampoule and mouthpiece including an air inlet flow element, in accordance with an embodiment of the disclosure.
Figure 4C:
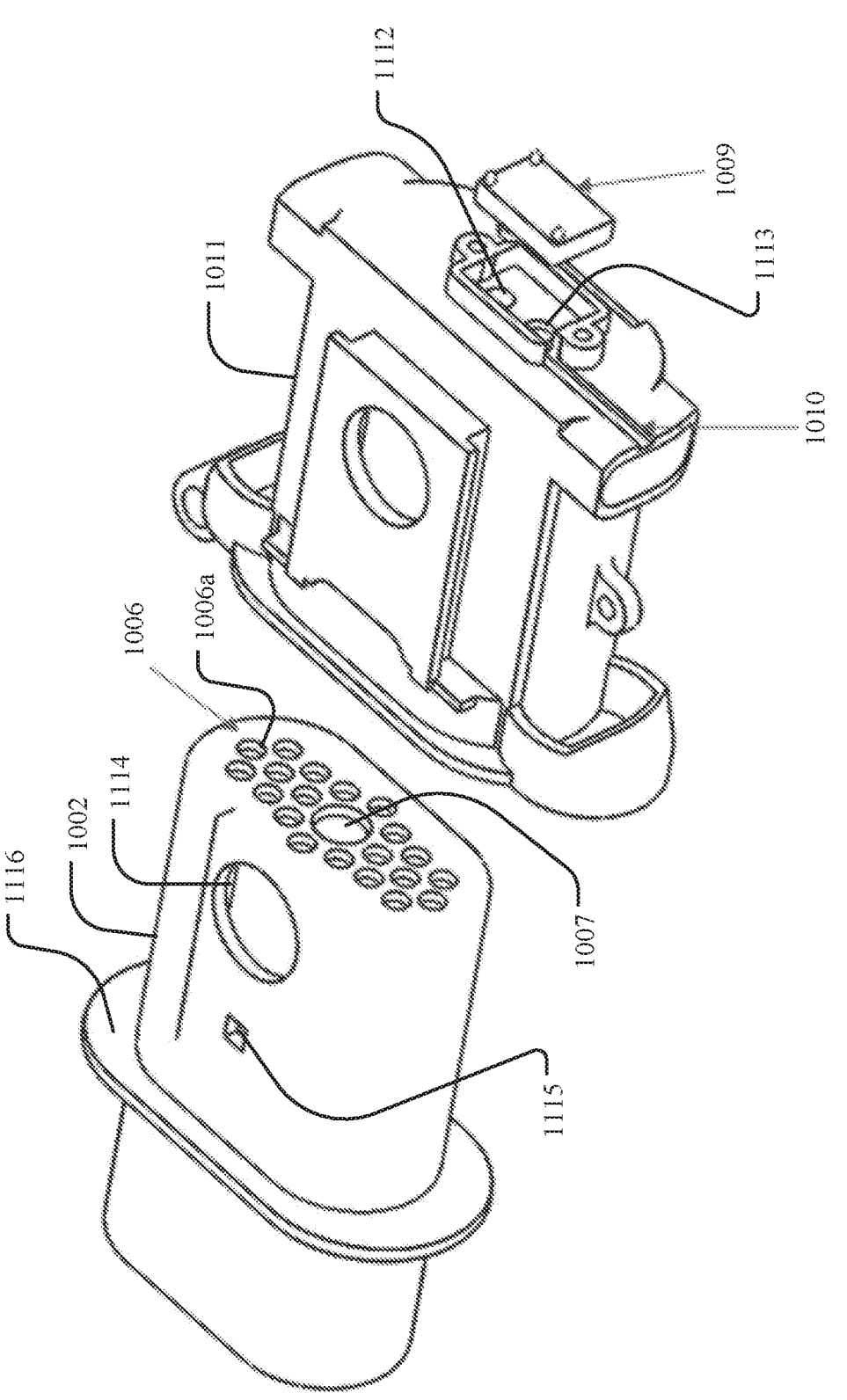
FIG. 4C is a exploded view of components of an in-line droplet delivery device of FIG. 1A-1B including a mouthpiece and internal housing, in accordance with an embodiment of the disclosure.
Figures 5A, 5B:
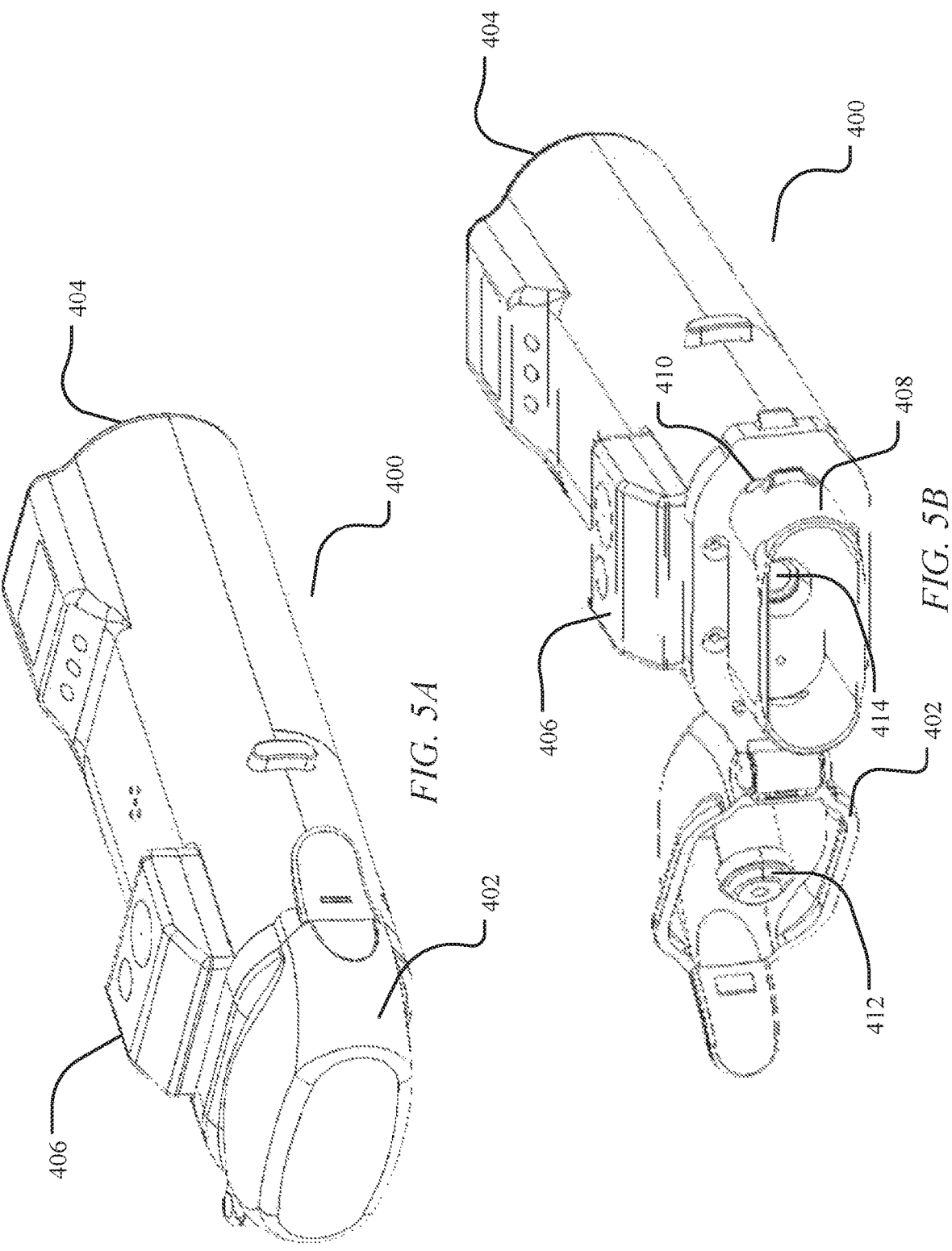
FIGS. 5A-5B illustrate perspective views of another exemplary droplet delivery device, in accordance with embodiments of the disclosure.
Figure 6:
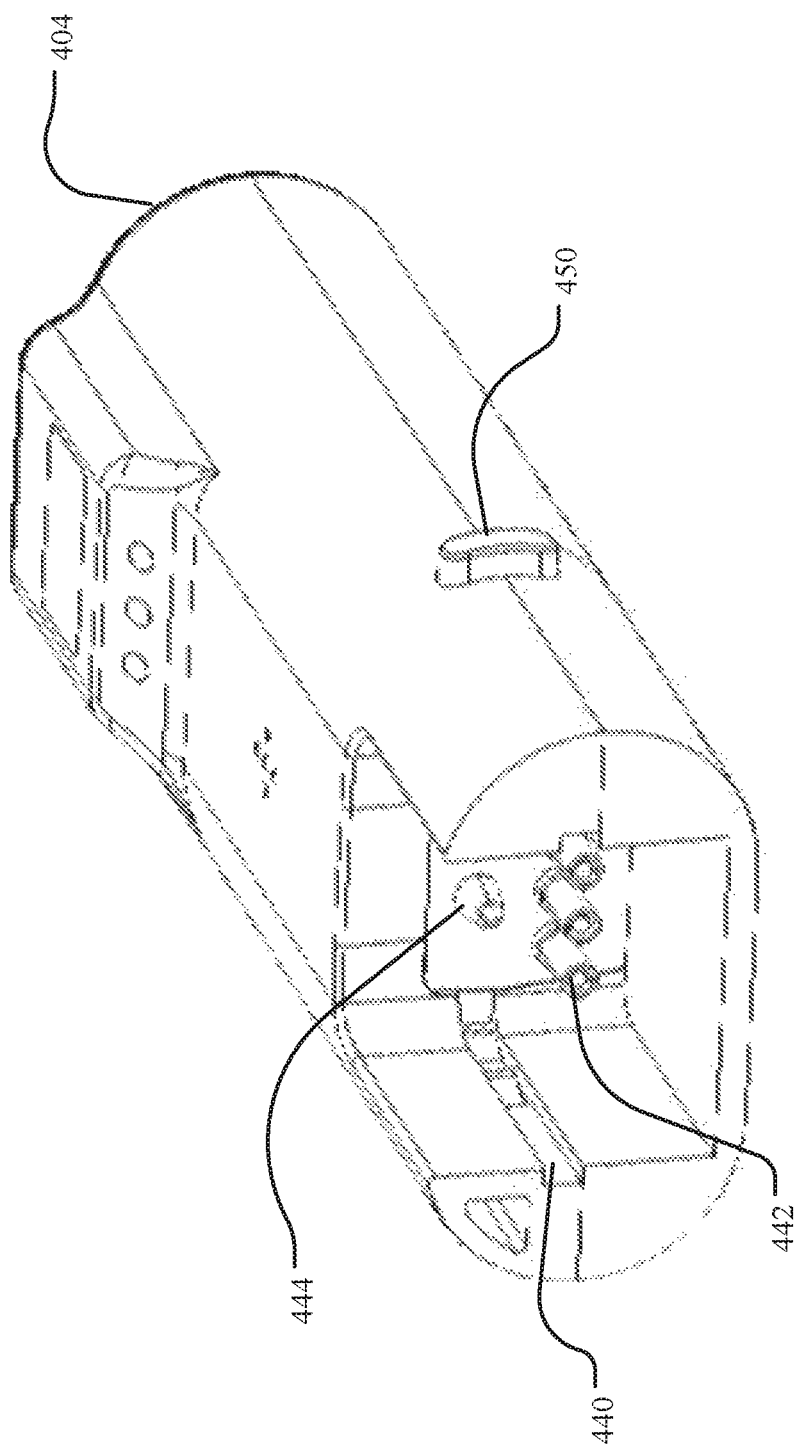
FIG. 6 is a perspective view of a droplet delivery device of FIG. 5A-5B without the fluid reservoir/ejector mechanism module inserted, in accordance with embodiments of the disclosure.
Figures 7A, 7B:
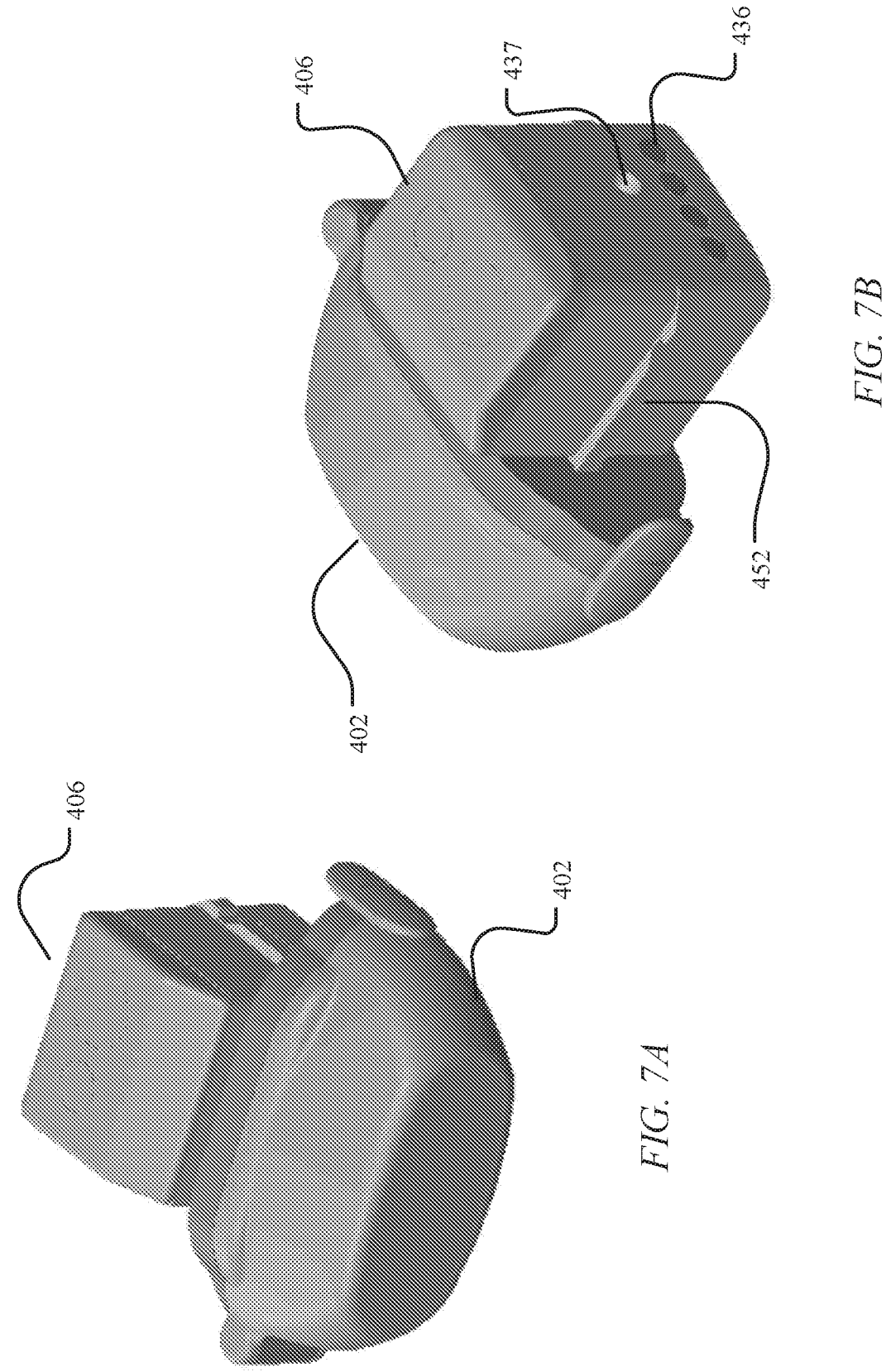
FIGS. 7A-7B are perspective views of a fluid reservoir/ejector mechanism module and mouthpiece cover, showing a front view (FIG. 7A) and back view (FIG. 7B), in accordance with embodiments of the disclosure.

With reference to FIG. 3, an exploded view of the exemplary droplet delivery device of FIGS. 2A and 2B is shown, including internal components of the housing including a power/activation button 201; an electronics circuit board 202; a fluid reservoir/ejector mechanism module 106 that comprises an ejector mechanism (not shown) and reservoir; and a power source 203 (e.g., three AAA batteries, which may optionally be rechargeable) along with associated contacts 203a. In certain embodiments, the reservoir may be single-unit dose or multi-unit dose that may be replaceable, disposable or reusable. Also shown, one or more pressure sensors 204 and optional spray sensors 205. In certain embodiments, the device may also include various electrical contacts 210 and 211 to facilitate activation of the device upon insertion of drug delivery ampoule 106 into the base unit. Likewise, in certain embodiments, the device may include slides 212, posts 213, springs 214, and ampoule lock 215 to facilitate insertion of drug delivery ampoule 106 into the base unit.

The components may be packaged in a housing, and generally oriented in an in-line configuration. The housing may be disposable or reusable, single-dose or multi-dose. Although various configurations to form the housing are within the scope of the disclosure, as illustrated in FIG. 2, the housing may comprise a top cover 206, a bottom cover 207, and an inner housing 208. The housing may also include a power source housing or cover 209.

In certain embodiments, the device may include audio and/or visual indications, e.g., to provide instructions and communications to a user. In such embodiments, the device may include a speaker or audio chip (not shown), one or more LED lights 216, and LCD display 217 (interfaced with an LCD control board 218 and lens cover 219). The housing may be handheld and may be adapted for communication with other devices via a Bluetooth communication module or similar wireless communication module, e.g., for communication with a subject's smart phone, tablet or smart device (not shown).

In certain embodiments, an air inlet flow element (not shown) may be positioned in the airflow at the airflow entrance of the housing and configured to facilitate non-turbulent (i.e., laminar and/or transitional) airflow across the exit side of aperture plate and to provide sufficient airflow to ensure that the ejected stream of droplets flows through the droplet delivery device during use. The air inlet flow element may comprise one or more openings formed there through and may be configured to increase or decrease internal pressure resistance within the droplet delivery device during use. In come embodiments, the air inlet flow element may comprises an array of one or more openings. In other embodiments, the air inlet flow element may comprise one or more baffles. In certain aspects, the one or more baffles may comprise one or more airflow openings.

In some embodiments, the air inlet flow element may be positioned within the mouthpiece. In other embodiments, the air inlet flow element may be positioned behind the exit side of the aperture plate along the direction of airflow. In yet other embodiments, the air inlet flow element is positioned in-line or in front of the exit side of the aperture plate along the direction of airflow.

Aspects of the present embodiment further allows customizing the internal pressure resistance of the particle delivery device by allowing the placement of laminar flow elements having openings of different sizes and varying configurations to selectively increase or decrease internal pressure resistance, as will be explained in further detail herein.

FIGS. 4A-4C illustrate certain exemplary air inlet flow elements of the disclosure. FIGS. 4A-4C also illustrate the position of pressure sensors, the mouthpiece, and air channels for reference pressure sensing. However, the disclosure is not so limited, and other configurations including those described herein are contemplated as within the scope of the disclosure. While not being so limited, the air inlet flow elements of FIGS. 4A-4C are particularly suitable for use with the droplet delivery devices of FIGS. 2A-2B.

More particularly, FIG. 4A illustrates a cross-section of a partial in-line droplet delivery device 1000 of the disclosure including a mouthpiece cover 1001, a mouthpiece 1002, a drug delivery ampoule 1003 comprising a drug reservoir 1004 and an ejector mechanism 1005. As illustrated, the droplet delivery device includes an air inlet flow element 1006 having an array of holes 1006*a* at the air entrance of the mouthpiece 1002. Also shown is a pressure sensor port 1007, which may be used to sense a change in pressure within the mouthpiece. With reference to FIG. 4B, a front view of the device 1000 is illustrated, wherein a second pressure sensor port 1008 is shown to provide for sensing of a reference or ambient pressure.

FIG. 4C illustrates a partial exploded view including mouthpiece 1002 and inner housing 1011. As shown, mouthpiece 1002 includes air intake flow element 1006 with an array of holes 1006*a*, and pressure sensor port 1007. Further, mouthpiece 1002 may include an ejection port 1114 positioned, e.g., on the top surface of the mouthpiece so as to align with the ejector mechanism to allow for ejection of the stream of droplets into the airflow of the device during use. Other sensor ports 1115 may be positioned as desired along the mouthpiece to allow for desired sensor function, e.g., spray detection. The mouthpiece may also include positioning baffle 1116 that interfaces with the base unit upon insertion. Inner housing 1011 includes pressure sensor board 1009 and outside channel 1010 for facilitating sensing of reference or ambient pressure. The inner housing further includes a first pressure sensing port 1112 to facilitate sensing of pressure changes within the device (e.g., within the mouthpiece or housing), and a second pressure sensing port 1113 to facilitate sensing of reference or ambient pressure.

In another embodiment, FIGS. 5A and 5B illustrate an alternative droplet delivery device of the disclosure wherein the fluid reservoir/ejector mechanism module is inserted into the front of the base unit. With reference to FIG. 5A showing the droplet delivery device 400 with a base unit 404 having a mouthpiece cover 402 in the closed position, and FIG. 5B with a base unit 404 having a mouthpiece cover 402 in the open position. As shown, the droplet delivery device is configured in an in-line orientation in that the housing, its internal components, and various device components (e.g., the mouthpiece, air inlet flow element, etc.) are orientated in a substantially in-line or parallel configuration (e.g., along the airflow path) so as to form a small, hand-held device.

In the embodiment shown in FIGS. 5A and 5B, the droplet delivery device 400 includes a base unit 404 and a fluid reservoir 406. As illustrated in this embodiment, and discussed in further detail herein, the fluid reservoir 406 slides into the front of the base unit 404. In certain embodiments, mouthpiece cover 402 may include aperture plate plug 412 which may cover aperture plate 414 when cover 402 is in a closed position. Also illustrated are one or more airflow entrances or openings 410 in mouthpiece 408. By way of example, there may be airflow entrances on the opposite side of the device, multiple airflow entrances on the same side of the device, or a combination thereof (not shown). The droplet delivery device 400 also includes mouthpiece 408 at the airflow exit side of the device.

FIG. 6 illustrates the base unit 404 of the embodiment of FIGS. 5A and 5B without the fluid reservoir/ejector mechanism module inserted. Without the fluid reservoir/ejector mechanism module inserted, tracks 440 for directing the module into place, electrical contacts 442, and sensor port 444 are shown. Also shown is release button 450.

FIGS. 7A and 7B illustrate a fluid reservoir/ejector mechanism module 406 with mouthpiece cover 402 attached and in a closed position in front view (FIG. 7A) and back view (FIG. 7B). FIG. 78 illustrates electrical contacts 436 and sensor port 437 of the module, as well as protruding slides 452 to facilitate placement of the module into tracks 440 during insertion. By way of example, when fluid reservoir/ejector mechanism module 406 is inserted into base unit 404, protruding slides 452 mate with tracks 440, sensor port 437 mates with sensor port 444, and electrical contacts 436 mates with electrical contacts 442. The fluid reservoir/ejector mechanism module is pushed into the base unit and locked into place with the protruding slides and tracks engaging one another. During use, a pressure sensor located on the control board senses pressure changes within the device via the pressure sensing ports (e.g., within the mouthpiece). To facilitate detection of pressure changes, the base unit includes a second pressure sensing port and outside channel (not shown) to facilitate sensing of reference or ambient pressure.

Again, in certain embodiments, an air inlet flow element (not shown) may be positioned in the airflow at the airflow entrance of the housing and configured to facilitate non-turbulent (i.e., laminar and/or transitional) airflow across the exit side of aperture plate and to provide sufficient airflow to ensure that the ejected stream of droplets flows through the droplet delivery device during use. The air inlet flow element may comprise one or more openings formed there through and may be configured to increase or decrease internal pressure resistance within the droplet delivery device during use. In come embodiments, the air inlet flow element may comprises an array of one or more openings. In other embodiments, the air inlet flow element may comprise one or more baffles. In certain aspects, the one or more baffles may comprise one or more airflow openings.

In some embodiments, the air inlet flow element may be positioned within the mouthpiece. In other embodiments, the air inlet flow element may be positioned behind the exit side of the aperture plate along the direction of airflow. In yet other embodiments, the air inlet flow element is positioned in-line or in front of the exit side of the aperture plate along the direction of airflow.

Aspects of the present embodiment further allows customizing the internal pressure resistance of the particle delivery device by allowing the placement of laminar flow elements having openings of different sizes and varying configurations to selectively increase or decrease internal pressure resistance.

As illustrated in the various embodiments of the figures, in certain embodiments of the droplet device, the housing and ejector mechanism are oriented such that the exit side of the aperture plate is perpendicular to the direction of airflow and the stream of droplets is ejected in parallel to the direction of airflow. In other embodiments, the housing and ejector mechanism are oriented such that the exit side of the aperture plate is parallel to the direction of airflow and the stream of droplets is ejected substantially perpendicularly to the direction of airflow such that the ejected stream of droplets is directed through the housing at an approximate 90 degree change of trajectory prior to expulsion from the housing.

In other embodiments, the droplet delivery device may comprise a body housing, a mouthpiece having an ejector mechanism, and a fluid cartridge having at least one fluid reservoir. In certain embodiments, the ejector mechanism may comprise at least one ultrasonic actuator and at least one aperture plate of the disclosure (i.e., having the desired surface contact angle(s) at one or more surfaces). The device may further comprise at least one differential pressure sensor configured to activate the ejector mechanism upon sensing a pre-determined pressure change within the device to thereby generate the ejected stream of droplets.

More specifically, in certain embodiments, an exemplary droplet delivery device may generally comprise a mouthpiece, a fluid cartridge, a body housing, and at least one differential pressure sensor. In certain embodiments, the mouthpiece is positioned at an airflow exit of the device, the mouthpiece comprising one or more air flow entrance ports, an airflow exit opening, an electronically actuated ejector mechanism of the disclosure, an ejection chamber, and a fluid transport mating extension. The fluid cartridge generally comprises at least one reservoir for receiving a volume of fluid, and at least one sealing mechanism, the fluid cartridge disposed within or in fluid communication with the mouthpiece. The body housing comprises a power source and control board. The at least one differential pressure sensor is positioned within the mouthpiece or positioned within the body housing and in fluid communication with the mouthpiece, the at least one differential pressure sensor configured to activate the ejector mechanism upon sensing a pre-determined pressure change within the mouthpiece to thereby generate the ejected stream of droplets.

In certain embodiments, the electronically actuated ejector mechanism is in fluid communication with the reservoir at a fluid cartridge side of the ejector mechanism, and configured to generate the ejected stream of droplets, the ejector mechanism comprising a piezoelectric actuator and an aperture plate of the disclosure, the piezoelectric actuator operable to oscillate the aperture plate at a frequency to thereby generate the ejected stream of droplets; and the ejection chamber is located adjacent the ejector mechanism on the fluid cartridge side of the ejector mechanism.

In certain embodiments, the fluid transport mating extension is positioned within the mouthpiece at a fluid cartridge side of the mouthpiece. The fluid transport mating extension is configured to provide for a fluid path between the fluid cartridge and the ejector mechanism. The fluid transport mating extension may interface with or extend through the sealing mechanism of the fluid cartridge to create fluid communication between the fluid cartridge and the ejector mechanism.

In certain embodiments, the one or more air flow entrance ports of the mouthpiece are configured as an air inlet flow element, wherein the air inlet flow element and mouthpiece are configured to facilitate non-turbulent airflow across an exit side of the aperture plate and to provide sufficient airflow through the mouthpiece during use.

In specific embodiments, the ejector mechanism is electronically breath activated by at least one differential pressure sensor located within the ultrasonic droplet delivery device upon sensing a pre-determined pressure change within the mouthpiece. In certain embodiments, such a pre-determined pressure change may be sensed during an inspiration cycle by a user of the device. In certain embodiments, the pressure sensor may be located in the mouthpiece, on the airflow exit side of the ejector mechanism. In other embodiments, the pressure sensor may be located in the body housing, and may be in fluid communication with the airflow exit side of the ejector mechanism.

In some aspects, the droplet delivery device further includes one or more air inlet flow elements positioned in the airflow at the airflow entrance of the device and configured to facilitate non-turbulent (i.e., laminar and/or transitional) airflow across the exit side of at least one aperture plate and to provide sufficient airflow to ensure that the ejected stream of droplets flows through the droplet delivery device during use. In some embodiments, the air inlet flow element may be positioned within the mouthpiece. In certain embodiments, the air inlet flow element(s) may be positioned behind the exit side of the aperture plate along the direction of airflow, or in-line or in front of the exit side of the aperture plate along the direction of airflow. In certain embodiments, the air inlet flow element(s) comprises one or more openings configured to increase or decrease internal pressure resistance within the droplet delivery device during use. For instance, in certain embodiments, the air inlet flow element(s) comprise an array of one or openings. In other embodiments, the air inlet flow element(s) comprise one or more baffles, e.g., wherein the one or more baffles comprise one or more airflow openings.

The airflow exit of the mouthpiece of the droplet delivery device through which the ejected aerosol of droplets exit as they are inhaled into a subject's airways, may be configured and have, without limitation, a cross sectional shape of a circle, oval, rectangular, hexagonal or other shape, while the shape of the length of the tube, again without limitation, may be straight, curved or have a Venturi-type shape.

In accordance with certain aspects of the disclosure, droplet delivery devices are disclosed which include at least one ultrasonic ejector mechanism in fluid communication with at least one aperture plate of the disclosure. In certain embodiments, the ultrasonic ejector mechanism may comprise a piezoelectric actuator, optionally amplified by an elongated ultrasonic "horn". Such ultrasonic "horn" actuators are an impedance matching device that are wide at a vibration generating, piezoelectric end and thin at a fluid contact, horn end.

In certain embodiments, exemplary ultrasonic horn actuators may be about half a wavelength long, and are typically made of metal, e.g., titanium, stainless steel or aluminum. The horn may be specially tapered, fluted, or a stepped rod, and produces displacements large enough to create a stream of droplets or aerosol. The horn is designed to allow for efficient coupling of piezo energy into fluid (i.e., small, high-stiffness motion to large, less-still motion). By way of non-limiting example, if the piezo's 1% strain creates a 1% strain in the horn, the horn being ten times longer potentially has ten times the displacement.

In certain embodiments, if configured to include an ultrasonic horn, the aperture plate may be positioned close to the fluid end of the horn, but not specifically touching the horn, as will be described in further detail herein. The horn may generally be long enough that it and the piezo element form a half wavelength structure with a nodal point having a point of high stress and minimal motion between the midpoint of the body of the horn and the step in the horn. Horn lengths may be optimized during design, with parameters set due based on their multiple masses. By way of non-limiting example, titanium horns may be used in high temperature, high abrasion settings to address high nodal stress.

Without intending to be limited by theory, a horn extracts energy from a vibrating piezo element, and transmits it into fluid to be ejected through the aperture plate. In practice, the horn may be stretch in resonance to magnify the amplitude of the piezo element vibration. Accordingly, the horn material should preferably stretch with low loss and sufficient strength at the nodal point to support the stress associated with the stretch (strain). In certain aspects, horn length is minimally half a wavelength, e.g., at 100 kHz. By way of example, polymer horns would generally need to be twice as long because the speed of sound is about half for polymers as compared to metals.

Figures 8A, 8B, 8C:
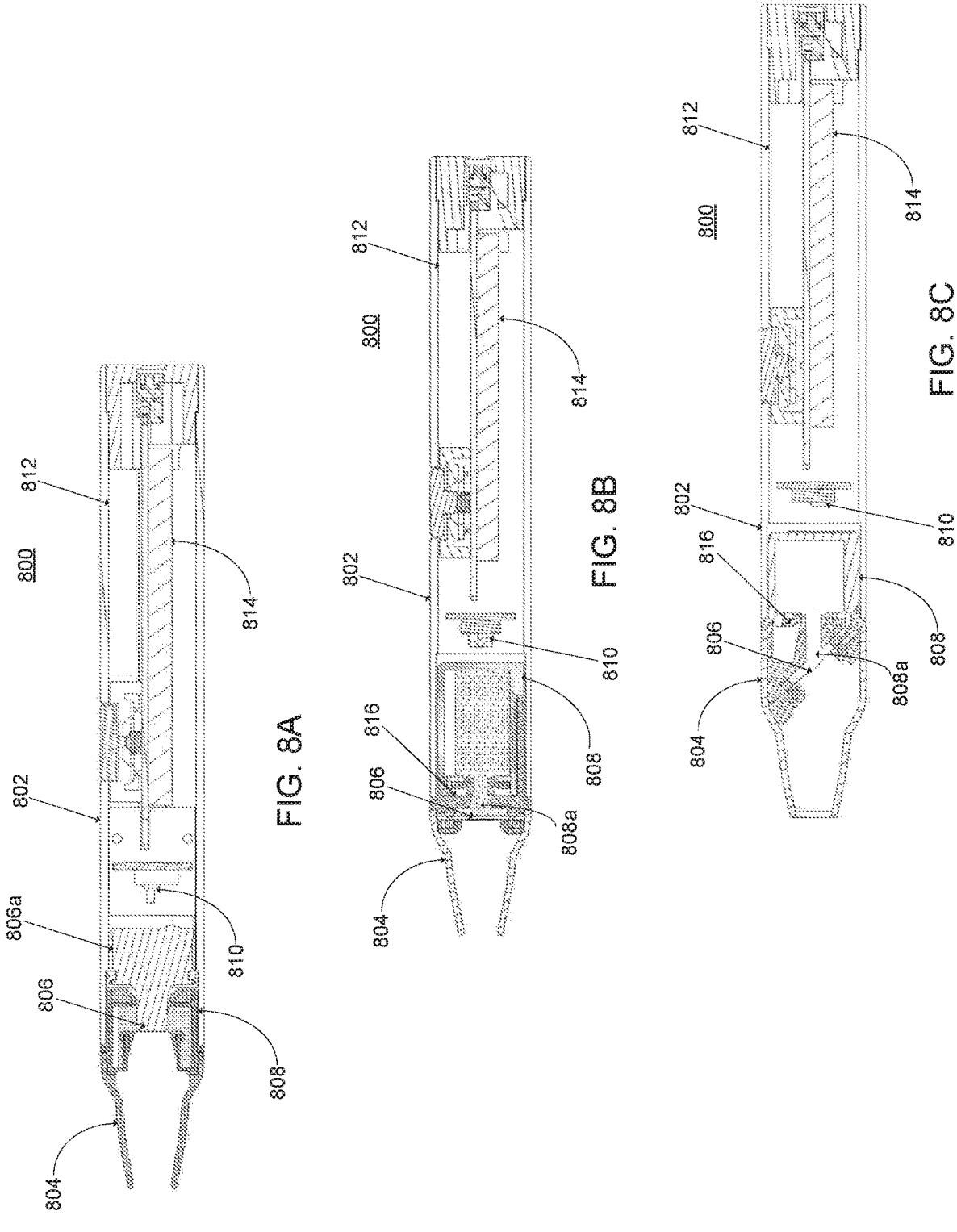
FIGS. 8A-8C illustrate cross-sections of various droplet delivery devices, according to certain embodiments of the disclosure.

Exemplary droplet delivery devices 800 of the disclosure are illustrated in FIGS. 8A-8C, with a mouthpiece 804, ejector mechanism 806, fluid cartridge 808, pressure/flow sensor 810, control board 812, power source/battery 814, and a body housing 802. The ejector mechanism 806 may be interfaced with or located within the mouthpiece 804 or the fluid cartridge 808.

As explained in further detail herein, the ejector mechanism may be orientated at various angles within the device, with respect to the direction of droplet generation, airflow through the device, and internal surfaces within the device. Without intending to be limited by theory, it is believed that orientation of the ejector mechanism with respect to the direction of droplet generation, airflow through the device, and internal surface within the device serves to optimize droplet size distribution via inertial filtering, which filters and excludes larger droplets from the droplet plume.

In some embodiments, the ejector mechanism may be oriented perpendicularly (e.g., vertical) to the direction of airflow through the device, such that droplets are initially ejected into the direction of airflow. Such a configuration minimizes inertial filtering of generated droplets, allowing most droplets to flow in the entrained airflow within the mouthpiece (other than impacts of droplets at the sidewalls of the mouthpiece and inertial settling along the air flow path). In other embodiments, the ejector mechanism may be orientated at an angle with respect to the direction of airflow through the device. By way of example, the ejector mechanism may be oriented at about 5° from perpendicular, about 10° from perpendicular, about 15° from perpendicular, about 20° from perpendicular, about 25° from perpendicular, about 30° from perpendicular, about 35° from perpendicular, about 40° from perpendicular, about 45° from perpendicular, etc. In such embodiments, the droplets may be ejected into the airflow at an angle, such that smaller droplets are able to flow in the entrained airflow within the mouthpiece, and larger droplets are more likely to impact the sidewalls of the mouthpiece along the air flow path (or settle out along the air flow path).

FIG. 8A illustrates an embodiment wherein the ejector mechanism 806 includes an acoustic horn 806a. During use, droplets are ejected from the fluid reservoir through the openings in the aperture plate of the ejector mechanism when the ultrasonic actuator vibrates. The ultrasonic actuator vibrates when a piezoelectric actuator affixed to or interfaced with an ultrasonic horn and operable to oscillate the horn is activated by a control circuit located on the electronics board. The horn amplifies the amplitude of the piezo vibration into the fluid within the fluid reservoir. In other embodiments (not shown), the fluid cartridge may interface with an aperture plate on one side and a thin ultrasonic port on the opposite side. The ultrasonic port may be any material suitable to conduct the vibrational energy, e.g., a thin or elastic film. The ultrasonic horn/piezo actuator may then transmit vibrational energy to the fluid cartridge through the ultrasonic port.

In certain embodiments, for effective coupling of ultrasonic vibration (energy transfer) between the end of the horn and the fluid, the end of the horn must transmit both compression and tension phases of each cycle of ultrasonic vibration into the fluid. As described herein, the horn does not need to physically couple to or touch the aperture plate to achieve ejection of droplets. Rather, the horn needs to be in vibrational communication with the aperture plate so as to allow energy transfer between the horn and the aperture plate, e.g., within about 0.1 to 2 mm from the aperture plate. In certain embodiments, this may be accomplished by both the aperture plate and horn being supported on structures which attach to the outer shell of the body of the device. However, the present disclosure contemplates further configurations for achieving effective and efficient coupling.

In accordance with certain aspects, the devices of the disclosure address challenges of fluid leakage or evaporation at the interface between the fluid cartridge and the ultrasonic horn. For example, fluid within the fluid reservoir may be inhibited from leaking by an O-ring seal between the horn and the reservoir. In an alternative embodiment for inhibiting fluid leakage at the horn connection, the horn may be connected to a floating "wall" or ultrasonic port of the cartridge that communicates the vibration to the aperture plate by an internal element. This wall or port can be a compliant material such as an elastic rubber or a plastic sheet that flexes. In certain embodiments, the total area of the wall that moves may be minimized to avoid ultrasonic energy loss. The spacing between the wall and the aperture plate also may also be minimized (millimeter or fraction of a millimeter) to accommodate desired fluid reservoir sizing. The connection between the horn and wall may be configured to transmit both compressive and tensile forces of the ultrasonic vibration. In certain embodiment, the connection may be accomplished by suitable mechanical connection, such as a set screw or "bayonet" connection where the horn has tangs which insert into groves in a transfer element that is part of the cartridge and a twist allows the tangs to be held rigidly for axial motion. The internal element that transmits the vibration is part of the attachment membrane and is short to have minimal effect on the vibration characteristics of the horn. In yet an additional embodiment for inhibiting fluid leakage at the horn connection, the ultrasonic horn may be connected to the fluid reservoir via a rigid connection block to transmit both the tensile and compressive aspects of the ultrasonic vibration. This embodiment is particularly suitable for configuration where the fluid volume is small (typically, example a single dose cartridge). Again a set screw or bayonet type of connection may be used to connect the horn to the rigid connection block.

FIG. 8B illustrates an embodiment wherein the ejector mechanism is aligned in an orientation generally perpendicular (e.g., vertical) to the direct of air flow through the device. As illustrated in the embodiment of FIG. 8B, a fluid ejection chamber 808a is located behind the ejector mechanism 806, and a sealing mechanism 816 is located between the ejector mechanism 806 and the fluid cartridge 808. A configuration wherein the ejector mechanism is oriented vertically can allow the stream of ejected droplets to flow in the air flow through the device in a generally unimpeded manner, i.e., there is minimal inertial filtering of droplets due to impact along the sides of mouthpiece.

FIG. 8C illustrates an embodiment wherein the ejector mechanism is aligned in an orientation that is angled to the direction of air flow through the device. Again, in this embodiment, a fluid ejection chamber 808a is located behind the ejector mechanism, and a sealing mechanism 816 is located between the ejector mechanism 806 and the fluid cartridge 808. A configuration wherein the ejector mechanism is oriented at an angle can allow the stream of ejected droplets to flow in the air flow through the device in a manner so as to be subject to inertial filtering due to impact along the sides of the mouthpiece. This inertial filtering can serve to capture and remove larger droplets from the air flow stream to the extent desired.

In certain embodiments, the mouthpiece may be interfaced with (and optionally removable and/or replaceable), integrated into, or part of the body housing. In other embodiments, the mouthpiece may be interfaced with (and optionally removable and/or replaceable), integrated into, or part of the fluid cartridge.

Figures 9A, 9B, 9C:
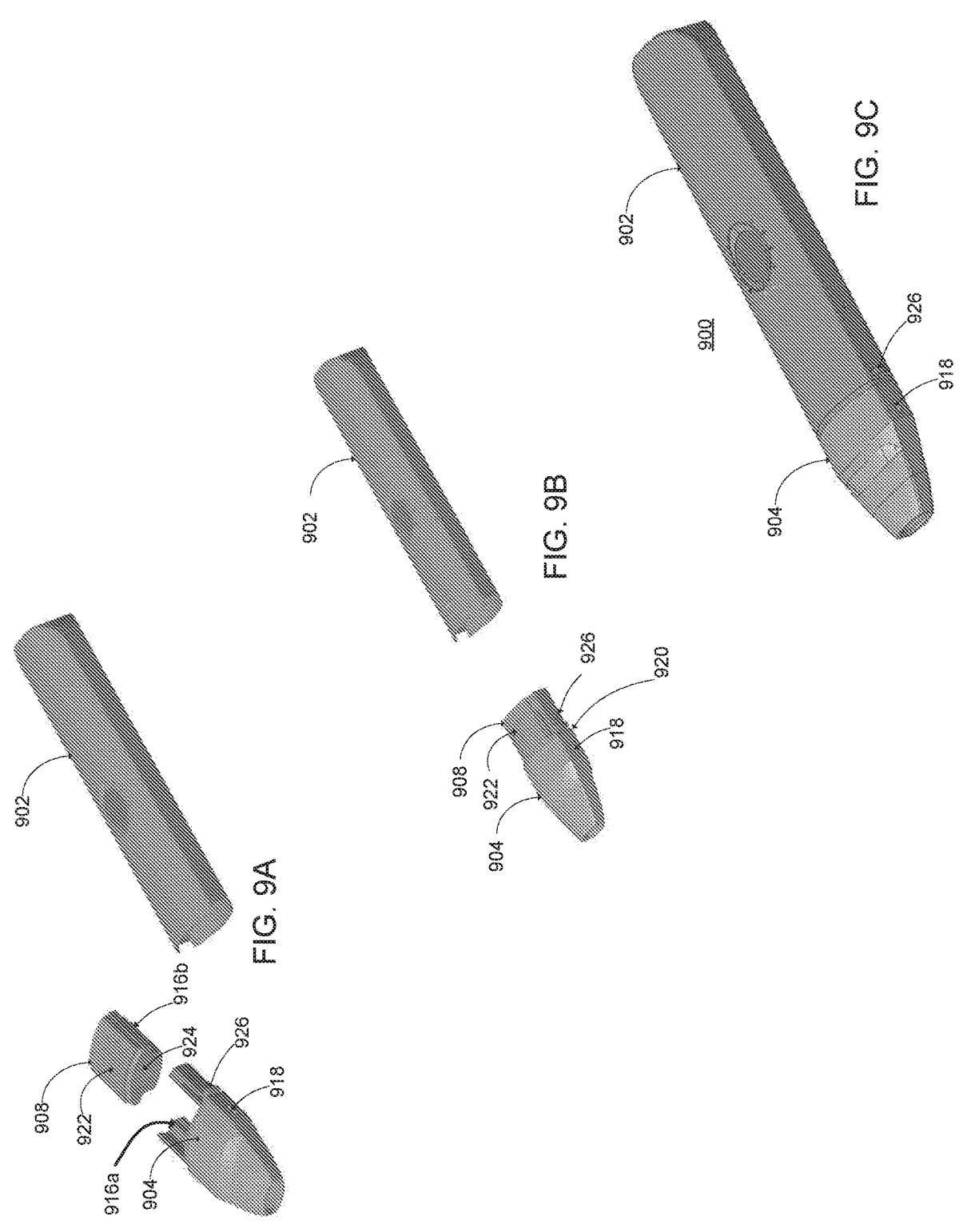
FIGS. 9A-9C illustrate perspective views of a droplet delivery device in accordance with embodiments of the disclosure.

With reference to FIGS. 9A-9C, in certain aspects, the body housing 902 and mouthpiece 904 may fit together to enclose the fluid cartridge 908 and the ejector mechanism (not shown) within an enclosed device 900. As illustrated in FIG. 9A, in certain embodiments, the mouthpiece 904, fluid cartridge 908, and body housing 902 may each be configured as separate elements. With reference to FIG. 9B, the mouthpiece 904 may house the ejector mechanism (not shown), and the fluid cartridge 208 may first be connected to the mouthpiece 904 to place the fluid cartridge 908 in fluid communication with the ejector mechanism (not shown) within the mouthpiece 904. As shown in FIG. 9C, once the fluid cartridge 908 is connected to the mouthpiece 904, the combined mouthpiece/fluid cartridge 920 may be inserted into the body housing 902 to enclose the fluid cartridge 908 within the device 900.

In certain embodiments, body housing 902 may comprise a power source (e.g., batteries) and electronics (e.g., a control board) for controlling operation and actuation of the ejector mechanism, flow/pressure sensors, etc. The mouthpiece 904 may include cartridge slides 916a, and the fluid cartridge 908 may include cartridge rails 916b configured to cooperate with the cartridge slides 916a to thereby secure the fluid cartridge 908 to the mouthpiece 904. The fluid cartridge 908 may include one or more housing locks 926 configured to interface with and lock into the body housing 902. The fluid cartridge 908 may also include one or more vents 922, and may include an access port 924 that may be configured so as to be self-sealing.

The mouthpiece 904 is generally located at an airflow exit of the device 900, and one or more airflow entrance ports 918 are generally located on airflow entrances of the mouthpiece 904 or body housing 902 (not shown). The ejector mechanism may be located within the device 900, e.g., within the mouthpiece 904 or fluid cartridge 908, so as to be in fluid communication with the fluid cartridge such that the ejector mechanism can receive fluid from the fluid reservoir during use. In certain embodiments, the ultrasonic (e.g., piezoelectric) actuator is interfaced with the aperture plate and operable to oscillate the aperture plate at a frequency to thereby generate an ejected stream of droplets. As illustrated, the fluid cartridge 908 may be removable from the device 900 and replaceable. The fluid cartridge may include one or more fluid reservoir(s) that enclose a single or multiple administrations of a composition to be delivered to a user.

The droplet delivery devices of the disclosure may include one or more sealing mechanisms. In certain embodiments, devices of the disclosure are configured to minimize evaporation from multi-use cartridges or single-use cartridges that are placed in the device after removing sealing tape from the fluid cartridge. By way of example, in one embodiment, the mouthpiece may include one or more sealing mechanisms to cover any fluid exit paths when not in use and/or to cover the aperture plate when not in use. For example, in one embodiment, a face seal may be provided which covers the aperture plate when not in use. Any suitable face seal may be used, for instance, a seal may be part of a mouthpiece cap that is closed by the user after an inhalation. The cap may include a spring loaded face seal that presses against a smooth stainless steel surface within the mouthpiece but outside the aperture plate. In another embodiment, a seal may be provided between the connection of the piezo horn and the fluid cartridge.

In other embodiments, the fluid cartridge and/or mouthpiece may include one or more sealing mechanisms at the interface of the fluid cartridge and the ejector mechanism to minimize evaporation of the fluid within the reservoir. In some embodiments, the fluid cartridge may have a removable sealing tape which prevents evaporation prior to attachment to the body. In other embodiments, the device may include one or more sealing mechanisms to minimize evaporation at the connection point between the fluid cartridge and body.

In certain aspects, the droplet delivery device further includes a surface tension plate between the aperture plate and the reservoir, wherein the surface tension plate is configured to increase contact between the volume of fluid and the aperture plate. In other aspects, the ejector mechanism and the surface tension plate are configured in parallel orientation. In yet other aspects, the surface tension plate is located within 2 mm of the aperture plate so as to create sufficient hydrostatic force to provide capillary flow between the surface tension plate and the aperture plate.

In certain embodiments, the droplet delivery device may include a combination reservoir/ejector mechanism module that may be replaceable or disposable either on a periodic basis, e.g., a daily, weekly, monthly, as-needed, etc. basis, as may be suitable for the solution to be delivered. The reservoir may be prefilled and stored in a pharmacy or other suitable location for dispensing to users or filled at the pharmacy or elsewhere by using a suitable injection or fill means such as a hollow injection syringe driven manually or driven by a micro-pump. The syringe or fill means may fill the reservoir by pumping or filling fluid into or out of a rigid container or other collapsible or non-collapsible reservoir. In certain aspects, such disposable/replaceable, combination reservoir/ejector mechanism module may minimize and prevent buildup of surface deposits or surface microbial contamination on the aperture plate, owing to its short in-use time.

The droplet delivery device may be altitude insensitive. In certain implementations, the droplet delivery device is configured so as to be insensitive to pressure differentials that may occur when the user travels from sea level to sub-sea levels and/or high altitudes, e.g., while traveling in an airplane where pressure differentials may be as great as 4 psi. As will be discussed in further detail herein, in certain implementations of the disclosure, the droplet delivery device may include a superhydrophobic filter, optionally in combination with a spiral vapor barrier, which provides for free exchange of air into and out of the reservoir, while blocking moisture or fluids from passing into the reservoir, thereby reducing or preventing fluid leakage or deposition on aperture plate surfaces.

In certain embodiments, the droplet delivery device is comprised of a separate fluid delivery ampoule with an ejector mechanism embedded on a surface of the fluid reservoir, and a handheld unit containing a differential pressure sensor, a microprocessor and three AAA batteries. The microprocessor controls fluid delivery, delivery counting and software designed monitoring parameters that can be transmitted through wireless communication technology (e.g., Bluetooth, wifi, cellular, etc.). The piezoelectric ejector mechanism optimizes droplet delivery to the user by creating droplets in a predefined range with a high degree of accuracy and repeatability.

In certain aspects, the devices of the disclosure eliminate the need for patient/device coordination by using a differential pressure sensor to initiate the piezoelectric ejector mechanism in response to the onset of inhalation. The device does not require manual triggering of droplet delivery.

In certain embodiments, as described in further detail herein, when the fluid ampoule is mated to the handheld body, electrical contact is made between the base containing the batteries and the piezoelectric ejector embedded in the fluid reservoir. In certain embodiments, a horizontal series of three small, user visible LED lights and a small speaker within the handheld base provide user notifications. By way of example, the device may be, e.g., 3.5 cm high, 5 cm wide, 10.5 cm long and may weight approximately 95 grams with an empty drug ampoule and with batteries inserted.

As described herein, in certain embodiments, an easily accessible on/off slide bar activates the device and unseals the ejector mechanism face. One of the three LED lights will turn green and the number of remaining doses will be shown on the dose counter numerical display, indicating the unit is energized and ready to be used.

As the user inhales through the unit, the differential pressure sensor detects flow by measuring the pressure drop across a Venturi plate at the back of the mouthpiece. When the pressure decline (8 liters/minute) is attained, the microprocessor activates the piezoelectric ejector, at which point all three LEDs illuminate green, indicating that dosing has started. The microprocessor stops the ejector, e.g., 1.45 seconds after initiation (or at a designated time so as to achieve a desired administration dosage). In certain embodiments, as described in further detail herein, the device may then emit a positive chime sound after the initiation of dosing, indicating to the user to begin holding their breath for a designated period of time, e.g., 10 seconds. During the breath hold period, e.g., the three green LEDs may blink. Additionally, there may be voice commands instructing the patient on proper times to exhale, inhale and hold their breath.

The slide switch also opens (power on)/closes (power off) a sliding door on the handheld unit that seals the piezoelectric sprayer embedded in the drug cartridge. In the closed (off) state, the piezoelectric sprayer is sealed from airborne contamination and potential evaporative effects. The voice command and Instructions for Use will direct the user to slide the switch to the off position (door closed) at the end of use. If the unit has not been turned off, after 20 seconds of inactivity the user will be reminded to slide the door closed by lights and sounds.

Along with the aperture plate coatings described herein, several additional features of the device allow precise dosing of specific droplet sizes. Droplet size is set by the diameter of the holes in the aperture plate which are formed with high accuracy. By way of example, the holes in the aperture plate may range in size from 0.7 μm to 6 μm, from 0.7 μm to 5 μm, from 0.7 μm to 4.7 μm, from 0.7 μm to 4 μm, from 0.7 μm to 3 μm, from 0.7 μm to 2.5 μm, etc. Ejection rate, in droplets per second, is generally fixed by the frequency of the aperture plate vibration, e.g., 108-kHz, which is actuated by the microprocessor. In certain embodiments, there is less than a 50-millisecond lag between the detection of the start of inhalation and full droplet generation.

Droplet production within the respirable range occurs early in the inhalation cycle, thereby minimizing the amount of droplets being deposited in the mouth or upper airways at the end of an inhalation. The design of the droplet delivery device maintains constant fluid contact with the ejection mechanism, thus obviating the need for shaking and priming. The ejector door and vent configuration limit active agent or carrier evaporation to less than 150 μL to 350 μL per month. This avoids changes in active agent concentration due to evaporation that would change the amount of agent contained in the droplets.

The microprocessor in the device ensures exact timing and actuation of the piezoelectric element, and records the date-time of each ejection event as well as the user's inhalation flow rate during the dose inhalation. A numerical display on the handheld base unit may indicate the number of actuations remaining in the fluid cartridge. The base unit may sense when a new cartridge has been inserted based on the unique electrical resistance of each individual cartridge. Actuation counting and lockouts may also be preprogramed into the microprocessor.

The device may be constructed with materials currently used in FDA cleared devices. Manufacturing methods may be employed to minimize extractables.

By way of example, the aperture plate can formed of a metal, e.g., stainless steel, nickel, cobalt, titanium, iridium, platinum, or palladium or alloys thereof, and configured to achieve the desired contact angles as described herein. Alternatively, the aperture plate can be formed of suitable polymeric material, and be configured to achieve the desired surface contact angles, as described herein. By way of example, the aperture plate may be composed of a material selected from the group consisting of poly ether ether ketone (PEEK), polyimide, polyetherimide, polyvinylidine fluoride (PVDF), ultra-high molecular weight polyethylene (UHMWPE), nickel, nickel-cobalt, nickel-palladium, palladium, platinum, metal alloys thereof, and combinations thereof. Further, in certain aspects, the aperture plate may comprise a domed shape.

Any suitable material may be used to form the housing of the droplet delivery device. In particular embodiment, the material should be selected such that it does not interact with the components of the device or the fluid to be ejected (e.g., drug or medicament components). For example, polymeric materials suitable for use in pharmaceutical applications may be used including, e.g., gamma radiation compatible polymer materials such as polystyrene, polysulfone, polyurethane, phenolics, polycarbonate, polyimides, aromatic polyesters (PET, PETG), etc.

The fluid cartridge and reservoir may be constructed of any suitable materials for the intended use. In particular, the fluid contacting portions are made from material compatible with the desired agent(s). By way of example, in certain embodiments, the agent only contacts the inner side of the fluid reservoir and the inner face of the aperture plate and piezo drive. Wires connecting the piezoelectric ejector to the batteries contained in the base unit are embedded in the fluid ampoule shell to avoid contact with the fluid. The piezoelectric ejector is attached to the fluid reservoir by a flexible bushing. The bushing contacts the fluid and may be, e.g., any suitable material known in the art for such purposes such as those used in piezoelectric nebulizers. The piezoelectric actuator may be constructed from any suitable piezoelectric material suitable for medical application, including but not limited to lead zirconium titanate (PZT) and its modified ceramic materials. In certain embodiments, the piezo ceramic material may be sputter coated with a thin film coating of a precious metal or polymer on one or more surfaces. In certain embodiments, the piezo ceramic may be sputter coated on at least a surface fluid contact surface thereof, so as to minimize any interactions with the fluid to be delivered via the droplet deliver device.

The device mouthpiece, may be removable, replaceable and may be cleaned. Similarly, the device housing and fluid ampoule can be cleaned by wiping with a moist cloth. The aperture plate may be recessed into the ampoule and cannot be damaged without removing the ampoule from the base and directly striking the sprayer with a sharp object.

In certain aspects of the disclosure, an electrostatic coating may be applied to the one or more portions of the housing, e.g., inner surfaces of the housing along the airflow pathway such as the mouthpiece, to aid in reducing deposition of ejected droplets during use due to electrostatic charge build-up. Alternatively, one or more portions of the housing may be formed from a charge-dissipative polymer. For instance, conductive fillers are commercially available and may be compounded into the more common polymers used in medical applications, for example, PEEK, polycarbonate, polyolefins (polypropylene or polyethylene), or styrenes such as polystyrene or acrylic-butadiene-styrene (ABS) copolymers. Alternatively, in certain embodiments, one or more portions of the housing, e.g., inner surfaces of the housing along the airflow pathway such as the mouthpiece, may be coated with anti-microbial coatings, or may be coated with hydrophobic coatings to aid in reducing deposition of ejected droplets during use. Any suitable coatings known for such purposes may be used, e.g., polytetrafluoroethylene (Teflon).

Any suitable differential pressure sensor with adequate sensitivity to measure pressure changes obtained during standard inhalation cycles may be used, e.g., ±5 SLM, 10 SLM, 20 SLM, etc. For instance, pressure sensors from Sensirion. Inc., SDP31 or SDP32 (U.S. Pat. No. 7,490,511 B2) are particularly well suited for these applications.

In certain aspects, the microprocessor in the device may be programmed to ensure exact timing and actuation of the ejector mechanism in accordance with desired parameters, e.g., based duration of piezoelectric activation to achieve desired dosages, etc. In certain embodiments, the device includes or interfaces with a memory (on the device, smartphone, App, computer, etc.) to record the date-time of each ejection event, as well as the user's inhalation flow rate during the dose inhalation to facilitate user monitoring, as well as drug ampoule usage monitoring. For instance, the microprocessor and memory can monitor doses administered and doses remaining in a particular drug ampoule. In certain embodiments, the drug ampoule may comprise components that include identifiable information, and the base unit may comprise components that may "read" the identifiable information to sense when a drug ampoule has been inserted into the base unit, e.g., based on a unique electrical resistance of each individual ampoule, an RFID chip, or other readable microchip (e.g., cryptoauthentication microchip). Dose counting and lockouts may also be preprogramed into the microprocessor.

In certain embodiments of the present disclosure, the signal generated by the pressure sensors provides a trigger for activation and actuation of the ejector mechanism to thereby generate droplets and delivery droplets at or during a peak period of a patient's inhalation (inspiratory) cycle and assures optimum deposition of the plume of droplets and delivery of the composition into the respiratory system of the user.

In accordance with certain aspects of the disclosure, the droplet delivery device provides a reliable monitoring system that can date and time stamp actual delivery of substance, and record/store inspiratory airflow in a memory (on the device, smartphone, App, computer, etc.). Bluetooth or other wireless communication capabilities may then permit the wireless transmission of the data.

Wireless communication (e.g., Bluetooth, wifi, cellular, etc.) in the device may communicate date, time and number of actuations per session to the user's smartphone. Software programing can provide charts, graphics, medication reminders and warnings to patients and whoever is granted permission to the data. The software application will be able to incorporate multiple uses and users of the device (e.g. multiple substances, different users, etc.).

The device of the present disclosure is configured to dispense droplets during the correct part of the inhalation cycle, and can including instruction and/or coaching features to assist patients with proper device use, e.g., by instructing the holding of breath for the correct amount of time after inhalation. The device of the disclosure allows this dual functionality because it may both monitor air flow during the inhalation, and has internal sensors/controls which may detect the end of inhalation (based upon measured flow rate) and can cue the patient to hold their breath for a fixed duration after the inhalation ceases.

In one exemplary embodiment, a user may be coached to hold their breath with an LED that is turned on at the end of inhalation and turned off after a defined period of time (i.e., desired time period of breath hold), e.g., 10 seconds. Alternatively, the LED may blink after inhalation, and continue blinking until the breath holding period has ended. In this case, the processing in the device detects the end of inhalation, turns on the LEI) (or causes blinking of the LED, etc.), waits the defined period of time, and then turns off the LED. Similarly, the device can emit audio indications, e.g., one or more bursts of sound (e.g., a 50 millisecond pulse of 1000 Hz), verbal instructions to hold breath, verbal countdown, music, tune, melody, etc., at the end of inhalation to cue a patient to hold their breath for the during of the sound signals. If desired, the device may also vibrate during or upon conclusion of the breath holding period.

In certain embodiments, the device provides a combination of audio and visual methods (or sound, light and vibration) described above to communicate to the user when the breath holding period has begun and when it has ended. Or during the breath holding to show progress (e.g., a visual or audio countdown).

In other aspects, the device of the disclosure may provide coaching to inhale longer, more deeply, etc. The average peak inspiratory flow during inhalation (or dosing) can be utilized to provide coaching. For example, a patient may hear a breath deeper command until they reach 90% of their average peak inspiratory flow as measured during inspiration (dosing) as stored on the device, phone or in the cloud.

In addition, an image capture device, including cameras, scanners, or other sensors without limitation, e.g. charge coupled device (CCD), may be provided to detect and measure the ejected aerosol plume. These detectors, LED, delta P transducer, CCD device, all provide controlling signals to a microprocessor or controller in the device used for monitoring, sensing, measuring and controlling the ejection of a plume of droplets and reporting patient compliance, treatment times, dosage, and patient usage history, etc., via Bluetooth, for example.

In certain embodiments, the reservoir/cartridge module may include components that may carry information read by the housing electronics including key parameters such as ejector mechanism functionality, drug identification, and information pertaining to patient dosing intervals. Some information may be added to the module at the factory, and some may be added at the pharmacy. In certain embodiments, information placed by the factory may be protected from modification by the pharmacy. The module information may be carried as a printed barcode or physical barcode encoded into the module geometry (such as light transmitting holes on a flange which are read by sensors on the housing). Information may also be carried by a programmable or non-programmable microchip on the module which communicates to the electronics in the housing.

By way of example, module programming at the factory or pharmacy may include a drug code which may be read by the device, communicated via Bluetooth to an associated user smartphone and then verified as correct for the user. In the event a user inserts an incorrect, generic, damaged, etc., module into the device, the smartphone might be prompted to lock out operation of the device, thus providing a measure of user safety and security not possible with passive inhaler devices. In other embodiments, the device electronics can restrict use to a limited time period (perhaps a day, or weeks or months) to avoid issues related to drug aging or build-up of contamination or particulates within the device housing.

The droplet delivery device may further include various sensors and detectors to facilitate device activation, spray verification, patient compliance, diagnostic mechanisms, or as part of a larger network for data storage, big data analytics and for interacting and interconnected devices used for subject care and treatment, as described further herein. Further, the housing may include an LED assembly on a surface thereof to indicate various status notifications, e.g., ON/READY, ERROR, etc.

As described in further detail herein, the droplet delivery device of the disclosure may detect inspiratory airflow and record/store inspiratory airflow in a memory (on the device, smartphone, App, computer, etc.). A preset threshold (e.g., 8 L/min) triggers delivery of a composition over a defined period of time, e.g., 1.5 seconds. Inspiratory flow is sampled frequently until flow stops. The number of times that delivery is triggered is incorporated and displayed in the dose counter LED on the device. Wireless communication capabilities (e.g., Bluetooth, cellular, wifi, etc.) permit the wireless transmission of the data.

In certain aspects, the present disclosure relates to methods for delivering a fluid as an ejected stream of droplets to the respiratory system of a user using an ejector mechanism or droplet delivery device of the disclosure. In certain aspects, the methods are capable of delivering a defined volume of fluid in the form of an ejected stream of droplets such that an adequate and repeatable high percentage of the droplets are delivered into the desired location within the airways, e.g., the alveolar airways of the subject during use.

In certain embodiments, the methods of the disclosure may be used to treat various diseases, disorders and conditions by delivering agents to the respiratory system of a subject. In this regard, the ejector mechanisms and droplet delivery devices of the disclosure may be used to deliver therapeutic agents both locally to the respiratory system, and systemically to the body. In certain embodiments, the methods and droplet delivery devices of the disclosure may be used to treat epilepsy, seizure disorders, pain, chronic pain, neuropathic pain, headache, migraine, arthritis, multiple sclerosis, anorexia, nausea, vomiting, anorexia, loss of appetite, anxiety, insomnia, etc. In other embodiments, the methods and droplet delivery devices of the disclosure may be used to treat asthma, chronic obstructive pulmonary diseases (COPD), cystic fibrosis (CF), tuberculosis, chronic bronchitis, or pneumonia.

In certain embodiments, the methods and droplet delivery device may be used to deliver therapeutic agents such as COPD medications, asthma medications, or antibiotics. By way of non-limiting example, such therapeutic agents include albuterol sulfate, ipratropium bromide, tobramycin, fluticasone propionate, fluticasone furoate, tiotropium, glycopyrrolate, olodaterol, salmeterol, umeclidinium, and combinations thereof.

In certain embodiments, the methods and droplet delivery devices may be used to deliver a composition comprising a therapeutic agent for the treatment of asthma and/or COPD, including short acting and long acting bronchodilators, alone or in combination.

In other embodiments, the methods and droplet delivery device may be used for the local and/or systemic delivery of therapeutic agents including small molecules, therapeutic peptides, proteins, antibodies, and other bioengineered molecules via the respiratory system. By way of non-limiting example, the methods and droplet delivery device may be used to systemically deliver therapeutic agents for the treatment or prevention of indications inducing, e.g., diabetes mellitus, rheumatoid arthritis, plaque psoriasis, Crohn's disease, hormone replacement, neutropenia, nausea, influenza, etc.

By way of non-limiting example, therapeutic peptides, proteins, antibodies, and other bioengineered molecules include: growth factors, insulin, vaccines (Prevnor—Pneumonia, Gardasil—HPV), antibodies (Keytruda (pembrolizumab), Opdivo (nivolumab) Avastin (bevacizumab), Humira (adalimumab), Remicade (infliximab), Herceptin (trastuzumab)), Fc Fusion Proteins (Enbrel (etanercept), Orencia (abatacept)), hormones (Elonva—long acting FSH, Growth Hormone), enzymes (Pulmozyme—rHu-DNAase-), other proteins (Clotting factors, Interleukins, Albumin), gene therapy and RNAi, cell therapy (Provenge Prostate cancer vaccine), antibody drug conjugates—Adcetris (Brentuximab vedotin for HL), cytokines (Interferon-alpha, Interferon-beta), anti-infective agents, polynucleotides, oligonucleotides (e.g., gene vectors), or any combination thereof, or solid droplets or suspensions such as Flonase (fluticasone propionate) or Advair (fluticasone propionate and salmeterol xinafoate).

In other embodiments, the methods and droplet delivery devices of the disclosure may be used to deliver a solution of nicotine or a salt thereof, e.g., including the water-nicotine azeotrope. By way of non-limiting example, the nicotine or salt thereof may be the naturally occurring alkaloid compound having the chemical name S-3-(1-methyl-2-pyrrolidinyl)pyridine, which may be isolated and purified from nature or synthetically produced in any manner, or any of its occurring salts containing pharmacologically acceptable anions, such as hydrochloride, hydrobromide, hydroiodide, nitrate, sulfate or bisulfate, phosphate or acid phosphate, acetate, lactate, citrate or acid citrate, tartrate or bitartrate, succinate, maleate, fumarate, gluconate, pyruvate, saccharate, benzoate, methanesulfonate, ethanesulfonate, benzenesulfonate, p-toluene sulfonate, camphorate and pamoate salts. In other embodiments, the composition may further include any pharmacologically acceptable derivative, metabolite or analog of nicotine which exhibits pharmacotherapeutic properties similar to nicotine. Such derivatives and metabolites are known in the art, and include cotinine, norcotinine, nornicotine, nicotine N-oxide, cotinine N-oxide, 3-hydroxycotinine and 5-hydroxycotinine or pharmaceutically acceptable salts thereof.

In certain embodiments, the methods and droplet delivery devices may be used to deliver a composition comprising an agent that may isolated or derived from cannabis. For instance, the agent may be a natural or synthetic cannabinoid, e.g., THC (tetrahydrocannabinol), THCA (tetrahydrocannabinolic acid), CBD (cannabidiol), CBDA (cannabidiolic acid), CBN (cannabinol), CBG (cannabigerol), CBC (cannabichromene), CBL (cannabicyclol), CBV (cannabivarin), THCV (tetrahydrocannabivarin), CBDV (cannabidivarin), CBCV (cannabichromevarin), CBGV (cannabigerovarin), CBGM (cannabigerol monomethyl ether), CBE (cannabielsoin), CBT (cannabicitran), and various combinations thereof. In other embodiments, the agent may be a ligand that bind the cannabinoid receptor type 1 ($CB_1$), the cannabinoid receptor type 2 ($CB_2$), or combinations thereof. In particular embodiments, the agent may comprise THC, CBD, or combinations thereof. By way of example, the agent may comprise 95% THC, 98% THC, 99% THC, 95% CBD, 98% CBD, 99% CBD, etc.

In certain embodiments, the methods and drug delivery device of the disclosure may be used to deliver scheduled and controlled substances such as cannabinoids. In certain embodiments, by way of non-limiting example, dosing may only enabled by doctor or pharmacy communication to the device, only in a specific location such as the patient's residence as verified by GPS location on the patient's smart phone, and/or it may be controlled by monitoring compliance with dosing schedules, amounts, abuse compliances, etc. In certain aspects, this mechanism of highly controlled dispensing of controlled medications can prevent the abuse or overdose of controlled substances.

In all embodiments, the composition or solution may include various emulsifiers, surfactants, solubilizers, stabilizers, flavors, and other pharmaceutically acceptable carriers suitable for delivery to the respiratory system. By way of example, the compositions or solutions may include a non-ionic surfactant such as polyoxyethylene (20) sorbitan monooleate (polysorbate 80) to facilitate formulation of the therapeutic agent into the solution. The droplet delivery devices of the disclosure are particularly suited to provide delivery of droplets with a desired droplet size of such compositions.

In accordance with certain aspects of the disclosure, effective deposition into the lungs generally requires droplets less than about 5-6 μm in diameter. Without intending to be limited by theory, to deliver fluid to the lungs a droplet delivery device must impart a momentum that is sufficiently high to permit ejection out of the device, but sufficiently low to prevent deposition on the tongue or in the back of the throat. Droplets below approximately 5-6 μm in diameter are transported almost completely by motion of the airstream and entrained air that carry them and not by their own momentum.

In certain aspects, the present disclosure includes and provides an ejector mechanism configured to eject a stream of droplets within the respirable range of less than about 5-6 μm, preferably less than about 5 μm. The ejector mechanism is comprised of an aperture plate configured to provide a desired surface contact angle. The aperture plate is directly or indirectly coupled to a piezoelectric actuator. In certain implementations, the aperture plate may be coupled to an actuator plate that is coupled to the piezoelectric actuator. The aperture plate generally includes a plurality of openings formed through its thickness and the piezoelectric actuator directly or indirectly (e.g. via an actuator plate) oscillates the aperture plate, having fluid in contact with one surface of the aperture plate, at a frequency and voltage to generate a directed aerosol stream of droplets through the openings of the aperture plate into the lungs, as the patient inhales. In other implementations where the aperture plate is coupled to the actuator plate, the actuator plate is oscillated by the piezoelectric oscillator at a frequency and voltage to generate a directed aerosol stream or plume of aerosol droplets.

As discussed above, effective delivery of droplets deep into the lung airways require droplets that are less than about 5-6 microns in diameter, specifically droplets with mass mean aerodynamic diameters (MMAD) that are less than about 5 microns. The mass mean aerodynamic diameter is defined as the diameter at which 50% of the droplets by mass are larger and 50% are smaller. In certain aspects of the disclosure, in order to deposit in the alveolar airways, droplets in this size range must have momentum that is sufficiently high to permit ejection out of the device, but sufficiently low to overcome deposition onto the tongue (soft palate) or pharynx.

In other aspects of the disclosure, methods for generating an ejected stream of droplets for delivery to the respiratory system of user using the ejector mechanisms and droplet delivery devices of the disclosure are provided. In certain embodiments, the ejected stream of droplets is generated in a controllable and defined droplet size range. By way of example, the droplet size range includes at least about 50%, at least about 60%, at least about 70%, at least about 85%, at least about 90%, between about 50% and about 90%, between about 60% and about 90%, between about 70% and about 90%, etc., of the ejected droplets are in the respirable range of below about 5 μm, below about 4 μm, below about 3.7 μm, below about 3.5 μm, below about 3.2 μm, below about 3.0 μm, etc.

In other embodiments, the ejected stream of droplets may have one or more diameters, such that droplets having multiple diameters are generated so as to target multiple regions in the airways (mouth, tongue, throat, upper airways, lower airways, deep lung, etc.) By way of example, droplet diameters may range from about 1 μm to about 200 μm, about 2 μm to about 100 μm, about 2 μm to about 60 μm, about 2 μm to about 40 μm, about 2 μm to about 20 μm, about 1 μm to about 5 μm, about 1 μm to about 4.7 μm, about 1 μm to about 4 μm, about 10 μm to about 40 μm, about 10 μm to about 20 μm, about 5 μm to about 10 μm, and combinations thereof. In particular embodiments, at least a fraction of the droplets have diameters in the respirable range, while other droplets may have diameters in other sizes so as to target non-respirable locations (e.g., larger than 5 μm). Illustrative ejected droplet streams in this regard might have 50%-70% of droplets in the respirable range (less than about 5 μm), and 30%-50% outside of the respirable range (about 5 μm-about 10 μm, about 5 μm-about 20 μm, etc.)

In other aspects, the device of the disclosure may provide coaching to inhale longer, more deeply, etc. The average peak inspiratory flow during inhalation (or dosing) can be utilized to provide coaching. For example, a patient may hear a breath deeper command until they reach 90% of their average peak inspiratory flow as measured during inspiration (dosing) as stored on the device, phone or in the cloud.

EXAMPLES

Example 1

Ejector mechanisms with nickel-palladium alloy aperture plates were used to investigate the ability of aperture plates with controlled contact angles to eject small droplets. In general, native nickel-palladium alloy exhibit contact angles of about 90 degrees. Aperture plates formed from such nickel-palladium alloys generate efficient droplets in the respirable range, but not droplets in the small respirable range. Test aperture plates coated with hydrophilic surfaces on the fluid entrance surface in accordance with the disclosure were tested per the examples below. Results are summarized below.

Introduction

This study evaluated the aerosol characteristics of nicotine salt solutions using a test fixture to repeatedly emulate the behavior of a droplet delivery device of the disclosure. A single microfluidic ejector was used for all solutions tested. To determine the particle size distribution and mass median aerodynamic diameter (MMAD), the solutions were tested with an Aerodynamic Particle Sizer (APS) spectrometer. The target MMAD range was 1.0±0.3 μm.

Product Description

The droplet delivery device of the disclosure is comprised of a fluid cartridge (referred to as "cartridge") and an electronics unit (referred to as "base unit"). The cartridge contains a microfluidic ejector mechanism system designed to deliver a composition to the lungs by generating droplets with an average initial ejection diameter within a predefined range of optimal sizes. The base unit is comprised of a differential pressure sensor, microprocessor, wireless communication technology, and battery/power supply. The microprocessor in the droplet delivery device ensures the timing and actuation of the ejector mechanism system.

Particle Size Testing

An Aerodynamic Particle Sizer (APS) spectrometer model 3321 produced by Incorporated was used for evaluating the aerosol particle size by sampling the aerosol delivered by the test fixture. The APS measures true aerodynamic particle size similar to a cascade impactor, with a range of 0.35 μm to 20.0 μm.

Prior to each test, the test fixture was rinsed with deionized water. The test fixture was then filled with approximately 1 mL of the appropriate test solution.

The APS sample time was set to twenty (20) seconds for all conducted testing. Each actuation was 1.5 seconds.

The APS data was used to show the particle size distribution, mass median aerodynamic diameter (MMAD) and geometric standard deviation (GSD).

Formulations

A 1.5% nicotine solution (Lot #: 0605191Nic1.5%) and a 3% nicotine solution (Lot #: 060519Nic3%) were prepared by Aerosol Research and Engineering (ARE) Laboratories. The nicotine solutions were used to prepare two acidified nicotine salt solutions. A 1:1 M ratio solution was prepared by combining 3 mL of the 1.5% nicotine solution with 22.8 μL of 37% hydrochloric acid (HCl) from Sigma Aldrich (Lot #: STBH8903). Another 1:1 M ratio solution was prepared by combining 3 mL of the 3% nicotine solution with 45.6 μL of 37% HCl. The final pH values of the solutions were 7.09 and 7.49, respectively. The pH values of the solutions were measured with a Mettler Toledo pH meter (Model F20/LE438).

Separately, a 3% nicotine solution (Lot #: 060519Nic3%) was prepared by Aerosol Research and Engineering (ARE) Laboratories. An acidified nicotine salt solution (Pneuma nicotine formula PNF108) was prepared by adding 37% hydrochloric acid (HCl) from Sigma Aldrich (Lot #: STBH8903) to an aliquot of the 3% nicotine solution until a pH of 8.50 was reached. The pH value of the solution was measured with a Mettler Toledo pH meter (Model F20/LE438).

A 6% nicotine solution was also prepared by Pneuma Respiratory, Inc. An acidified nicotine salt solution (Pneuma nicotine formula) was prepared by adding 37% hydrochloric acid (HCl) from Sigma Aldrich to an aliquot of the 6% nicotine solution until a pH of 8.50 was reached. The pH value of the solution was measured with a Mettler Toledo pH meter (Model F20/LE438). Provides 3:1 ratio of freebase to nicotine salt with chlorine as the counter ion, with a nominal surface tension of 52.97±0.74 mN/m, a dynamic viscosity of 1.128 mPas (25° C.), and a kinematic viscosity of 1.124 $mm^2/s$ (25° C.).

Results

Table 1 shows a complete test matrix for all conducted testing.

TABLE 1

| Test matrix | | | | |
|---|---|---|---|---|
| Fixture Used | Solution Tested | Molar Ratio | Testing Performed | Equipment Used |
| Test fixture | 1.5% acidified nicotine salt solution | 1:1 | Particle size testing | TSI APS 3321 |
| Test fixture | 3% acidified nicotine salt solution | 1:1 | Particle size testing | TSI APS 3321 |
| Test fixture | 3% nicotine solution, pH 8.50 | | Particle size testing | TSI APS 3321 |
| Test fixture | 6% nicotine salt solution, pH 8.50 | 3:1 | Particle size testing | TSI APS 3321 |

Particle size testing was performed to evaluate the particle size distribution and MMAD of the microfluidic ejector using the indicated nicotine solutions. The solutions showed similar particle size distribution and MMAD values.

Figure 10:
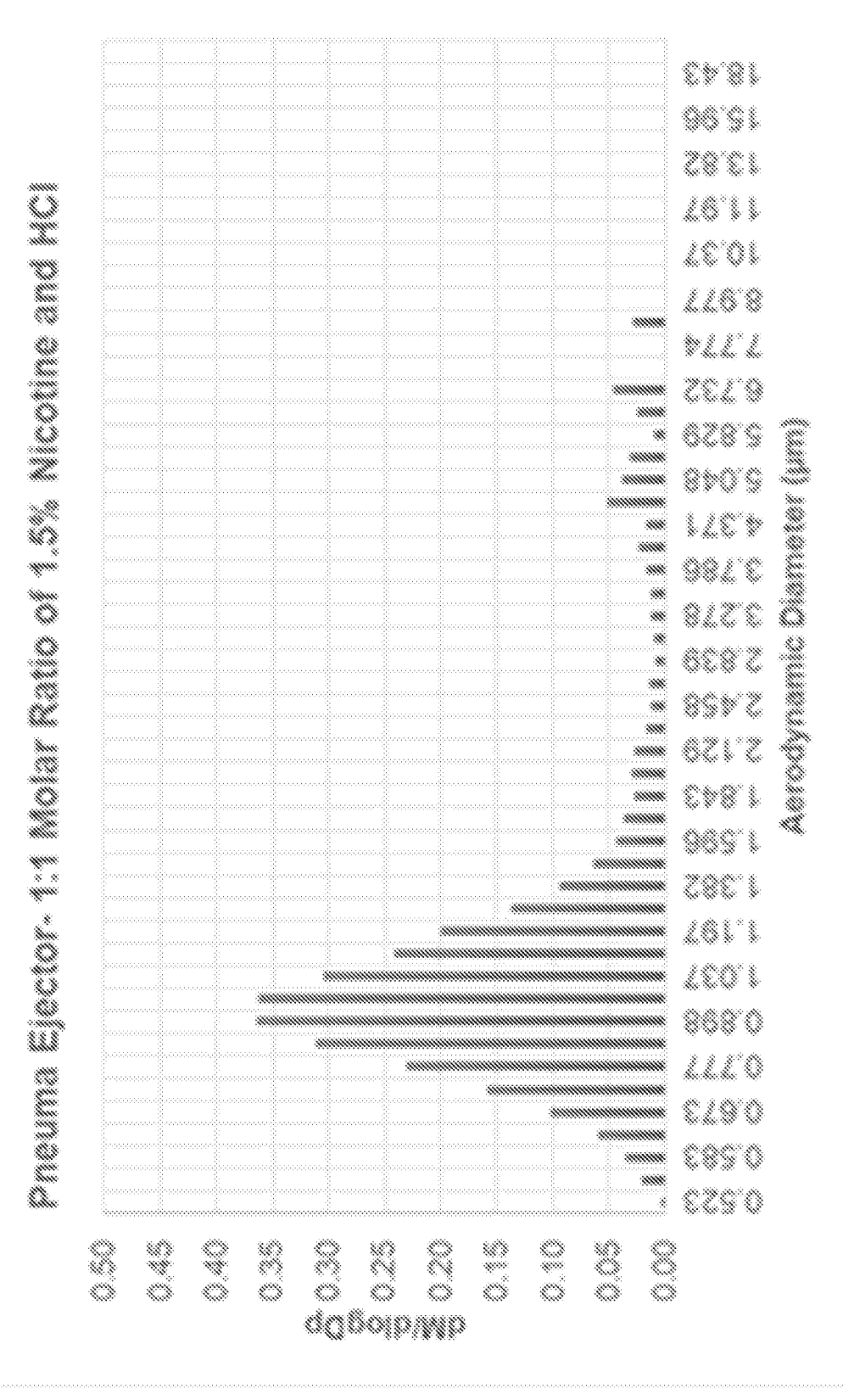
FIG. 10 shows the average particle size distribution for a 1.5% acidified nicotine salt solution generated using an ejector mechanism of the disclosure, in accordance with embodiments of the disclosure.
Figure 11:
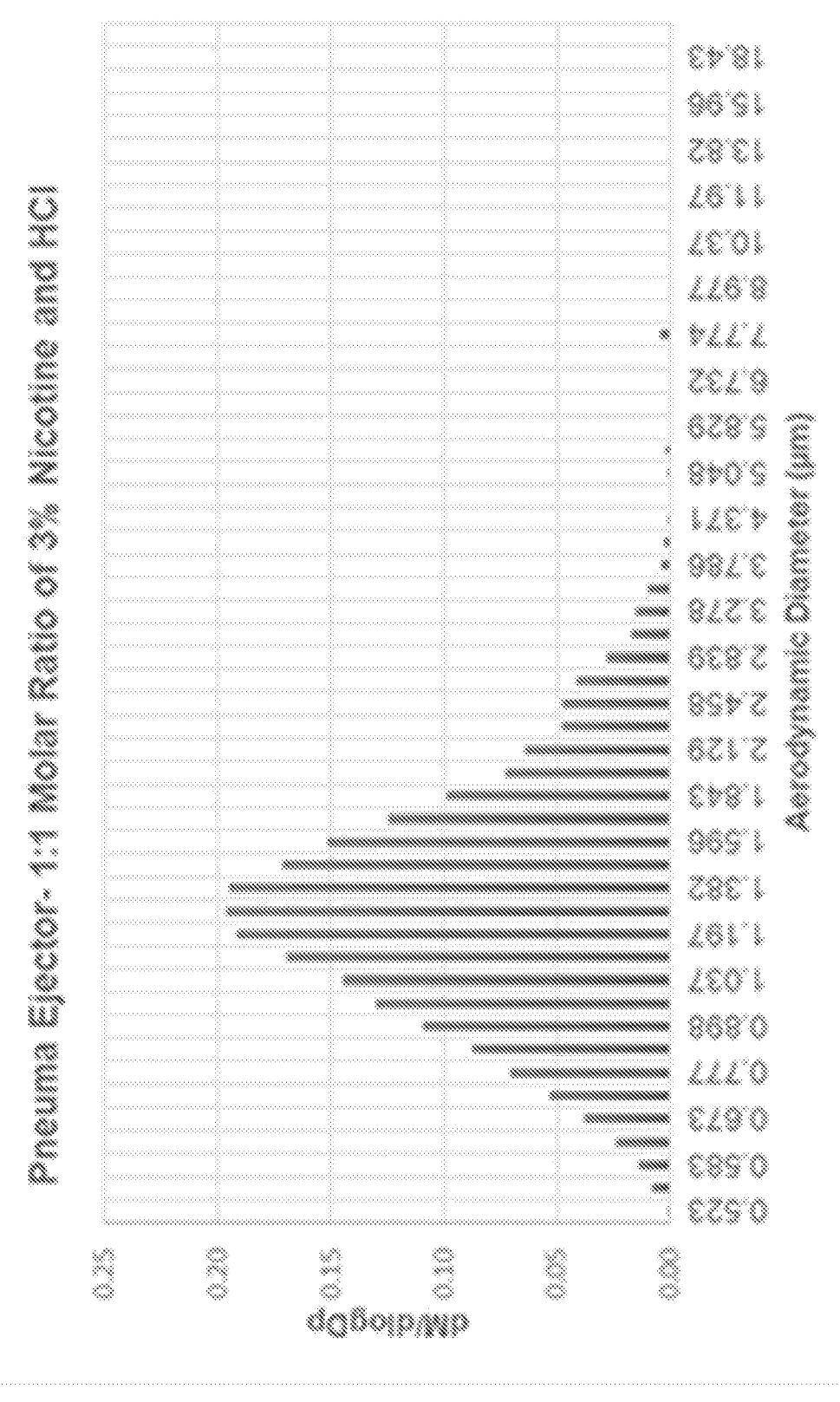
FIG. 11 shows the average particle size distribution for a 3% acidified nicotine salt solution generated using an ejector mechanism of the disclosure, in accordance with embodiments of the disclosure.
Figure 12:
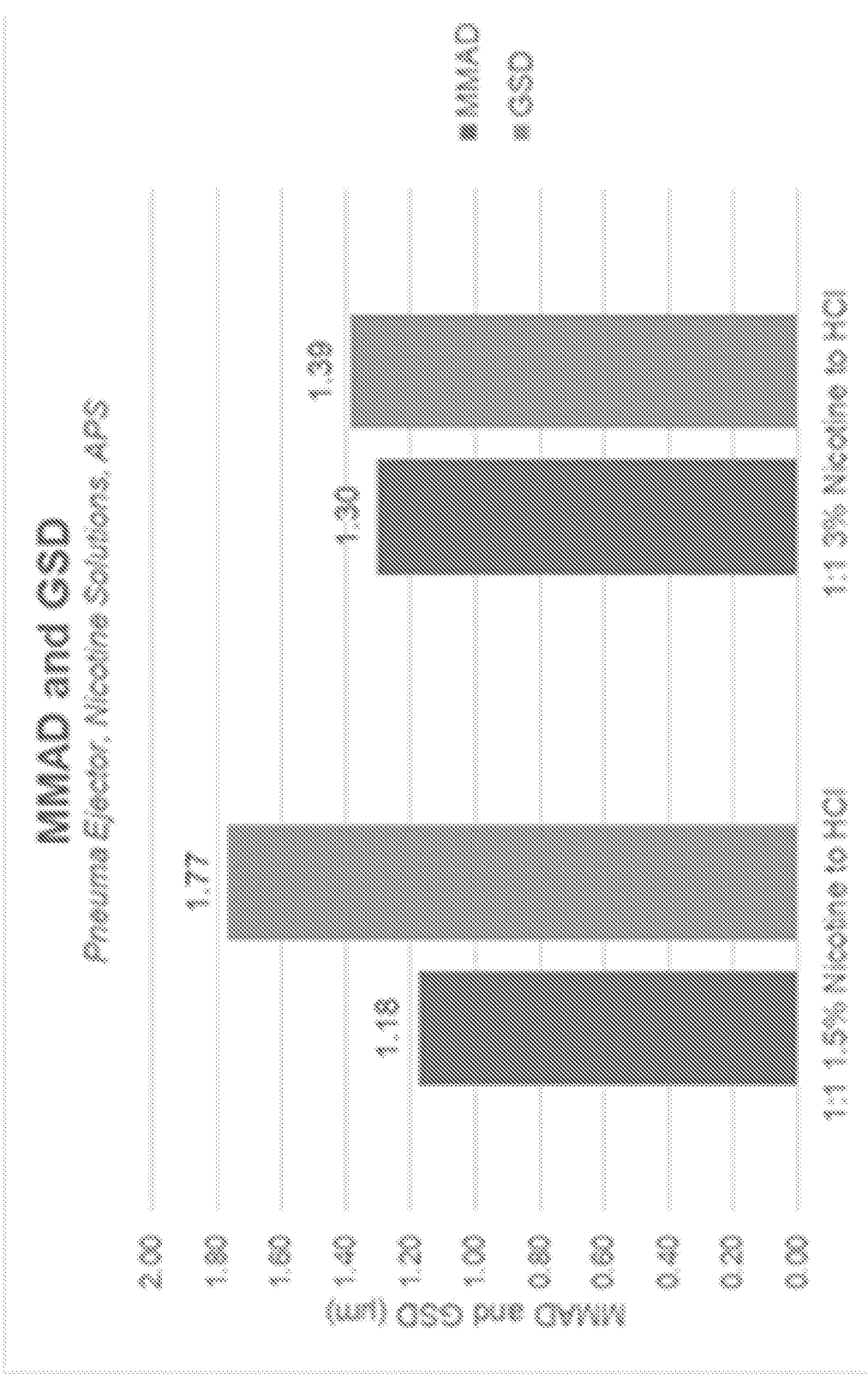
FIG. 12 shows the MMAD and GSD results for 1.5% and 3% acidified nicotine salt solutions using an ejector mechanism of the disclosure, in accordance with embodiments of the disclosure.

FIG. 10 shows the particle size distribution for the 1.5% acidified nicotine salt solution. FIG. 11 shows the particle size distribution for the 3% acidified nicotine salt solution. The MMAD of the 1.5% acidified nicotine salt solution was 1.18 μm, and the MMAD of the 3% acidified nicotine salt solution was 1.30 μm. The GSD of the 1.5% acidified nicotine salt solution was 1.77 μm, and the GSD of the 3% acidified nicotine salt solution was 1.39 μm. These results are shown graphically in FIG. 12 (MMAD and GSD results for 1.5% and 3% acidified nicotine salt solutions).

Figure 13:
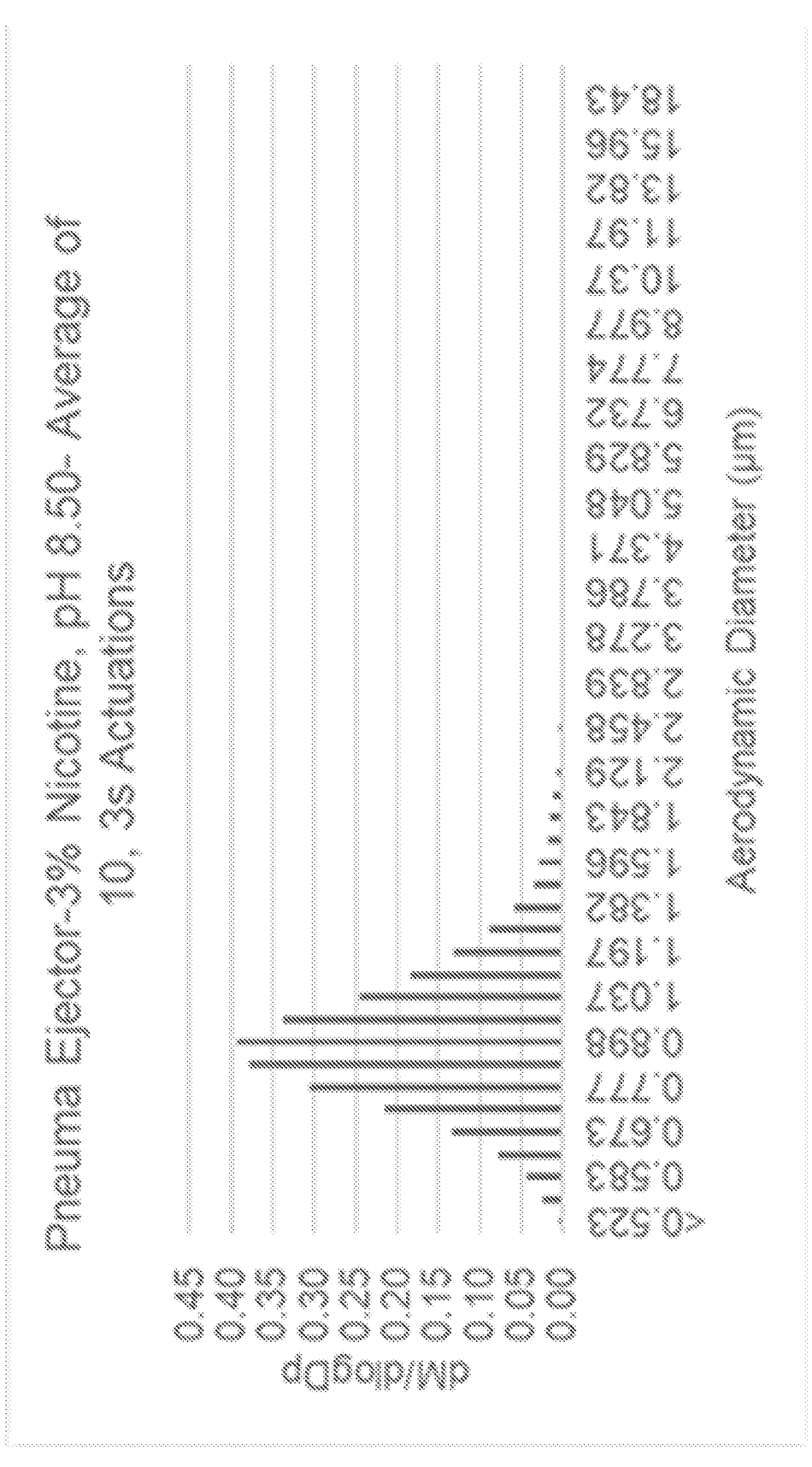
FIG. 13 shows the average particle size distribution from ten actuations of the 3% acidified nicotine salt solution (pH at 8.50) generated using an ejector mechanism of the disclosure, in accordance with embodiments of the disclosure.

FIG. 13 shows the average particle size distribution from ten actuations of the 3% acidified nicotine salt solution (pH at 8.50). Upon comparison to the results obtained from the 3% acidified nicotine salt solution (pH at 7.49, FIG. 11), the data obtained from the higher pH formulation shows a tighter distribution.

Figure 14:
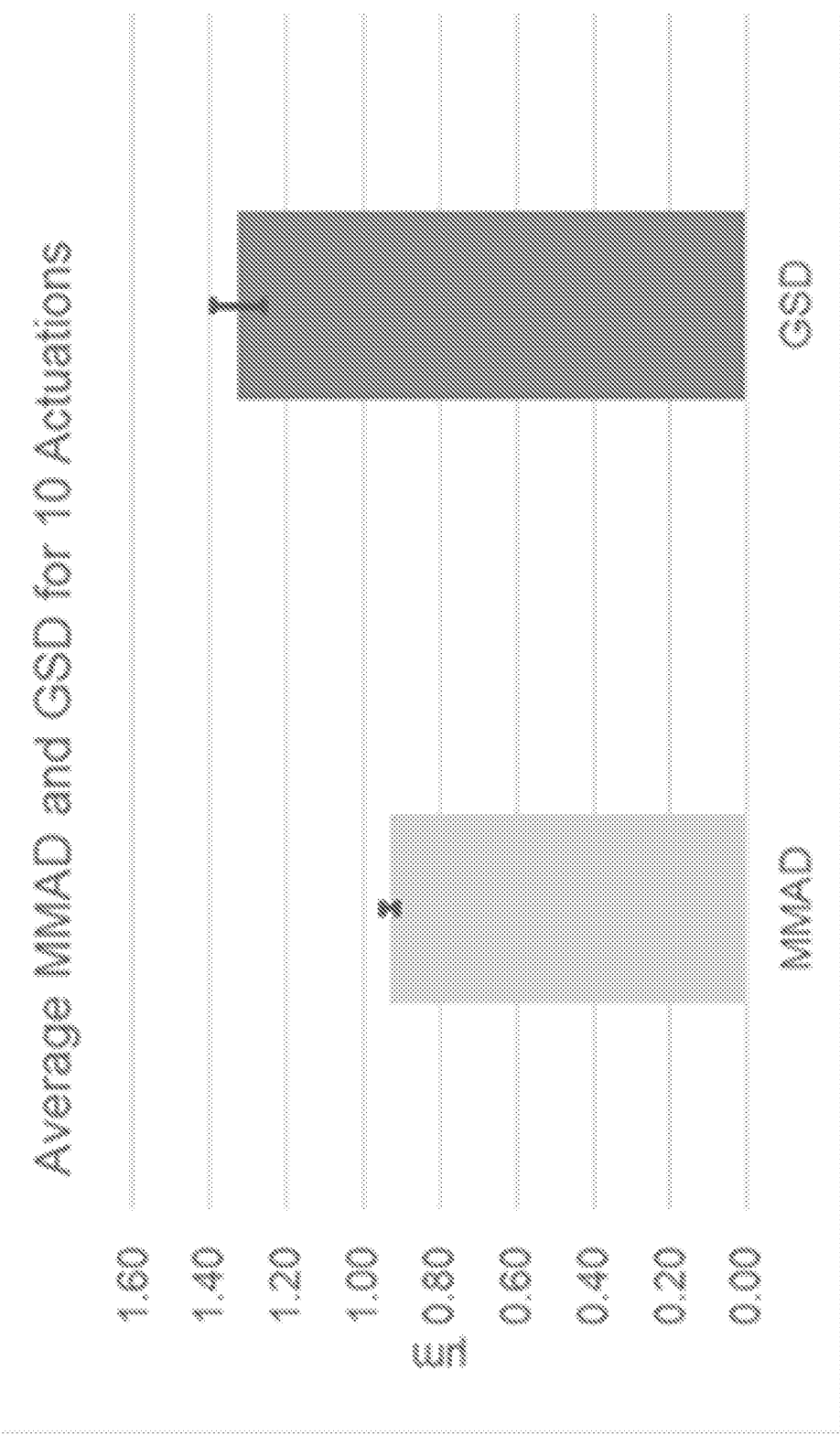
FIG. 14 shows the average MMAD and GSD results for 3% acidified nicotine sale solution (pH at 8.50), ten actuations of an ejector mechanism of the disclosure, in accordance with embodiments of the disclosure.

The average MMAD and GSD values of ten actuations of the 3% acidified nicotine salt solution (pH at 8.50) were 0.93±0.02 μm and 1.33±0.06 μm, respectively. These results are shown graphically in FIG. 14 (average MMAD and GSD results for 3% acidified nicotine salt solution (pH at 8.50), ten actuations). Upon comparison to the data obtained from the 3% acidified nicotine salt solution (pH at 7.49, FIG. 12), the higher pH formulation showed a smaller MMAD.

Figure 15:
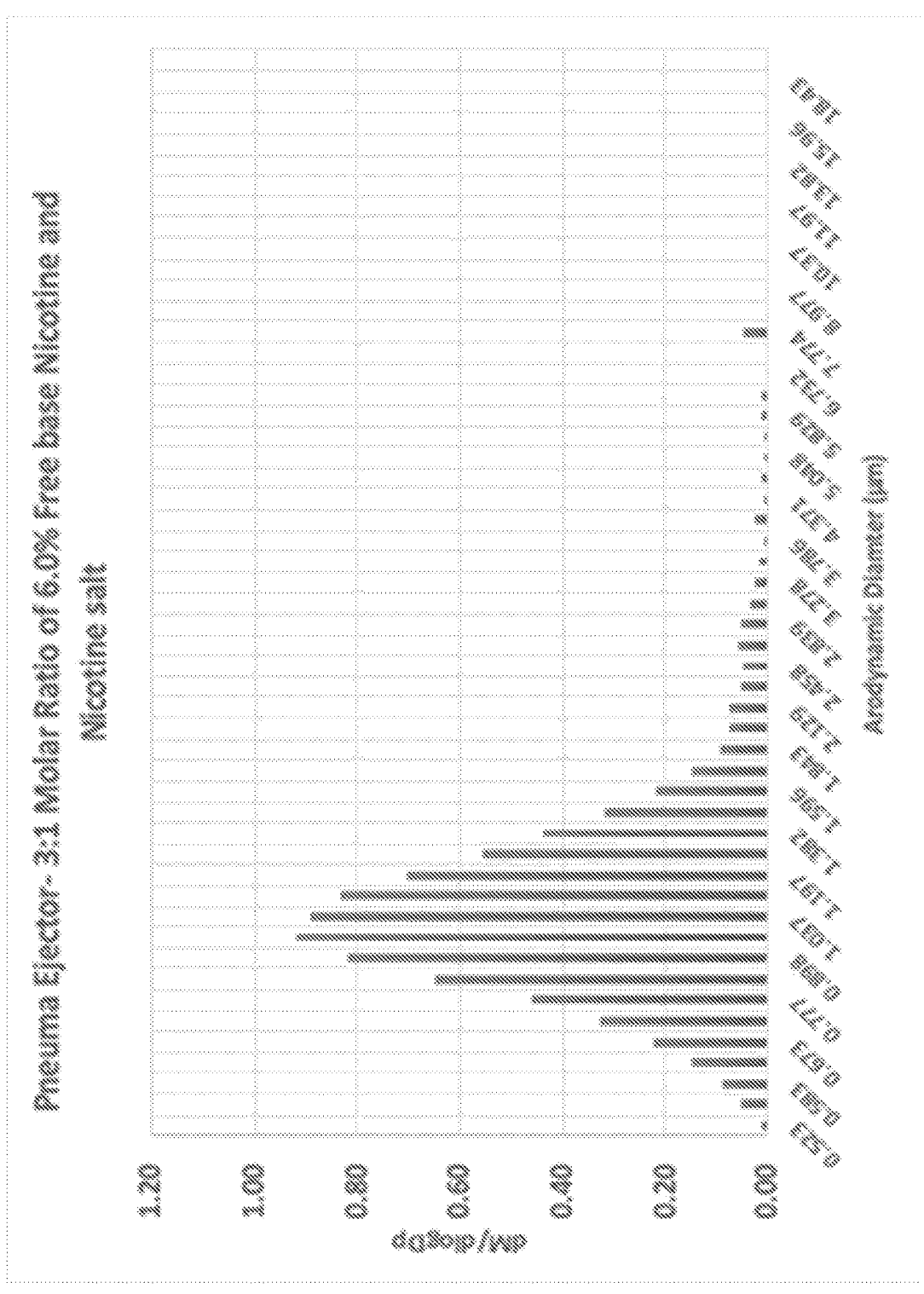
FIG. 15 shows the average particle size distribution from 6% nicotine, ten actuations of an ejector mechanism of the disclosure, in accordance with embodiments of the disclosure.
Figure 16:
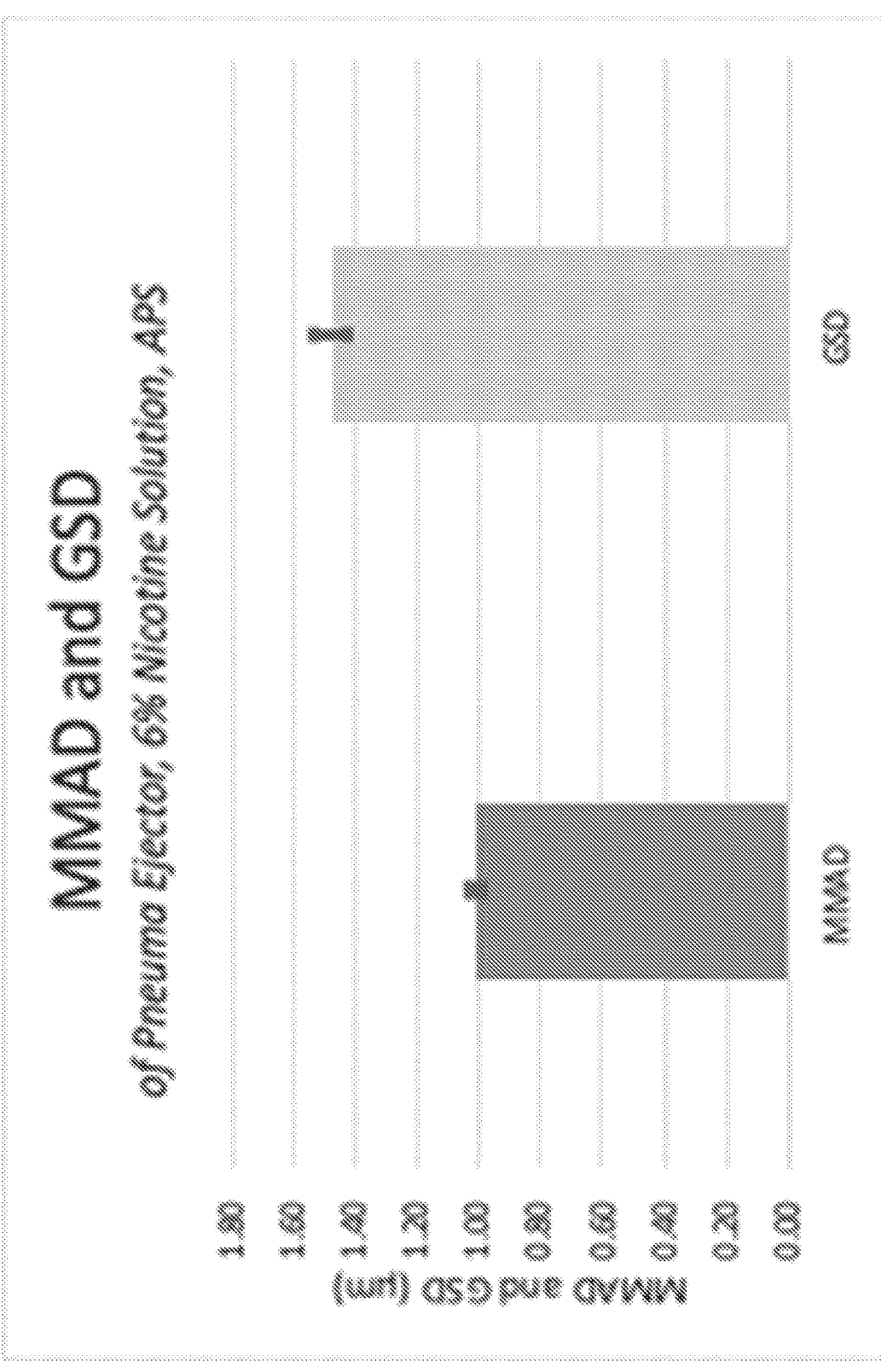
FIG. 16 show the average MMAD and GSD results for 6% nicotine solution, ten actuations of an ejector mechanism of the disclosure, in accordance with embodiments of the disclosure.

The concentration of a 6% (w/v) nicotine at a 3:1 molar ratio of freebase to nicotine salt was also analyzed. The average MMAD and GSD values of ten actuations of the formulation were 1.01±0.02 μm and 1.47±0.05, respectively. These results are shown graphically in FIG. 15 (average particle size distribution from 6% nicotine, ten actuations) and FIG. 16 (average MMAD and GSD results for 6% nicotine solution, ten actuations).

Conclusions

The 1.5% and 3% acidified nicotine solutions yielded MMAD values of 1.18 μm and 1.30 μm, respectively. The reported MMAD values are within the target range of 1.0±0.3 μm. An MMAD of 0.93±0.02 μm was obtained from the PNF108 formulation. The reported MMAD value is within the target range of 1.0±0.3 μm. The 6% nicotine solution resulted in an MMAD of 1.01±0.02 μm and a GSD of 1.47±0.05. Upon ten deep inhalations of the solution, no throat irritation was reported by two participants. Participant number one is a nonsmoker, while participant number two is a daily vape user. A noticeable nicotine effect was reported by both participants.

Example 2

Ejector mechanisms with nickel-palladium alloy aperture plates were used to investigate the effects of surface coatings with controlled contact angles on ejector mechanism aerosolization of small droplets. In general, native nickel-palladium alloy exhibit contact angles of about 90 degrees. Aperture plates formed from such nickel-palladium alloys generate efficient droplets in the respirable range, but not droplets in the small respirable range. Test aperture plates coated with various combinations of hydrophilic surfaces and hydrophobic surfaces in accordance with the aspects of the disclosure were tested per the examples below. Results are summarized below.

Materials and Methods

Attension Theta Lite Optical Tensiometer (Biolin Scientific)
FiveEasy F20 pH meter (Mettler Toledo)
Aerodynamic Particle Sizer Model 3321 (TSI)
Next Generation Impactor (Copley Scientific)
Vanquish UHPLC (ThermoFisher Scientific)
Accucore C18 column, 100 mm length, 3 mm I.D., particle size 2.6 μm (ThermoFisher Scientific)
Deionized water (Reagents)
Ultrapure water (Sigma Aldrich)
HPLC-grade methanol (Tedia)
(−)-Nicotine, ≥99% (Sigma Aldrich)

Benzoic acid, ≥99.5%, FCC, FG (Sigma Aldrich)
Potassium phosphate, ≥99% (Sigma Aldrich)
Tensiometer Measurements
A calibrated Theta Lite Optical Tensiometer was used to measure the contact angles of the devices illustrated in Table 2. A 3-4 μL drop of ultrapure water was placed on each side of the device. On the entrance side of the device, the drop was placed on the mesh, between the ceramic ring and the center depression. On the exit side of the piezo, the drop was placed on the ceramic ring. Images of the water droplet on the piezo were captured by the Theta Lite camera and accompanying software. The software, using the Young-Laplace model, fit a curve to the drop and calculated the contact angle between the water droplet and the surface of the piezo.
Nicotine Formulation
A 3% solution of nicotine was prepared by diluting 0.03 g/mL nicotine with ultrapure water. Benzoic acid was added to the nicotine solution in a 1:1 molar ratio. The solution was stirred until the benzoic acid completely dissolved. The pH of the solution was measured with a calibrated pH meter. The pH of the solution was adjusted as necessary to achieve a pH of 5.8-5.9. The nicotine solution was filtered and stored in dark conditions. 3.0% (w/v) of nicotine at a of 5.8. Nominal surface tension: 63.79±1.42 mN/m.
Next Generation Impactor (NGI)/HPLC Measurements
The flow rate of the NGI was set to 28.3 L/min. For each test, ten actuations were performed with a device to be measured at a volume of 4 L each. The NGI trays were extracted using a solution of three parts methanol to five parts ultrapure water. The extraction volumes were 5 mL for the smaller trays and 10 mL for the larger trays and induction port. The trays were agitated using a rocker for up to ten minutes. The induction port was stoppered and agitated.

After agitation, aliquots were obtained from each tray and the induction port. The aliquots were filtered with syringe filters (≤0.45 μm) into HPLC vials for analysis.

The aliquots from each tray were analyzed with an HPLC using an Accucore C18 column. The mobile phase was 35% potassium phosphate buffer (25 mM, pH 6.78) and 65% HPLC-grade methanol. A flow rate of 0.500 mL/min was used with a column temperature of 30° C. A UV detector was used with the HPLC at a wavelength of 260 nm. Nine standards with nicotine concentrations ranging from 1 μg/mL to 200 μg/mL were used to create a standard curve. The standard curve was used to calculate the concentration of nicotine in the trays and induction port based on the area of the signals produced by the UV detector.

Results are summarized in Tables 2, 3, and 4 below.

Results

Tables 2 and 3 illustrate the impact of surface coatings on droplet generation. As shown, a hydrophilic coating on at least the fluid entrance side surface of the aperture plate results in desirable MMAD along with a low throat fraction of droplet generation. These parameters further improve when the aperture plate is coated with a hydrophobic coating at the fluid exit side surface.

Without intending to be limited by theory, it is believed that coating hydrophobicity may be optimized based on solution surface tension and viscosity. As shown in Tables 3 and 4 below, when a solution having a lower surface tension is used in the same ejector configuration, the MMAD increases and the deposition in the throat section through stage 4 increases. Again, without intending to be limited by theory, this is believed to be due, at least in part, to lower surface tension in the solution increasing the height of the solution's meniscus in the ejector thereby resulting in larger droplet diameters. Stated another way, it is believed that higher surface tension leads to increased capillary action within the opening of the aperture place, which translates into a smaller droplet size. Again, this is illustrated through the demonstrated throat fraction ejections.

TABLE 2

| | | | | | | | µg/puff | | |
|---|---|---|---|---|---|---|---|---|---|
| Device ID | Surface Tension | Structure | Entrance | Exit | Total Mass Ejection | MMAD | (with throat) | Throat | Stage 1 |
| Uncoated | 63.75 | 3A | 90.00 | 90.00 | 1.74 | 1.856 | 52.125 | 20.229 | 4.595 |
| 3A-001 | 63.75 | 3A | 32.00 | 112.00 | 3.26 | 1.527 | 97.780 | 1.847 | 1.126 |
| 3A-002 | 63.75 | 3A | 33.00 | 112.00 | 3.48 | 1.565 | 104.418 | 1.959 | 1.605 |

| Device ID | Stage 2 | Stage 3 | Stage 4 | Throat | Stage 1 | Stage 2 | Stage 3 | Stage 4 |
|---|---|---|---|---|---|---|---|---|
| Uncoated | 1.332 | 0.449 | 2.086 | 38.81% | 8.82% | 2.56% | 0.86% | 4.00% |
| 3A-001 | 0.385 | 0.265 | 7.694 | 1.89% | 1.15% | 0.39% | 0.27% | 7.87% |
| 3A-002 | 0.517 | 0.355 | 10.786 | 1.88% | 1.54% | 0.50% | 0.34% | 10.33% |

TABLE 3

Coating Study

| Device | hole size | thickness | Entrance | Exit | MMAD | µg/puff (with throat) | µg/puff (w/o threat) | Throat µg (%) |
|---|---|---|---|---|---|---|---|---|
| | | | | Comparative | | | | |
| Native Uncoated Pd Ni | 1.8 | 32 | 90 | 90 | 1.856 | 52.125 | 31.897 | 20.229 (43.6) |
| | | | Hydrophilic Coating | | | | | |
| G2-004 | 1.4-1.6 | 26 | 14.65 | 5.1 | 1.477 | 86.523 | 84.363 | 2.161 (2.5) |
| G2-001 | 1.4-1.6 | 26 | 22 | 65 | 1.595 | 126.737 | 117.45 | 9.287 (7.3) |
| G2-002 | 1.4-1.6 | 26 | 37 | 63 | 1.497 | 54.046 | 47.571 | 6.475 (12.0) |
| G2-007 | 1.4-1.6 | 26 | 38.1 | 64.1 | 1.619 | 140.671 | 133.035 | 7.636 (5.4) |
| G2-006 | 1.4-1.6 | 26 | 40.8 | 64.2 | 1.462 | 86.712 | 83.851 | 2.861 (3.3) |
| G2-009 | 1.4-1.6 | 26 | 40.7 | 73.3 | 1.516 | 119.04 | 117.96 | 1.080 (0.9) |
| G2-003 | 1.4-1.6 | 26 | 49.5 | 51.1 | 1.573 | 108.434 | 101.17 | 7.264 (6.7) |
| G2-005 | 1.4-1.6 | 26 | 50.8 | 48.5 | 1.601 | 149.886 | 140.935 | 8.951 (6.0) |
| G2-008 | 1.4-1.6 | 26 | 53.6 | 54.3 | 1.596 | 293.973 | 125.311 | 168.662 (57.4) |
| H2-008 | 1.8 | 26 | 40.8 | 61.1 | 1.536 | 185.084 | 177.005 | 8.078 (4.4) |
| H2-004 | 1.8 | 26 | 47.4 | 32.2 | 1.719 | 123.277 | 119.222 | 4.055 (3.3) |
| H2-004 (6% nic, ST = 52, pH 8.50) | 1.8 | 26 | 47.4 | 32.2 | 1.964 | 248.69 | 233.4 | 15.290 (6.1) |
| H2-005 | 1.8 | 26 | 49.8 | 71.12 | 1.943 | 193.443 | 192.234 | 1.209 (0.6) |
| H2-006 | 1.8 | 26 | 52.8 | 49.2 | 1.892 | 169.691 | 156.46 | 13.431 (7.9) |
| H2-009 | 1.8 | 26 | 57.1 | 63.4 | 1.628 | 191.224 | 173.042 | 18.182 (9.5) |
| H2-010 | 1.8 | 26 | 60.3 | 73 | 1.578 | 106.108 | 104.725 | 1.383 (1.3) |
| H2-002 | 1.8 | 26 | 62.5 | 63 | 1.903 | 228.76 | 219.325 | 9.436 (4.1) |
| H2-003 | 1.8 | 26 | 64.9 | 51.3 | 1.892 | 169.891 | 156.46 | 13.431 (7.9) |
| H2-007 | 1.8 | 26 | 68.6 | 65.8 | 1.567 | 120.388 | 119.144 | 1.244 (1.0) |
| I5-006 | 1.8 | 27 | 17.9 | 43.9 | 1.505 | 131.694 | 122.201 | 9.493 (7.2) |
| I5-004 | 1.8 | 27 | 32.9 | 40.9 | 1.662 | 126.465 | 114.426 | 12.040 (9.5) |
| I5-012 | 1.8 | 27 | 44.1 | 60.8 | 1.567 | 208.976 | 201.448 | 7.528 (3.6) |
| I5-008 | 1.8 | 27 | 50.4 | 12.6 | 1.637 | 122.797 | 119.865 | 2.932 (2.4) |
| I5-002 | 1.8 | 27 | 54.9 | 48.9 | 1.353 | 219.595 | 210.082 | 9.512 (4.3) |
| I5-007 | 1.8 | 27 | 55.9 | 73.3 | 1.512 | 85.041 | 82.888 | 2.153 (25) |
| I5-009 | 1.8 | 27 | 62.1 | 75.3 | 1.551 | 129.209 | 121.628 | 7.581 (5.9) |
| I5-003 | 1.8 | 27 | 74.3 | 59.6 | 1.673 | 124.994 | 112.184 | 12.810 (102) |
| A2-003 Plasma coat: deposition hydrophilic | 1.9-2.1 | 26 | | | 1.872 | 42.955 | 32.958 | 9.997 (23.3) |
| L3-002 | 1.9-2.1 | 26 | 27 | 6 | 1.639 | 127.111 | 113.943 | 13.168 (10.4) |
| L3-005 | 1.9-2.1 | 26 | 18 | 11 | 1.63 | 120.976 | 110.335 | 10.642 (8.8) |
| | | | Hydrophilic and Hydrophobic Coatings | | | | | |
| N2-002 | 1.4-1.6 | 29 | 33 | 111 | 1.955 | 19.093 | 13.469 | 5.624 (29.5) |
| I4-003 | 1.8 | 27 | 20 | 122 | 1.633 | 149.667 | 148.516 | 1.151 (0.8) |
| I4-005 | 1.8 | 27 | 30 | 103 | 1.557 | 127.361 | 125.998 | 1.363 (1.1) |
| I4-006 | 1.8 | 27 | 32 | 112 | 1.527 | 97.78 | 95.933 | 1.847 (1.9) |
| I4-007 | 1.8 | 27 | 33 | 112 | 1.565 | 104.418 | 102.46 | 1.959 (1.9) |
| I4-007 (6% nic, ST = 52, pH 8.50) | 1.8 | 27 | 33 | 112 | 1.928 | 237.179 | 225.212 | 11.967 (5.0) |

TABLE 3-continued

Coating Study

| I4-001 | 1.8 | 27 | 37 | 116 | 1.518 | 122.185 | 108.848 | 13.337 (10.9) |
|---|---|---|---|---|---|---|---|---|
| I4-004 | 1.8 | 27 | 41 | 93 | 1.438 | 73.286 | 71.002 | 2.285 (3.1) |
| J2-005 | 1.9-2.1 | 26 | 28 | 118 | 1.479 | 165.392 | 149.766 | 15.626 (9.4) |
| J2-005-1.8s | 1.9-2.1 | 26 | | | 1.649 | 99.019 | 89.869 | 9.150 (9.2) |
| L2-005 | 1.9-2.1 | 26 | 32 | 107 | 1.847 | 205.403 | 197.471 | 7.932 (3.9) |
| L2-001 | 1.9-2.1 | 26 | 32 | 108 | 1.793 | 184.83 | 180.698 | 4.132 (2.2) |
| J2-001 | 1.9-2.1 | 26 | 33 | 94.4 | 1.686 | 166.469 | 148.564 | 17.905 (10.8) |
| J2-001 | 1.9-2.1 | 26 | 33 | 94.4 | 1.686 | 166.469 | 148.564 | 17.905 (10.8) |
| L2-002 | 1.9-2.1 | 26 | 36 | 116 | 1.837 | 175.824 | 171.87 | 3.954 (2.2) |
| L2-003 | 1.9-2.1 | 26 | 39 | 112 | 1.813 | 174.29 | 168.998 | 5.291 (3.0) |
| L2-004 | 1.9-2.1 | 26 | 41 | 101 | 1.77 | 159.559 | 154.07 | 5.502 (3.4) |
| L2-006 | 1.9-2.1 | 26 | 42 | 103 | 1.623 | 156.307 | 146.502 | 9.805 (6.3) |
| L2-009 | 1.9-2.1 | 26 | 43 | 110 | 1.526 | 99.26 | 96.231 | 3.029 (3.1) |
| J2-010 | 1.9-2.1 | 26 | 45 | 123 | 1.732 | 76.902 | 64.377 | 12.525 (16.3) |
| J2-008 | 1.9-2.1 | 26 | 46 | 125 | 1.636 | 97.756 | 92.813 | 4.944 (5.1) |
| K2-003 | 2.2 | 26 | 29 | 120 | 1.99 | 192.972 | 173.568 | 19.404 (10.1) |

| Device | Stage 1 µg (%) | Stage 2 µg (%) | Stage 3 µg (%) | Stage 4 µg (%) |
|---|---|---|---|---|
| Comparative | | | | |
| Native Uncoated Pd Ni | 4.595 (9.5) | 1.332 (2.55) | 0.449 (0.86) | 2.086 (4.1) |
| Hydrophilic Coating | | | | |
| G2-004 | 1.060 (1.2) | 0.278 (0.3) | 0.238 (0.3) | 6.464 (7.5) |
| G2-001 | 7.429 (5.9) | 3.556 (2.8) | 3.459 (2.7) | 11.043 (8.7) |
| G2-002 | 2.281 (4.2) | 0.721 (1.3) | 0.426 (0.8) | 2.399 (4.4) |
| G2-007 | 7.766 (5.5) | 3.518 (2.5) | 3.394 (2.4) | 10.915 (7.8) |
| G2-006 | 2.257 (2.6) | 1.161 (1.3) | 0.589 (0.7) | 4.635 (5.3) |
| G2-009 | 1.300 (1.1) | 0.406 (0.3) | 0.303 (0.3) | 8.616 (7.2) |
| G2-003 | 7.335 (6.8) | 3.466 (3.2) | 3.346 (3.1) | 7.436 (6.9) |
| G2-005 | 7.237 (4.8) | 3.517 (2.3) | 3.528 (2.4) | 14.192 (9.5) |
| G2-008 | 8.574 (2.9) | 3.846 (1.3) | 3.479 (1.2) | 10.351 (3.5) |
| H2-008 | 8.329 (4.5) | 3.895 (2.1) | 3.611 (2.0) | 16.242 (8.8) |
| H2-004 | 2.420 (2.0) | 1.034 (0.8) | 1.297 (1.1) | 18.577 (15.1) |
| H2-004 (6% nic, ST = 52, pH 8.50) | 11.079 (4.5) | 5.859 (2.4) | 9.656 (3.9) | 51.327 (20.6) |
| H2-005 | 1.407 (0.7) | 1.446 (0.7) | 8.026 (4.1) | 48.502 (25.1) |
| H2-006 | 3.200 (1.9) | 1.586 (0.9) | 6.238 (3.7) | 36.383 (21.4) |
| H2-009 | 10.788 (5.6) | 4.452 (2.3) | 3 816 (2.0) | 16.063 (8.4) |
| H2-010 | 0.769 (0.7) | 0.379 (0.4) | 0.673 (0.6) | 11.715 (11.0) |
| H2-002 | 8.375 (3.7) | 4.698 (2.1) | 9 811 (4.3) | 45.916 (20.1) |
| H2-003 | 3.200 (1.9) | 1.586 (0.9) | 6.238 (3.7) | 36.383 (21.4) |
| H2-007 | 1.417 (1.2) | 0.520 (0.4) | 0.372 (0.3) | 10.956 (9.1) |
| I5-006 | 8.095 (6.1) | 3.803 (2.9) | 3.464 (2.6) | 8.679 (6.6) |
| I5-004 | 7.751 (6.1) | 3.682 (2.9) | 3.561 (2.8) | 11.534 (9.1) |
| I5-012 | 7.739 (3.7) | 3.755 (1.8) | 4.287 (2.1) | 23.350 (11.2) |
| I5-008 | 2.235 (1.8) | 1.126 (0.9) | 0.789 (0.6) | 14.009 (11.4) |
| I5-002 | 8.157 (3.7) | 4.344 (2.0) | 7.514 (3.4) | 41.190 (18.8) |
| I5-007 | 1.646 (1.9) | 0.509 (0.6) | 0.272 (0.3) | 5.643 (6.6) |
| I5-009 | 7.481 (5.8) | 3.552 (2.7) | 3.387 (2.6) | 8.429 (6.5) |
| I5-003 | 9.313 (7.5) | 4.397 (3.5) | 3.642 (2.9) | 10.526 (8.4) |
| A2-003 Plasma coat: deposition hydrophilic | 3.428 (8.0) | 1.432 (3.3) | 0.885 (2.1) | 2.969 (6.9) |
| L3-002 | 4.894 (3.9) | 1.277 (1.0) | 0.879 (0.7) | 13.343 (10.5) |
| L3-005 | 3.229 (2.7) | 1.240 (1.0) | 0.569 (0.5) | 12.153 (10.0) |
| Hydrophilic and Hydrophobic Coatings | | | | |
| N2-002 | 2.675 (14.0) | 1.153 (6.0) | 0.557 (2.9) | 0.689 (3.6) |
| I4-003 | 1.406 (0.9) | 0.628 (0.4) | 1.396 (0.9) | 19.576 (13.1) |
| I4-005 | 0.991 (0.8) | 0.415 (0.3) | 0.374 (0.3) | 10.477 (8.2) |
| I4-006 | 1.126 (1.2) | 0.385 (0.4) | 0.265 (0.3) | 7.694 (7.9) |
| I4-007 | 1.605 (1.5) | 0.517 (0.5) | 0.355 (0.3) | 10.786 (10.3) |
| I4-007 (6% nic, ST = 52, pH 8.50) | 14.441 (6.1) | 6.657 (2.8) | 7.599 (3.2) | 43.585 (18.4) |
| I4-001 | 4.599 (3.8) | 1.097 (0.9) | 0.472 (0.4) | 8.913 (7.3) |
| I4-004 | 1.053 (1.4) | 0.284 (0.4) | 0.170 (0.2) | 3.032 (4.1) |
| J2-005 | 5.664 (3.4) | 1.262 (0.8) | 0.811 (0.5) | 12.765 (7.7) |

TABLE 3-continued

| Coating Study | | | | |
|---|---|---|---|---|
| J2-005-1.8s | 3.334 (3.4) | 0.689 (0.7) | 0.703 (0.7) | 10.783 (10.9) |
| L2-005 | 3.033 (1.5) | 1.557 (0.8) | 5.003 (2.4) | 43.555 (21.2) |
| L2-001 | 2.758 (1.5) | 1.404 (0.8) | 3.836 (2.1) | 35.238 (19.1) |
| J2-001 | 4.228 (2.5) | 0.966 (0.6) | 1.488 (0.9) | 21.838 (13.1) |
| J2-001 | 4.228 (2.5) | 0.966 (0.6) | 1.488 (0.9) | 21.838 (13.1) |
| L2-002 | 1.976 (1.1) | 1.017 (0.6) | 4.848 (2.8) | 37.906 (21.6) |
| L2-003 | 2.761 (1.6) | 1.309 (0.8) | 4.536 (2.6) | 33.292 (19.1) |
| L2-004 | 2.157 (1.4) | 0.937 (0.6) | 3.045 (1.9) | 28.331 (17.8) |
| L2-006 | 3.725 (2.4) | 1.172 (0.7) | 0.932 (0.6) | 17.203 (11.0) |
| L2-009 | 2.095 (2.1) | 0.519 (0.5) | 0.284 (0.3) | 6.725 (6.8) |
| J2-010 | 4.459 (5.8) | 1.138 (1.5) | 0.634 (0.8) | 7.169 (9.3) |
| J2-008 | 2.128 (2.2) | 0.965 (1.0) | 0.602 (0.6) | 10.436 (10.7) |
| K2-003 | 4.747 (2.5) | 1.836 (1.0) | 7.856 (4.1) | 45.881 (23.8) |

TABLE 4

Impact of Surface Tension on Droplet Generation (14-007 Device)

| Nicotine 1:1 | Surface tension | MMAD | Total Mass | Throat | Stage 1 | Stage 2 | Stage 3 | Stage 4 |
|---|---|---|---|---|---|---|---|---|
| 1.8% | 66.32 | 1.450 | 70.966 | 1.381 | 0.835 | 0.330 | 0.304 | 3.858 |
| 3.0% | 63.35 | 1.565 | 104.418 | 1.959 | 1.605 | 0.517 | 0.355 | 10.786 |
| 5.0% | 60.26 | 1.747 | 125.237 | 4.136 | 1.862 | 0.633 | 0.818 | 19.833 |
| | | | | Freebase | | | | |
| 6.0% | 52.28 | 1.928 | 237.179 | 11.967 | 14.441 | 6.657 | 7.599 | 43.585 |

Example 3

Ejector mechanisms with nickel-palladium alloy aperture plates were used to investigate the effects of surface treatment to provide surface roughening with controlled contact angles on ejector mechanism aerosolization of small droplets. In general, native nickel-palladium alloy exhibit contact angles of about 90 degrees. Aperture plates formed from such nickel-efficient droplets in the respirable range, but not droplets in the small respirable range. Test NiPd aperture plates were sputtered with thin film Pd (no sputter, 30 nm sputter, 80 nm sputter), and then etched to provide surface roughness and desired surface contact angles. Aperture plates were etched at a low, medium, and high etching power (1x, 2x, 3x at the high power level). The ejector mechanisms were tested per the examples below. Results are summarized in the tables below.

TABLE 5

No Palladium Sputter; 1X at high etch power

| Ejector | Hole Size | Entrance Contact Angle sputter on entrance | Exit Contact Angle | Mass Ejection |
|---|---|---|---|---|
| Etch-1H-1-001 | 1.523 | 77.6 | Native | 80.6 |
| Etch-1H-1-002 | 1.63 | 75.5 | Native | 171 |
| Etch-1H-1-003 | 1.808 | 79 | Native | 54.4 |
| Etch-1H-1-004 | 1.88 | 58.8 | Native | |
| Etch-1H-1-005 | 1.624 | 70.3 | Native | |
| Etch-1H-1-006 | 1.539 | 89.4 | Native | |
| Etch-1H-1-007 | 1.633 | 89.8 | Native | |
| Etch-1H-1-008 | 1.848 | 68.9 | Native | |
| Etch-1H-1-009 | 1.847 | 68.9 | Native | |
| Etch-1H-1-010 | 1.824 | 71.7 | Native | |
| Average | 1.716 | 74.99 | | 102 |

TABLE 6

No Palladium Sputter; 3X at high etch power

| Ejector | Hole Size | Entrance Contact Angle sputter on entrance | Exit Contact Angle | Mass Ejection |
|---|---|---|---|---|
| Etch-3H-1-001 | 1.746 | 76.2 | Native | 89 |
| Etch-3H-1-002 | 1.747 | 61.6 | Native | 41 |
| Etch-3H-1-003 | 1.779 | 69.5 | Native | 89.5 |
| Etch-3H-1-004 | 1.797 | 63.9 | Native | 86.8 |
| Etch-3H-1-005 | 1.803 | 70.1 | Native | |
| Etch-3H-1-006 | 1.807 | 65.5 | Native | |
| Etch-3H-1-007 | 1.751 | 71.9 | Native | |
| Etch-3H-1-008 | 1.621 | 63.8 | Native | |
| Etch-3H-1-009 | 1.903 | 73.8 | Native | |
| Etch-3H-1-010 | 1.951 | 67.8 | Native | |
| Average | 1.791 | 68.41 | | 76.575 |

TABLE 7

30 nm thick Palladium; Low etch power

| Ejector | Entrance Contact Angle sputter on entrance | Exit Contact Angle |
|---|---|---|
| Psput-low-30-1-01 | 87.0 | Native |
| Psput-low-30-1-02 | 83.5 | Native |
| Average | 85.3 | |

TABLE 8

| | 30 nm thick Palladium; Medium etch power | |
|---|---|---|
| Ejector | Entrance Contact Angle | Exit Contact Angle |
| | sputter on entrance | |
| Psput-med-30-1-01 | 79.8 | Native |
| Psput-med-30-1-02 | 78.7 | Native |
| Average | 79.3 | |

TABLE 9

| | 30 nm thick Palladium; 1X at high etch power | |
|---|---|---|
| Ejector | Eutrance Contact Angle | Exit Contact Angle |
| | sputter on entrance | |
| Psput-high-30-1-01 | 72.1 | Native |
| Psput-high-30-1-02 | 67.8 | Native |
| Average | 70.0 | |

TABLE 10

| | 80 nm thick Palladium; Low etch power | |
|---|---|---|
| Ejector | Entrance Contact Angle | Exit Contact Angle |
| | sputter on entrance | |
| Psput-low-80-1-01 | 85.8 | Native |
| Psput-low-80-1-02 | 85.8 | Native |
| Average | 85.8 | |

TABLE 11

| | 80 nm thick Palladium; Medium etch power | |
|---|---|---|
| Ejector | Entrance Contact Angle | Exit Contact Angle |
| | sputter on entrance | |
| Psput-med-80-1-01 | 91.9 | Native |
| Psput-med-80-1-02 | 88.6 | Native |
| Average | 90.25 | |

TABLE 12

| | 80 nm thick Palladium; 1X at high etch power | |
|---|---|---|
| Ejector | Entrance Contact Angle | Exit Contact Angle |
| | sputter on entrance | |
| Psput-high-80-1-01 | 88.9 | Native |
| Psput-high-80-1-02 | 96.2 | Native |
| Average | 92.55 | |

TABLE 13

| | 80 nm thick Palladium; 1X at high etch power | | | |
|---|---|---|---|---|
| Ejector | Hole Size | Entrance Contact Angle | Exit Contact Angle | Mass Ejection |
| | | sputter on entrance | | |
| Psput-1high-80-1-01 | 1.965 | 74.1 | Native | 158.6 |
| Psput-1high-80-1-02 | 2.069 | 70.2 | Native | 123.1 |
| Psput-1high-80-1-03 | 1.756 | 76 | Native | 160.4 |
| Psput-1high-80-1-04 | 2.016 | 78.2 | Native | 106.5 |
| Psput-1high-80-1-05 | 1.829 | 85.3 | Native | |
| Average | 1.9 | 76.8 | | 137.15 |
| | | sputter on both entrance and exit | | |
| Psput-1high-80-2-01 | 1.609 | 64.8 | 90.5 | NA |
| Psput-1high-80-2-02 | 1.498 | 69 | 109 | NA |
| Psput-1high-80-2-03 | 1.413 | 74.3 | 79.4 | NA |
| Psput-1high-80-2-04 | | 72 | 71.8 | NA |
| Psput-1high-80-2-05 | 1.411 | 75.1 | 72.4 | NA |
| Average | 1.5 | 71.0 | 84.6 | |

TABLE 14

| | 80 nm thick Palladium; 2X at high etch power | | | |
|---|---|---|---|---|
| Ejector | Hole Size | Entrance Contact Angle | Exit Contact Angle | Mass Ejection |
| | | sputter on entrance | | |
| Psput-2high-80-1-01 | 2.143 | 60.3 | Native | 30.4 |
| Psput-2high-80-1-02 | 1.981 | 73.1 | Native | 133 |
| Psput-2high-80-1-03 | 2.094 | 72.1 | Native | 162.1 |
| Psput-2high-80-1-04 | 1.887 | *7 | Native | 152.9 |
| Psput-2high-80-1-05 | 1.862 | 95.1 | Native | 86.7 |
| Average | 1.993 | 70.1 | | 113.02 |
| | | sputter on both entrance and exit | | |
| Psput-2high-80-2-01 | 1.691 | 57.9 | 89.1 | |
| Psput-2high-80-2-02 | 1.405 | 75.3 | 87.4 | 74.9 |
| Psput-2high-80-2-03 | 1.531 | 67.2 | 93.4 | 100.7 |
| Psput-2high-80-2-04 | 1.53 | 72.1 | 84.4 | 111.8 |
| Psput-2high-80-2-05 | 1.443 | 72.3 | 73.3 | 90 |
| Average | 1.520 | 69.0 | 78.9 | 94.4 |

TABLE 15

| | 80 nm thick Palladium; 3X at high etch power | | | |
|---|---|---|---|---|
| Ejector | Hole Size | Entrance Contact Angle | Exit Contact Angle | Mass Ejection |
| | | sputter on entrance | | |
| Psput-3high-80-1-01 | 1.839 | 76.3 | Native | 83.5 |
| Psput-3high-80-1-02 | 2.008 | 65.3 | Native | 155.3 |
| Psput-3high-80-1-03 | 1.836 | 62.5 | Native | 103.1 |
| Psput-3high-80-1-04 | 2.093 | 71.4 | Native | 197.5 |
| Psput-3high-80-1-05 | 2.226 | 62 | Native | 283.7 |
| Psput-3high-80-1-06 | 1.831 | 47 | Native | 193.8 |
| Psput-3high-80-1-07 | 2.274 | 59.6 | Native | 87.6 |
| Psput-3high-80-1-08 | 2.135 | 65.1 | Native | 229.8 |
| Psput-3high-80-1-09 | 1.875 | 59.4 | Native | 187.7 |
| Psput-3high-80-1-10 | 1.847 | 56.3 | Native | 44.8 |
| Psput-3high-80-1-11 | 2.122 | 72.5 | Native | 120.7 |
| Psput-3high-80-1-12 | 1.918 | 62.9 | Native | 42.3 |
| Psput-3high-80-1-13 | 1.925 | 62.3 | Native | 134.2 |
| Psput-3high-80-1-14 | 1.966 | 66.1 | Native | 199.7 |
| Psput-3high-80-1-15 | 1.922 | 61.6 | Native | 134.7 |
| Psput-3high-80-1-16 | 1.993 | 61.5 | Native | 254.8 |
| Psput-3high-80-1-17 | 1.831 | 67.1 | Native | 114.8 |
| Psput-3high-80-1-19 | 1.967 | 68.0 | Native | 187.3 |
| Psput-3high-80-1-20 | 2.044 | 66.7 | Native | 177.2 |
| Psput-3high-80-1-21 | 2.131 | 69.1 | Native | 167.9 |

TABLE 15-continued

| | | 80 nm thick Palladium; 3X at high etch power | | |
|---|---|---|---|---|
| Ejector | Hole Size | Entrance Contact Angle | Exit Contact Angle | Mass Ejection |
| Psput-3high-80-1-22 | 2.233 | 60.3 | Native | 240 |
| Psput-3high-80-1-23 | 1.981 | 59.7 | Native | 191 |
| Psput-3high-80-1-24 | 2.094 | 70.0 | Native | 251.6 |
| Psput-3high-80-1-25 | 2.098 | 65.5 | Native | 246.8 |
| Average | 2.096 | 67.8 | | 167.9 |
| | | sputter on both entrance and exit | | |
| Psput-3high-80-2-01 | 1.172 | 56 | 79 | 28 |
| Psput-3high-80-2-02 | 1.589 | 46 | 72 | 233.6 |
| Psput-3high-80-2-03 | 1.348 | 67.3 | 104 | 82 |
| Psput-3high-80-2-04 | 1.469 | 56 | 120 | 75.1 |
| Psput-3high-80-2-05 | 1.618 | 61 | 81 | 69.5 |
| Average | 1.544 | 58.5 | 100.5 | 72.3 |

As can be seen in the tables above, non-chemical etching was able to control and achieve hydrophilic surface contact angles at the fluid entrance side of less than 80 degrees, less than 70 degrees, less than 60 degrees, less than 55 degrees, etc., and was able to modify the surface contact angle at the fluid exit surface. Droplet ejection diameters in the range of approximately 1-2 microns were achieved, as was high mass ejection.

Example 4

This study evaluated the aerosol characteristics of compositions comprising a surfactant (polysorbate 80) using a test fixture to repeatedly emulate the behavior of a droplet delivery device of the disclosure. A single microfluidic ejector was used for all solutions tested. To determine the particle size distribution and mass median aerodynamic diameter (MMAD), the solutions were tested with an Aerodynamic Particle Sizer (APS) spectrometer. The target MMAD range was 1.0±0.3 µm.

Product Description

The droplet delivery device of the disclosure is comprised of a fluid cartridge (referred to as "cartridge") and an electronics unit (referred to as "base unit"). The cartridge contains a microfluidic ejector mechanism system designed to deliver a composition to the lungs by generating droplets with an average initial ejection diameter within a predefined range of optimal sizes. The base unit is comprised of a differential pressure sensor, microprocessor, wireless communication technology, and battery/power supply. The microprocessor in the droplet delivery device ensures the timing and actuation of the ejector mechanism system.

Particle Size Testing

An Aerodynamic Particle Sizer (APS) spectrometer model 3321 produced by TSI Incorporated was used for evaluating the aerosol particle size by sampling the aerosol delivered by the test fixture. The APS measures true aerodynamic particle size similar to a cascade impactor, with a range of 0.35 µm to 20.0 µm. Testing was performed at a flow rate of 5 lpm.

Instrumentation

TSI Incorporated Aerodynamic Particle Sizer (APS) Spectrometer 3321; TSI Incorporated Aerosol Diluter 3302A with dilution ratio of 100:1; TSI Incorporated Aerosol Diluter 3302A with dilution ratio of 20:1; Mettler Toledo X5204 Analytical balance.

Testing Conditions

Approximately 2 mls of test compositions were filled into test device reservoir 3 second ejections 5 individual shots were taken for each ejector and surfactant percentage/formulation The data was averaged together, and the standard deviation was determined If one data point fell far outside the standard it was ignored Samples were collected at ambient temperature and ≥50% humidity Formulations Formulations Tested Formulation 1: 1% polysorbate 80 (w/v) dissolved in 0.9% (w/v) NaCl and having a surface tension of 47.03 mN/m Formulation 2: 10% polysorbate 80 (w/v) dissolved in 0.9% (w/v) NaCl and having a surface tension of 45.8 nN/m Reagents Reagents Deionized Water, ACS Reagent, ASTM Type I Polysorbate 80 (W291706-1KG-K) Sigma-Aldrich Sodium Chloride (S1679-500G) Sigma-Aldrich Ejector Data: Contact Angles NiPd aperture plates were sputter coated with 80 nm of palladium, and etched (3× at high power etch) to obtain the below indicated surface contact angles.

D01-1.7T-033 (1.7 micron exit hole diameter, entrance openings between 20-30 microns with taper from entrance to exit)

Entrance—80 degrees

Exit—100 degrees

D01-2.0T-048 (2.0 exit hole diameter, entrance openings between 20-30 microns with taper from entrance to exit)

Entrance—53 degrees

Exit—88 degrees

D01-3.5T-003 (3.5 exit hole diameter, entrance openings between 20-30 microns with taper from entrance to exit)

Entrance—51 degrees

Exit—88 degrees

D01-3.9T-C-003 (3.9 exit hole diameter, entrance openings between 20-30 microns with taper from entrance to exit)

Entrance—78 degrees

Exit—102 degrees

APS and Mass Ejection Results

TABLE 16

| | 1% Polysorbate 80 (w/v) | | | |
|---|---|---|---|---|
| Ejector name | D01-1.7 | D01-2.0 | D01-3.5T-003 | D01-3.9 |
| MMAD (µm) | 1.472 | 1.356 | 1.862 | 2.474 |
| GSD | 2.344 | 2.24 | 1.98 | 2.13 |
| Mass ejection per shot (mg) | 6.64 | 5.56 | 19.86 | 23.04 |
| Repirable fraction % | 76.3 | 78.5 | 90.2 | 79.3 |

45 46

TABLE 17

| | 10% Polysorbate 80 (w/v) | | | |
|---|---|---|---|---|
| Ejector name | D01-1.7 | D01-2.0 | D01-3.5T-003 | D01-3.9 |
| MMAD (µm) | 1.646 | 1.406 | 2.174 | 3.178 |
| GSD | 1.964 | 2.058 | 2.046 | 2.014 |
| Mass ejection per shot (mg) | 2.8 | 5.58 | 19.42 | 18.66 |
| Repirable fraction % | 84.9 | 83.8 | 84.6 | 72.1 |

During testing, little to no foaming was observed at the ejector surfaces or in the fluid reservoir. As can be seen in the tables above, droplet diameters between about 1-2 microns, and respirable fractions above about 75% were obtained for the surfactant compositions under the test conditions. An aperture plate with an average opening diameter of about 3.5 microns provided optimal results, providing a respirable fraction of above about 90% with high mass ejection.

All publications and patent applications cited in this specification are herein incorporated by reference as if each individual publication or patent application were specifi-cally, and individually, indicated to be incorporated by reference.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings without departing from the essen-tial scope thereof. Therefore, it is intended that the invention not be limited to the particular embodiment disclosed as the best mode contemplated for carrying out this invention, but that the invention will include all embodiments falling within the scope of the appended claims.

What is claimed:

1. An ejector mechanism comprising:
a piezoelectric actuator coupled to an acoustic horn;
an aperture plate having a plurality of openings formed through its thickness and a fluid entrance side of one or more of said plurality of openings configured to pro-vide a surface contact angle of less than 90 degrees;
a removable fluid cartridge detachably coupled to the aperture plate; and
a sealing mechanism at an interface of the fluid cartridge and the aperture plate;
wherein the piezoelectric actuator is operable to oscillate the aperture plate at a frequency to thereby generate an ejected stream of droplets such that at least about 50% of the droplets have an average ejected droplet diameter of less than about 6 microns during use.

2. The ejector mechanism of claim 1, wherein the surface contact angle of less than 90 degrees at the fluid entrance side of one or more of said plurality of openings is obtained by a surface coating with a hydrophilic material, a surface structural modification, or a combination thereof.

3. The ejector mechanism of claim 2, wherein the hydro-philic material is selected from siloxane based coatings, isocyante based coatings, ethylene oxide based coatings, polyisocyanate based coatings, hydrocyclosiloxane based coatings, hydroxyalkylmethacrylate based coatings, hydroxyalkylacrylate based coatings, glycidylmethacrylate based coatings, propylene oxide based coatings, N-vinyl-2-pyrrolidone based coatings, latex based coatings, polyvinyl-chloride based coatings, or polyurethane based coatings.

4. The ejector mechanism of claim 1, wherein the aperture plate is configured such that at least the fluid entrance side of one or more of said plurality of openings is configured to provide the surface contact angle of between 2 and 80 degrees.

5. The ejector mechanism of claim 1, wherein the aperture plate is configured such that at least the fluid entrance side of one or more of said plurality of openings is configured to provide the surface contact angle of between 2 and 60 degrees.

6. The droplet delivery device of claim 1, wherein at least a portion of an interior of one or more of said plurality of openings is configured so as to provide a surface contact angle of less than 90 degree.

7. The ejector mechanism of claim 1, wherein the aperture plate is configured such that at a fluid exit side of one or more of said plurality of openings is configured to provide a surface contact angle of greater than 90 degrees.

8. The ejector mechanism of claim 7, wherein the aperture plate is configured such that at the fluid exit side of one or more of said plurality of openings is surface treated to provide the surface contact angle of between 90 degrees and 140 degrees.

9. The ejector mechanism of claim 7, wherein at least a portion of an interior of one or more of said plurality of openings is configured to provide a surface contact angle of greater than 90 degrees.

10. The ejector mechanism of claim 7, wherein the surface contact angle of greater than 90 degrees at the fluid exit side of one or more of said plurality of openings is obtained by a surface coating with a hydrophobic polymer.

11. The ejector mechanism of claim 10, wherein the hydrophobic polymer is selected from the group consisting of polytetrafluoroethylene, a siloxane, paraffin, and poly-isobutylene.

12. The ejector mechanism of claim 1, wherein the aperture plate is composed of a material selected from the group consisting of poly ether ether ketone (PEEK), poly-imide, polyetherimide, polyvinylidine fluoride (PVDF), ultra-high molecular weight polyethylene (UHMWPE), nickel, nickel-cobalt, nickel-palladium, palladium, plati-num, metal alloys thereof, and combinations thereof.

13. The ejector mechanism of claim 1, wherein one or more of the plurality of openings have different cross-sectional shapes or diameters to thereby provide ejected droplets having different average ejected droplet diameters.

14. An electronically actuated droplet delivery device for delivering a fluid composition as an ejected stream of droplets to a respiratory system of a subject, the device comprising:
a housing comprising a power source and a control board;
a mouthpiece positioned at an airflow exit of the device;
an ejector mechanism of claim 1 configured to generate the ejected stream of droplets; and
at least one differential pressure sensor positioned within the device, the at least one differential pressure sensor configured to activate the ejector mechanism upon sensing a pre-determined pressure change within the device to thereby generate the ejected stream of drop-lets;
wherein the ejector mechanism is configured to generate the ejected stream of droplets;
wherein the at least about 50% of the droplets have the average ejected droplet diameter of less than about 6 microns, such that at least about 50% of a mass of the ejected stream of droplets is delivered in a respirable range to the respiratory system of the subject during use.

15. The droplet delivery device of claim 14, wherein the mouthpiece and ejector mechanism are oriented such that an exit side of the aperture plate is perpendicular to a direction of air flow and the stream of droplets is ejected in parallel to the direction of air flow.

16. The droplet delivery device of claim 14, wherein the mouthpiece and ejector mechanism are oriented such that a fluid exit side of the aperture plate is oriented at an angle relative to a direction of air flow and the stream of droplets is ejected at an angle to the direction of air flow.

17. The droplet delivery device of claim 14, wherein the mouthpiece is removably coupled to the fluid cartridge.

18. A method for delivering fluid composition as an ejected stream of droplets in a respirable range to a respiratory system of a subject, the method comprising:

(a) generating the ejected stream of droplets from a fluid composition via an electronically actuated droplet delivery device of claim 14, wherein the at least about 50% of the ejected stream of droplets have the average ejected droplet diameter of less than about 6 μm; and (b) delivering the ejected stream of droplets to the respiratory system of the subject such that the at least about 50% of the mass of the ejected stream of droplets is delivered in the respirable range to the respiratory system of a subject during use.

19. The method of claim 18, wherein the fluid composition comprises a medicament, and is delivered to a subject to treat or ameliorate a disease, condition or disorder selected from the group consisting of asthma, COPD epilepsy, seizure disorders, pain, chronic pain, neuropathic pain, headache, migraine, arthritis, multiple sclerosis, anorexia, nausea, vomiting, anorexia, loss of appetite, anxiety, or insomnia.

20. The method of claim 18, wherein the at least about 50% of the ejected stream of droplets have an average ejected droplet diameter of less than about 3.2 μm.

21. The method of claim 18, wherein the ejected stream of droplets is delivered over a period of time less than about 2 seconds.

* * * * *